US 9,439,735 B2

(12) United States Patent
Guttman et al.

(10) Patent No.: US 9,439,735 B2
(45) Date of Patent: Sep. 13, 2016

(54) MRI-GUIDED INTERVENTIONAL SYSTEMS THAT CAN TRACK AND GENERATE DYNAMIC VISUALIZATIONS OF FLEXIBLE INTRABODY DEVICES IN NEAR REAL TIME

(75) Inventors: Michael Guttman, Potomac Falls, VA (US); Kimble L. Jenkins, Memphis, TN (US); Peter Piferi, Orange, CA (US); Kamal Vij, Chandler, AZ (US)

(73) Assignee: MRI Interventions, Inc., Irvine, CA (US)

(*) Notice: Subject to any disclaimer, the term of this patent is extended or adjusted under 35 U.S.C. 154(b) by 1102 days.

(21) Appl. No.: 12/796,017

(22) Filed: Jun. 8, 2010

(65) Prior Publication Data

US 2010/0312096 A1 Dec. 9, 2010

Related U.S. Application Data

(60) Provisional application No. 61/185,072, filed on Jun. 8, 2009, provisional application No. 61/187,323, filed on Jun. 16, 2009, provisional application No. 61/219,638, filed on Jun. 23, 2009, provisional application No. 61/261,103, filed on Nov. 13, 2009.

(51) Int. Cl.
*A61B 5/05* (2006.01)
*A61B 19/00* (2006.01)
(Continued)

(52) U.S. Cl.
CPC ............... *A61B 19/56* (2013.01); *A61B 5/415* (2013.01); *A61B 5/418* (2013.01); *A61B 19/50* (2013.01);
(Continued)

(58) Field of Classification Search
CPC .. A61B 5/418; A61B 19/50; A61B 19/5244; A61B 19/56; A61B 5/415; A61B 5/055; A61B 2019/562; A61B 18/1492; A61B 2017/00053; A61B 2017/00243; A61B 2018/00029; A61B 2018/00839; A61B 2018/1472; A61B 2019/501; A61B 2019/505; A61B 2019/507; A61B 2019/5236; A61B 2019/5251
USPC ...................... 607/2; 606/130; 600/414, 417
See application file for complete search history.

(56) References Cited

U.S. PATENT DOCUMENTS 3,499,435 A   3/1970   Rockwell et al.
3,661,158 A   5/1972   Berkovits
(Continued)

FOREIGN PATENT DOCUMENTS

EP   0466424   1/1992
EP   0498996   8/1992
(Continued)

OTHER PUBLICATIONS

Ackerman et al., "Rapid 3D Tracking of Small RF Coils [abstract]," Proceedings of the 5th Annual Meeting of ISMRM, Montreal, Canada pp. 1131-1132 (1986).
(Continued)

*Primary Examiner* — Long V Le
*Assistant Examiner* — Helene Bor
(74) *Attorney, Agent, or Firm* — Myers Bigel & Sibley, P.A.

(57) ABSTRACT

MRI guided cardiac interventional systems are configured to generate dynamic (interactive) visualizations of patient anatomy and medical devices during an MRI-guided procedure and may also include at least one user selectable 3-D volumetric (tissue characterization) map of target anatomy, e.g., a defined portion of the heart.

75 Claims, 29 Drawing Sheets
(19 of 29 Drawing Sheet(s) Filed in Color)

(51) Int. Cl.
*A61B 5/00* (2006.01)
*A61B 5/055* (2006.01)
*A61B 18/14* (2006.01)
*A61B 17/00* (2006.01)
*A61B 18/00* (2006.01)

(52) U.S. Cl.
CPC ............ *A61B 19/5244* (2013.01); *A61B 5/055* (2013.01); *A61B 18/1492* (2013.01); *A61B 2017/00053* (2013.01); *A61B 2017/00243* (2013.01); *A61B 2018/00029* (2013.01); *A61B 2018/00839* (2013.01); *A61B 2018/1472* (2013.01); *A61B 2019/501* (2013.01); *A61B 2019/505* (2013.01); *A61B 2019/507* (2013.01); *A61B 2019/5236* (2013.01); *A61B 2019/5251* (2013.01); *A61B 2019/562* (2013.01)

(56) References Cited

U.S. PATENT DOCUMENTS

| | | |
|---|---|---|
| 4,295,467 A | 10/1981 | Mann et al. |
| 4,431,005 A | 2/1984 | McCormick |
| 4,445,501 A | 5/1984 | Bresler |
| 4,572,198 A | 2/1986 | Codrington |
| 4,612,930 A | 9/1986 | Bremer |
| 4,639,365 A | 1/1987 | Sherry |
| 4,643,186 A | 2/1987 | Rosen et al. |
| 4,672,972 A | 6/1987 | Berke |
| 4,754,752 A | 7/1988 | Ginsburg et al. |
| 4,757,820 A | 7/1988 | Itoh |
| 4,766,381 A | 8/1988 | Conturo et al. |
| 4,791,934 A | 12/1988 | Brunnett |
| 4,793,359 A | 12/1988 | Sharrow |
| 4,813,429 A | 3/1989 | Eshel et al. |
| 4,823,812 A | 4/1989 | Eshel et al. |
| 4,832,023 A | 5/1989 | Murphy-Chutorian et al. |
| 4,859,950 A | 8/1989 | Keren |
| 4,932,411 A | 6/1990 | Fritschy et al. |
| 4,951,672 A | 8/1990 | Buchwald et al. |
| 4,960,106 A | 10/1990 | Kubokawa et al. |
| 4,989,608 A | 2/1991 | Ratner |
| 4,991,580 A | 2/1991 | Moore |
| 5,019,075 A | 5/1991 | Spears et al. |
| 5,078,140 A | 1/1992 | Kwoh |
| 5,095,911 A | 3/1992 | Pomeranz |
| 5,099,208 A | 3/1992 | Fitzpatrick et al. |
| 5,125,896 A | 6/1992 | Hojeibane |
| 5,151,856 A | 9/1992 | Halmann et al. |
| 5,154,179 A | 10/1992 | Ratner |
| 5,156,151 A | 10/1992 | Imran |
| 5,167,233 A | 12/1992 | Eberle et al. |
| 5,170,789 A | 12/1992 | Narayan et al. |
| 5,178,618 A | 1/1993 | Kandarpa |
| 5,190,046 A | 3/1993 | Shturman |
| 5,190,528 A | 3/1993 | Fonger et al. |
| 5,209,233 A | 5/1993 | Holland et al. |
| 5,211,165 A | 5/1993 | Dumoulin et al. |
| 5,217,010 A | 6/1993 | Tsitlik et al. |
| 5,218,025 A | 6/1993 | Kurimoto et al. |
| 5,230,338 A | 7/1993 | Allen et al. |
| 5,246,438 A | 9/1993 | Langberg |
| 5,251,120 A | 10/1993 | Smith |
| 5,251,635 A | 10/1993 | Dumoulin et al. |
| 5,255,680 A | 10/1993 | Darrow et al. |
| 5,263,485 A | 11/1993 | Hickey |
| 5,271,400 A | 12/1993 | Dumoulin et al. |
| 5,275,163 A | 1/1994 | McKimmon et al. |
| 5,276,927 A | 1/1994 | Day |
| 5,284,144 A | 2/1994 | Delannoy et al. |
| 5,290,266 A | 3/1994 | Rohling et al. |
| 5,293,868 A | 3/1994 | Nardella |
| 5,297,549 A | 3/1994 | Beatty et al. |
| 5,307,808 A | 5/1994 | Dumoulin et al. |
| 5,307,814 A | 5/1994 | Kressel et al. |
| 5,318,025 A | 6/1994 | Dumoulin et al. |
| 5,323,776 A | 6/1994 | Blakeley et al. |
| 5,323,778 A | 6/1994 | Kandarpa |
| 5,347,221 A | 9/1994 | Rubinson |
| 5,348,010 A | 9/1994 | Schnall et al. |
| 5,352,979 A | 10/1994 | Conturo |
| 5,353,795 A | 10/1994 | Souza et al. |
| 5,355,087 A | 10/1994 | Claiborne et al. |
| 5,358,515 A | 10/1994 | Hurter et al. |
| 5,362,475 A | 11/1994 | Gries et al. |
| 5,365,928 A | 11/1994 | Rhinehart et al. |
| 5,370,644 A | 12/1994 | Langberg |
| 5,377,678 A | 1/1995 | Dumoulin et al. |
| 5,383,454 A | 1/1995 | Bucholz |
| 5,384,537 A | 1/1995 | Ito et al. |
| 5,389,101 A | 2/1995 | Heilbrun et al. |
| 5,391,199 A | 2/1995 | Ben-Haim |
| 5,394,873 A | 3/1995 | Kraemer et al. |
| 5,398,683 A | 3/1995 | Edwards et al. |
| 5,398,692 A | 3/1995 | Hickey |
| 5,405,346 A | 4/1995 | Grundy et al. |
| 5,409,008 A | 4/1995 | Svenson et al. |
| 5,413,104 A | 5/1995 | Buijs et al. |
| 5,415,163 A | 5/1995 | Harms et al. |
| 5,422,576 A | 6/1995 | Kao et al. |
| 5,433,198 A | 7/1995 | Desai |
| 5,433,717 A | 7/1995 | Rubinsky et al. |
| 5,436,564 A | 7/1995 | Kreger et al. |
| 5,437,277 A | 8/1995 | Dumoulin et al. |
| 5,443,066 A | 8/1995 | Dumoulin et al. |
| 5,443,489 A | 8/1995 | Ben-Haim |
| 5,447,156 A | 9/1995 | Dumoulin et al. |
| 5,462,055 A | 10/1995 | Casey et al. |
| 5,480,422 A | 1/1996 | Ben-Haim |
| 5,507,743 A | 4/1996 | Edwards et al. |
| 5,512,825 A | 4/1996 | Atalar et al. |
| 5,529,068 A | 6/1996 | Hoenninger, III et al. |
| 5,531,227 A | 7/1996 | Schneider |
| 5,546,940 A | 8/1996 | Panescu et al. |
| 5,546,951 A | 8/1996 | Ben-Haim |
| 5,558,093 A | 9/1996 | Pomeranz |
| 5,568,809 A | 10/1996 | Ben-haim |
| 5,569,266 A | 10/1996 | Siczek |
| 5,577,502 A | 11/1996 | Darrow et al. |
| 5,588,432 A | 12/1996 | Crowley |
| 5,590,657 A | 1/1997 | Cain et al. |
| 5,617,026 A | 4/1997 | Yoshino et al. |
| 5,622,170 A | 4/1997 | Schulz |
| 5,634,467 A | 6/1997 | Nevo |
| 5,643,255 A | 7/1997 | Organ |
| 5,644,234 A | 7/1997 | Rasche et al. |
| 5,647,361 A | 7/1997 | Damadian |
| 5,657,755 A | 8/1997 | Desai |
| 5,662,108 A | 9/1997 | Budd et al. |
| 5,671,739 A | 9/1997 | Darrow et al. |
| 5,682,886 A | 11/1997 | Delp et al. |
| 5,682,897 A | 11/1997 | Pomeranz |
| 5,685,878 A | 11/1997 | Falwell et al. |
| 5,687,725 A | 11/1997 | Wendt |
| 5,694,945 A | 12/1997 | Ben-Haim |
| 5,699,801 A | 12/1997 | Atalar et al. |
| 5,706,823 A | 1/1998 | Wodlinger |
| 5,713,357 A | 2/1998 | Meulenbrugge et al. |
| 5,713,946 A | 2/1998 | Ben-Haim |
| 5,715,822 A | 2/1998 | Watkins et al. |
| 5,722,402 A | 3/1998 | Swanson et al. |
| 5,728,079 A | 3/1998 | Weber et al. |
| 5,738,096 A | 4/1998 | Ben-Haim |
| 5,739,691 A | 4/1998 | Hoenninger, III |
| 5,740,808 A | 4/1998 | Panescu et al. |
| 5,744,958 A | 4/1998 | Werne |
| 5,749,835 A | 5/1998 | Glantz |
| 5,754,085 A | 5/1998 | Danby et al. |
| 5,769,846 A | 6/1998 | Edwards et al. |
| 5,782,764 A | 7/1998 | Werne |
| 5,792,055 A | 8/1998 | McKinnon |
| 5,797,849 A | 8/1998 | Vesely et al. |
| 5,800,352 A | 9/1998 | Ferre et al. |

(56) References Cited

U.S. PATENT DOCUMENTS

| | | |
|---|---|---|
| 5,810,728 A | 9/1998 | Kuhn |
| 5,817,130 A | 10/1998 | Cox et al. |
| 5,820,580 A | 10/1998 | Edwards et al. |
| 5,833,608 A | 11/1998 | Acker |
| 5,836,874 A | 11/1998 | Swanson et al. |
| 5,840,025 A | 11/1998 | Ben-Haim |
| 5,840,031 A | 11/1998 | Crowley |
| 5,864,234 A | 1/1999 | Ludeke |
| 5,868,674 A | 2/1999 | Glowinski et al. |
| 5,882,304 A | 3/1999 | Ehnholm et al. |
| 5,891,047 A | 4/1999 | Lander et al. |
| 5,916,162 A | 6/1999 | Snelton et al. |
| 5,928,145 A | 7/1999 | Ocali et al. |
| 5,938,599 A | 8/1999 | Rasche et al. |
| 5,938,609 A | 8/1999 | Pomeranz |
| 5,944,022 A | 8/1999 | Nardella et al. |
| 5,951,472 A | 9/1999 | Van Vaals et al. |
| 5,961,528 A | 10/1999 | Birk et al. |
| 5,964,705 A | 10/1999 | Truwit et al. |
| 5,964,753 A | 10/1999 | Edwards |
| 5,978,696 A | 11/1999 | VomLehn et al. |
| 6,004,269 A | 12/1999 | Crowley et al. |
| 6,014,579 A | 1/2000 | Pomeranz et al. |
| 6,014,581 A | 1/2000 | Whayne et al. |
| 6,019,725 A | 2/2000 | Vesely et al. |
| 6,023,165 A | 2/2000 | Damadian et al. |
| 6,023,636 A | 2/2000 | Wendt et al. |
| 6,026,316 A | 2/2000 | Kucharczyk et al. |
| 6,027,500 A | 2/2000 | Buckles et al. |
| 6,031,375 A | 2/2000 | Atalar et al. |
| 6,045,532 A | 4/2000 | Eggers et al. |
| 6,045,553 A | 4/2000 | Iversen et al. |
| 6,052,614 A | 4/2000 | Morris, Sr. et al. |
| 6,052,618 A | 4/2000 | Dahlke et al. |
| 6,066,136 A | 5/2000 | Geistert |
| 6,067,371 A | 5/2000 | Gouge et al. |
| 6,070,094 A | 5/2000 | Swanson et al. |
| 6,071,281 A | 6/2000 | Burnside et al. |
| 6,073,039 A | 6/2000 | Berson |
| 6,076,007 A | 6/2000 | England et al. |
| 6,095,150 A | 8/2000 | Panescu et al. |
| 6,119,032 A | 9/2000 | Martin et al. |
| 6,128,522 A | 10/2000 | Acker et al. |
| 6,129,670 A | 10/2000 | Burdette et al. |
| 6,167,296 A | 12/2000 | Shahidi |
| 6,171,240 B1 | 1/2001 | Young et al. |
| 6,171,241 B1 | 1/2001 | McVeigh et al. |
| 6,179,833 B1 | 1/2001 | Taylor |
| 6,188,219 B1 | 2/2001 | Reeder et al. |
| 6,190,353 B1 | 2/2001 | Makower et al. |
| 6,192,144 B1 | 2/2001 | Holz |
| 6,201,394 B1 | 3/2001 | Danby et al. |
| 6,216,029 B1 | 4/2001 | Paltieli |
| 6,224,553 B1 | 5/2001 | Nevo |
| 6,226,542 B1 | 5/2001 | Reisfeld |
| 6,226,545 B1 | 5/2001 | Gilderdale |
| 6,231,570 B1 | 5/2001 | Tu et al. |
| 6,233,474 B1 | 5/2001 | Lemelson |
| 6,234,970 B1 | 5/2001 | Nevo et al. |
| 6,236,205 B1 | 5/2001 | Lüdeke et al. |
| 6,238,390 B1 | 5/2001 | Tu et al. |
| 6,241,725 B1 | 6/2001 | Cosman |
| 6,246,896 B1 | 6/2001 | Dumoulin et al. |
| 6,256,529 B1 | 7/2001 | Holupka et al. |
| 6,263,229 B1 | 7/2001 | Atalar et al. |
| 6,272,370 B1 | 8/2001 | Gillies et al. |
| 6,272,371 B1 | 8/2001 | Shlomo |
| 6,280,385 B1 | 8/2001 | Melzer et al. |
| 6,284,970 B1 | 9/2001 | Buskmiller et al. |
| 6,284,971 B1 | 9/2001 | Atalar et al. |
| 6,289,233 B1 | 9/2001 | Dumoulin et al. |
| 6,301,496 B1 | 10/2001 | Reisfeld |
| 6,317,619 B1 | 11/2001 | Boernert et al. |
| 6,322,558 B1 | 11/2001 | Taylor et al. |
| 6,332,089 B1 | 12/2001 | Acker et al. |
| 6,368,285 B1 | 4/2002 | Osadchy et al. |
| 6,370,434 B1 | 4/2002 | Zhang et al. |
| 6,375,606 B1 | 4/2002 | Garibaldi et al. |
| 6,385,472 B1 | 5/2002 | Hall et al. |
| 6,385,476 B1 | 5/2002 | Osadchy et al. |
| 6,393,314 B1 | 5/2002 | Watkins et al. |
| 6,408,202 B1 | 6/2002 | Lima et al. |
| 6,422,748 B1 | 7/2002 | Shepherd et al. |
| 6,428,537 B1 | 8/2002 | Swanson et al. |
| 6,430,429 B1 | 8/2002 | Van Vaals |
| 6,431,173 B1 | 8/2002 | Hoffmann |
| 6,456,867 B2 | 9/2002 | Reisfeld |
| 6,470,204 B1 | 10/2002 | Uzgiris et al. |
| 6,475,223 B1 | 11/2002 | Werp et al. |
| 6,487,431 B1 | 11/2002 | Iwano et al. |
| 6,487,437 B1 | 11/2002 | Viswanathan et al. |
| 6,490,473 B1 | 12/2002 | Katznelson et al. |
| 6,506,189 B1 | 1/2003 | Rittman, II et al. |
| 6,516,213 B1 | 2/2003 | Nevo |
| 6,522,913 B2 | 2/2003 | Swanson et al. |
| 6,529,758 B2 | 3/2003 | Shahidi |
| 6,529,764 B1 | 3/2003 | Kato et al. |
| 6,534,982 B1 | 3/2003 | Jakab |
| 6,535,755 B2 | 3/2003 | Ehnholm |
| 6,546,273 B2 | 4/2003 | Suzuki et al. |
| 6,546,279 B1 | 4/2003 | Bova et al. |
| 6,549,800 B1 | 4/2003 | Atalar et al. |
| 6,556,009 B2 | 4/2003 | Kellman et al. |
| 6,556,695 B1 | 4/2003 | Packer et al. |
| 6,558,333 B2 | 5/2003 | Gilboa et al. |
| 6,558,382 B2 | 5/2003 | Jahns et al. |
| 6,575,969 B1 | 6/2003 | Rittman, II et al. |
| 6,591,128 B1 | 7/2003 | Wu et al. |
| 6,591,130 B2 | 7/2003 | Shahidi |
| 6,593,884 B1 | 7/2003 | Gilboa et al. |
| 6,594,517 B1 | 7/2003 | Nevo |
| 6,597,935 B2 | 7/2003 | Prince et al. |
| 6,600,319 B2 | 7/2003 | Golan |
| 6,603,997 B2 | 8/2003 | Doody |
| 6,606,513 B2 | 8/2003 | Lardo et al. |
| 6,626,902 B1 | 9/2003 | Kucharczyk et al. |
| 6,628,980 B2 | 9/2003 | Atalar et al. |
| 6,633,773 B1 | 10/2003 | Reisfeld |
| 6,640,126 B2 | 10/2003 | Chang |
| 6,643,535 B2 | 11/2003 | Damasco et al. |
| 6,650,923 B1 | 11/2003 | Lesh et al. |
| 6,650,927 B1 | 11/2003 | Keidar |
| 6,654,628 B1 | 11/2003 | Silber et al. |
| 6,668,184 B1 | 12/2003 | Kleiman |
| 6,675,033 B1 | 1/2004 | Lardo et al. |
| 6,675,037 B1 | 1/2004 | Tsekos |
| 6,687,530 B2 | 2/2004 | Dumoulin |
| 6,690,963 B2 | 2/2004 | Ben-Haim et al. |
| 6,701,176 B1 | 3/2004 | Halperin et al. |
| 6,702,835 B2 | 3/2004 | Ginn |
| 6,711,429 B1 | 3/2004 | Gilboa et al. |
| 6,714,809 B2 | 3/2004 | Lee et al. |
| 6,725,079 B2 | 4/2004 | Zuk et al. |
| 6,740,883 B1 | 5/2004 | Stodilka et al. |
| 6,741,879 B2 | 5/2004 | Chang |
| 6,741,882 B2 | 5/2004 | Schäffter et al. |
| 6,743,248 B2 | 6/2004 | Edwards et al. |
| 6,771,067 B2 | 8/2004 | Kellman et al. |
| 6,780,183 B2 | 8/2004 | Jimenez, Jr. et al. |
| 6,785,572 B2 | 8/2004 | Yanof et al. |
| 6,788,062 B2 | 9/2004 | Schweikard et al. |
| 6,788,967 B2 | 9/2004 | Ben-Haim et al. |
| 6,793,664 B2 | 9/2004 | Mazzocchi et al. |
| 6,794,872 B2 | 9/2004 | Meyer et al. |
| 6,813,512 B2 | 11/2004 | Aldefeld et al. |
| 6,829,509 B1 | 12/2004 | MacDonald et al. |
| 6,847,210 B1 | 1/2005 | Eydelman et al. |
| 6,847,837 B1 | 1/2005 | Melzer et al. |
| 6,853,856 B2 | 2/2005 | Yanof et al. |
| 6,871,086 B2 | 3/2005 | Nevo et al. |
| 6,879,160 B2 | 4/2005 | Jakab |
| 6,892,090 B2 | 5/2005 | Verard et al. |
| 6,892,091 B1 | 5/2005 | Ben-Haim et al. |
| 6,896,678 B2 | 5/2005 | Tweardy |

(56) References Cited

U.S. PATENT DOCUMENTS

| | | | |
|---|---|---|---|
| 6,898,302 B1 | 5/2005 | Brummer |
| 6,898,454 B2 | 5/2005 | Atalar et al. |
| 6,904,307 B2 | 6/2005 | Karmarkar et al. |
| 6,920,347 B2 | 7/2005 | Simon et al. |
| 6,941,166 B2 | 9/2005 | MacAdam et al. |
| 6,949,929 B2 | 9/2005 | Gray et al. |
| 6,950,543 B2 | 9/2005 | King et al. |
| 6,958,035 B2 | 10/2005 | Friedman et al. |
| 6,961,602 B2 | 11/2005 | Fuimaono et al. |
| 6,961,608 B2 | 11/2005 | Hoshino et al. |
| 6,975,896 B2 | 12/2005 | Ehnholm et al. |
| 6,980,865 B1 | 12/2005 | Wang et al. |
| 6,985,775 B2 | 1/2006 | Reinke et al. |
| 6,988,001 B2 | 1/2006 | Greatbatch et al. |
| 6,994,094 B2 | 2/2006 | Schwartz |
| 6,996,430 B1 | 2/2006 | Gilboa et al. |
| 7,001,383 B2 | 2/2006 | Keidar |
| 7,020,312 B2 | 3/2006 | Desmedt et al. |
| 7,027,851 B2 | 4/2006 | Mejia |
| 7,027,854 B2 | 4/2006 | Fuderer et al. |
| 7,047,060 B1 | 5/2006 | Wu |
| 7,048,716 B1 | 5/2006 | Kucharczyk et al. |
| 7,056,294 B2 | 6/2006 | Khairkhahan et al. |
| 7,081,748 B2 | 7/2006 | Jakab |
| 7,082,325 B2 | 7/2006 | Hashimshony et al. |
| 7,089,045 B2 | 8/2006 | Fuimaono et al. |
| 7,095,890 B2 | 8/2006 | Paragios et al. |
| 7,096,057 B2 | 8/2006 | Hockett et al. |
| 7,099,712 B2 | 8/2006 | Fuimaono et al. |
| 7,123,013 B2 | 10/2006 | Gray |
| 7,133,714 B2 | 11/2006 | Karmarkar et al. |
| 7,134,438 B2 | 11/2006 | Makower et al. |
| 7,154,498 B2 | 12/2006 | Cowan et al. |
| 7,155,271 B2 | 12/2006 | Halperin et al. |
| 7,162,293 B2 | 1/2007 | Weiss |
| 7,187,964 B2 | 3/2007 | Khoury |
| 7,204,840 B2 | 4/2007 | Skakoon |
| 7,205,768 B2 | 4/2007 | Schulz et al. |
| 7,209,777 B2 | 4/2007 | Saranathan |
| 7,211,082 B2 | 5/2007 | Hall et al. |
| 7,220,265 B2 | 5/2007 | Chanduszko et al. |
| 7,225,012 B1 | 5/2007 | Susil et al. |
| 7,228,164 B2 | 6/2007 | Fuimaono et al. |
| 7,236,816 B2 | 6/2007 | Kumar et al. |
| 7,239,400 B2 | 7/2007 | Bock |
| 7,241,283 B2 | 7/2007 | Putz |
| 7,255,691 B2 | 8/2007 | Tolkoff et al. |
| 7,263,397 B2 | 8/2007 | Hauck et al. |
| 7,276,905 B2 | 10/2007 | Tamaroff et al. |
| 7,280,863 B2 | 10/2007 | Shachar |
| 7,285,119 B2 | 10/2007 | Stewart |
| 7,289,843 B2 | 10/2007 | Beatty et al. |
| 7,302,285 B2 | 11/2007 | Fuimaono et al. |
| 7,306,593 B2 | 12/2007 | Keidar et al. |
| 7,307,420 B2 | 12/2007 | Dumoulin |
| 7,308,299 B2 | 12/2007 | Burrell et al. |
| 7,311,705 B2 | 12/2007 | Sra |
| 7,320,695 B2 | 1/2008 | Carroll |
| 7,343,195 B2 | 3/2008 | Strommer et al. |
| 7,347,829 B2 | 3/2008 | Mark et al. |
| 7,363,090 B2 | 4/2008 | Halperin et al. |
| 7,386,339 B2 | 6/2008 | Strommer et al. |
| 7,398,116 B2 | 7/2008 | Edwards |
| 7,412,276 B2 | 8/2008 | Halperin et al. |
| 7,415,301 B2 | 8/2008 | Hareyama et al. |
| 7,418,289 B2 | 8/2008 | Hyde et al. |
| 7,422,568 B2 | 9/2008 | Yang et al. |
| 7,440,792 B2 | 10/2008 | Eggers |
| 7,463,920 B2 | 12/2008 | Purdy |
| 7,473,843 B2 | 1/2009 | Wang et al. |
| 7,474,913 B2 | 1/2009 | Durlak |
| 7,477,054 B2 | 1/2009 | Hoogenraad et al. |
| 7,480,398 B2 | 1/2009 | Kleen et al. |
| 7,483,732 B2 | 1/2009 | Zhong et al. |
| 7,495,438 B2 | 2/2009 | Prince et al. |
| 7,499,743 B2 | 3/2009 | Vass et al. |
| 7,505,808 B2 | 3/2009 | Anderson et al. |
| 7,505,809 B2 | 3/2009 | Strommer et al. |
| 7,505,810 B2 | 3/2009 | Harlev et al. |
| 7,542,793 B2 | 6/2009 | Wu et al. |
| 7,551,953 B2 | 6/2009 | Lardo et al. |
| 7,560,931 B2 | 7/2009 | Nabetani |
| 7,561,906 B2 | 7/2009 | Atalar et al. |
| 7,587,234 B2 | 9/2009 | Owens et al. |
| 7,593,558 B2 | 9/2009 | Boese |
| 7,599,730 B2 | 10/2009 | Hunter et al. |
| 7,602,190 B2 | 10/2009 | Piferi et al. |
| 7,606,611 B2 | 10/2009 | Speier |
| 7,609,862 B2 | 10/2009 | Black |
| 7,623,903 B2 | 11/2009 | Wacker |
| 7,632,265 B2 | 12/2009 | Hauck et al. |
| 7,660,623 B2 | 2/2010 | Hunter et al. |
| 7,689,264 B2 | 3/2010 | Nauerth |
| 7,697,972 B2 | 4/2010 | Verard et al. |
| 7,720,520 B2 | 5/2010 | Willis |
| 7,725,157 B2 | 5/2010 | Dumoulin et al. |
| 7,725,160 B2 | 5/2010 | Weber |
| 7,725,161 B2 | 5/2010 | Karmarkar et al. |
| 7,726,708 B2 | 6/2010 | Bourrieres |
| 7,742,799 B2 * | 6/2010 | Mueller et al. ............ 600/410 |
| 7,751,865 B2 | 7/2010 | Jascob et al. |
| 7,769,427 B2 | 8/2010 | Shachar |
| 7,787,935 B2 | 8/2010 | Dumoulin et al. |
| 7,811,294 B2 | 10/2010 | Strommer et al. |
| 7,815,623 B2 | 10/2010 | Bankiewicz |
| 7,822,460 B2 | 10/2010 | Halperin et al. |
| 7,840,253 B2 | 11/2010 | Tremblay et al. |
| 7,841,986 B2 | 11/2010 | He |
| 7,844,319 B2 | 11/2010 | Susil et al. |
| 7,844,320 B2 | 11/2010 | Shahidi |
| 7,848,788 B2 | 12/2010 | Tulley et al. |
| 7,853,332 B2 | 12/2010 | Olsen |
| 7,881,769 B2 | 2/2011 | Sobe |
| 7,894,877 B2 | 2/2011 | Lewin et al. |
| 7,920,911 B2 | 4/2011 | Hoshino et al. |
| 7,999,547 B2 | 8/2011 | Green et al. |
| 8,010,177 B2 | 8/2011 | Csavoy et al. |
| 8,473,030 B2 | 6/2013 | Greenan et al. |
| 8,532,742 B2 | 9/2013 | Unal et al. |
| 2001/0025142 A1 | 9/2001 | Wessels et al. |
| 2002/0019629 A1 | 2/2002 | Dietz et al. |
| 2002/0019644 A1 | 2/2002 | Hastings et al. |
| 2002/0055678 A1 | 5/2002 | Scott et al. |
| 2002/0058868 A1 | 5/2002 | Hoshino et al. |
| 2002/0103430 A1 | 8/2002 | Hastings et al. |
| 2002/0169371 A1 | 11/2002 | Gilderdale |
| 2002/0177771 A1 | 11/2002 | Guttman et al. |
| 2003/0055332 A1 | 3/2003 | Daum et al. |
| 2003/0074011 A1 * | 4/2003 | Gilboa et al. ............ 606/130 |
| 2003/0088181 A1 | 5/2003 | Gleich et al. |
| 2003/0093067 A1 | 5/2003 | Panescu |
| 2003/0097149 A1 | 5/2003 | Edwards et al. |
| 2003/0100829 A1 | 5/2003 | Zhong et al. |
| 2003/0158477 A1 | 8/2003 | Panescu |
| 2003/0208252 A1 | 11/2003 | O'Boyle et al. |
| 2003/0216642 A1 | 11/2003 | Pepin et al. |
| 2004/0006268 A1 | 1/2004 | Gilboa et al. |
| 2004/0015075 A1 | 1/2004 | Kimchy et al. |
| 2004/0024308 A1 | 2/2004 | Wickline et al. |
| 2004/0030244 A1 | 2/2004 | Garibaldi et al. |
| 2004/0034297 A1 | 2/2004 | Darrow et al. |
| 2004/0049121 A1 | 3/2004 | Yaron |
| 2004/0054279 A1 | 3/2004 | Hanley |
| 2004/0073088 A1 | 4/2004 | Friedman et al. |
| 2004/0082948 A1 | 4/2004 | Stewart et al. |
| 2004/0092813 A1 * | 5/2004 | Takizawa et al. ............ 600/423 |
| 2004/0111022 A1 | 6/2004 | Grabek et al. |
| 2004/0116800 A1 | 6/2004 | Helfer et al. |
| 2004/0143180 A1 | 7/2004 | Zhong et al. |
| 2004/0152968 A1 | 8/2004 | Iversen et al. |
| 2004/0152974 A1 | 8/2004 | Solomon |
| 2004/0171934 A1 | 9/2004 | Khan et al. |
| 2004/0181160 A1 | 9/2004 | Rudy |
| 2004/0181177 A1 | 9/2004 | Lee |

(56) References Cited

U.S. PATENT DOCUMENTS

| | | |
|---|---|---|
| 2004/0199072 A1 | 10/2004 | Sprouse et al. |
| 2004/0220470 A1 | 11/2004 | Karmarkar et al. |
| 2004/0225213 A1 | 11/2004 | Wang et al. |
| 2005/0010105 A1 | 1/2005 | Sra |
| 2005/0014995 A1 | 1/2005 | Amundson |
| 2005/0054910 A1 | 3/2005 | Tremblay et al. |
| 2005/0054913 A1 | 3/2005 | Duerk et al. |
| 2005/0113874 A1 | 5/2005 | Connelly |
| 2005/0119556 A1 | 6/2005 | Gillies et al. |
| 2005/0143651 A1 | 6/2005 | Verard et al. |
| 2005/0154279 A1 | 7/2005 | Li et al. |
| 2005/0154281 A1 | 7/2005 | Xue et al. |
| 2005/0154282 A1 | 7/2005 | Li et al. |
| 2005/0165301 A1 | 7/2005 | Smith et al. |
| 2005/0171427 A1 | 8/2005 | Nevo |
| 2005/0215886 A1 | 9/2005 | Schmidt |
| 2005/0222509 A1 | 10/2005 | Neason |
| 2005/0228252 A1 | 10/2005 | Neason |
| 2005/0256398 A1 | 11/2005 | Hastings et al. |
| 2005/0288599 A1 | 12/2005 | MacAdam et al. |
| 2006/0009756 A1 | 1/2006 | Francischelli et al. |
| 2006/0025677 A1 | 2/2006 | Verard et al. |
| 2006/0052706 A1 | 3/2006 | Hynynen |
| 2006/0058633 A1* | 3/2006 | Hoshino et al. ............... 600/410 |
| 2006/0100506 A1 | 5/2006 | Halperin et al. |
| 2006/0106303 A1 | 5/2006 | Karmarkar et al. |
| 2006/0116576 A1 | 6/2006 | McGee |
| 2006/0142657 A1 | 6/2006 | Quaid et al. |
| 2006/0184011 A1 | 8/2006 | Macaulay et al. |
| 2006/0224062 A1 | 10/2006 | Aggarwal et al. |
| 2006/0241392 A1 | 10/2006 | Feinstein |
| 2006/0247521 A1 | 11/2006 | McGee |
| 2006/0247684 A1 | 11/2006 | Halperin et al. |
| 2006/0258934 A1 | 11/2006 | Zenge et al. |
| 2007/0049817 A1 | 3/2007 | Preiss |
| 2007/0055328 A1 | 3/2007 | Mayse et al. |
| 2007/0062547 A1 | 3/2007 | Pappone |
| 2007/0073135 A1 | 3/2007 | Lee |
| 2007/0073179 A1 | 3/2007 | Afonso |
| 2007/0083195 A1 | 4/2007 | Werneth |
| 2007/0088295 A1 | 4/2007 | Bankiewicz |
| 2007/0088416 A1 | 4/2007 | Atalar et al. |
| 2007/0100223 A1 | 5/2007 | Liao et al. |
| 2007/0100232 A1 | 5/2007 | Hiller et al. |
| 2007/0106148 A1 | 5/2007 | Dumoulin |
| 2007/0112398 A1 | 5/2007 | Stevenson |
| 2007/0156042 A1 | 7/2007 | Unal et al. |
| 2007/0167726 A1 | 7/2007 | Unal et al. |
| 2007/0167736 A1 | 7/2007 | Dietz et al. |
| 2007/0167738 A1 | 7/2007 | Timinger et al. |
| 2007/0167745 A1 | 7/2007 | Case |
| 2007/0167801 A1* | 7/2007 | Webler et al. ............... 600/459 |
| 2007/0185485 A1 | 8/2007 | Hauck et al. |
| 2007/0208260 A1 | 9/2007 | Afonso |
| 2007/0233238 A1 | 10/2007 | Huynh et al. |
| 2007/0238970 A1 | 10/2007 | Kozerke et al. |
| 2007/0238978 A1 | 10/2007 | Kumar et al. |
| 2007/0238985 A1 | 10/2007 | Smith et al. |
| 2007/0249934 A1 | 10/2007 | Aksit et al. |
| 2007/0265521 A1 | 11/2007 | Redel et al. |
| 2007/0265642 A1 | 11/2007 | Chanduszko et al. |
| 2007/0270741 A1 | 11/2007 | Hassett et al. |
| 2007/0293724 A1 | 12/2007 | Saadat et al. |
| 2008/0009700 A1 | 1/2008 | Dumoulin et al. |
| 2008/0021336 A1 | 1/2008 | Dobak, III |
| 2008/0032249 A1 | 2/2008 | Scommegna et al. |
| 2008/0033278 A1 | 2/2008 | Assif |
| 2008/0033281 A1 | 2/2008 | Kroeckel |
| 2008/0039897 A1 | 2/2008 | Kluge et al. |
| 2008/0049376 A1 | 2/2008 | Stevenson |
| 2008/0058635 A1 | 3/2008 | Halperin et al. |
| 2008/0097189 A1 | 4/2008 | Dumoulin et al. |
| 2008/0097191 A1 | 4/2008 | Dumoulin et al. |
| 2008/0119919 A1 | 5/2008 | Atalar et al. |
| 2008/0125802 A1 | 5/2008 | Carroll |
| 2008/0130965 A1 | 6/2008 | Avinash et al. |
| 2008/0139925 A1 | 6/2008 | Lubock et al. |
| 2008/0143459 A1 | 6/2008 | Vernickel et al. |
| 2008/0154253 A1 | 6/2008 | Damasco et al. |
| 2008/0171931 A1 | 7/2008 | Maschke |
| 2008/0183070 A1 | 7/2008 | Unal et al. |
| 2008/0190438 A1 | 8/2008 | Harlev et al. |
| 2008/0214931 A1 | 9/2008 | Dickfield |
| 2008/0231264 A1 | 9/2008 | Krueger et al. |
| 2008/0243218 A1 | 10/2008 | Bottomley et al. |
| 2008/0262584 A1 | 10/2008 | Bottomley et al. |
| 2008/0275395 A1 | 11/2008 | Asbury et al. |
| 2008/0287773 A1 | 11/2008 | Harvey et al. |
| 2008/0306375 A1 | 12/2008 | Sayler et al. |
| 2008/0306376 A1 | 12/2008 | Hyde et al. |
| 2009/0079431 A1 | 3/2009 | Piferi et al. |
| 2009/0082783 A1 | 3/2009 | Piferi |
| 2009/0088627 A1 | 4/2009 | Piferi et al. |
| 2009/0102479 A1 | 4/2009 | Smith et al. |
| 2009/0112082 A1 | 4/2009 | Piferi et al. |
| 2009/0112084 A1 | 4/2009 | Piferi et al. |
| 2009/0118610 A1 | 5/2009 | Karmarkar et al. |
| 2009/0131783 A1 | 5/2009 | Jenkins et al. |
| 2009/0143696 A1 | 6/2009 | Najafi et al. |
| 2009/0171184 A1 | 7/2009 | Jenkins et al. |
| 2009/0171421 A1 | 7/2009 | Atalar et al. |
| 2009/0306643 A1 | 12/2009 | Pappone et al. |
| 2010/0066371 A1 | 3/2010 | Vij |
| 2010/0198052 A1 | 8/2010 | Jenkins et al. |
| 2011/0040175 A1 | 2/2011 | Shahidi |

FOREIGN PATENT DOCUMENTS

| | | |
|---|---|---|
| EP | 0557127 | 8/1993 |
| EP | 0673621 | 9/1995 |
| EP | 0701835 | 3/1996 |
| EP | 0701836 | 3/1996 |
| EP | 0702976 | 3/1996 |
| EP | 0732082 | 9/1996 |
| JP | 01-212569 | 8/1989 |
| JP | 2006-070902 | 3/1994 |
| JP | 07-255691 | 10/1995 |
| JP | 09-019441 | 1/1997 |
| JP | 09-094238 | 4/1997 |
| JP | 09-238924 | 9/1997 |
| JP | 09-299346 | 11/1997 |
| JP | 2001-238959 | 9/2001 |
| JP | 2003190117 | 7/2003 |
| JP | 2003-325475 | 11/2003 |
| JP | 2004-113808 | 4/2004 |
| JP | 2006-334259 | 12/2006 |
| WO | WO/87/04080 | 7/1987 |
| WO | WO/92/10213 | 6/1992 |
| WO | WO/94/23782 | 10/1994 |
| WO | WO/95/04398 | 2/1995 |
| WO | WO/96/12972 | 5/1996 |
| WO | WO/97/29685 | 8/1997 |
| WO | WO/97/29710 | 8/1997 |
| WO | WO/97/40396 | 10/1997 |
| WO | WO/98/52461 | 11/1998 |
| WO | WO/98/55016 | 12/1998 |
| WO | WO/99/00052 | 1/1999 |
| WO | WO/99/16352 | 4/1999 |
| WO | WO/00/10456 | 3/2000 |
| WO | WO/00/25672 | 5/2000 |
| WO | WO/00/48512 | 8/2000 |
| WO | WO/00/57767 | 10/2000 |
| WO | WO/00/68637 | 11/2000 |
| WO | WO/01/01845 | 1/2001 |
| WO | WO/01/06925 | 2/2001 |
| WO | WO/01/12093 | 2/2001 |
| WO | WO/01/56469 | 8/2001 |
| WO | WO/01/75465 | 10/2001 |
| WO | WO/01/87173 | 11/2001 |
| WO | WO/02/067202 | 8/2002 |
| WO | WO/02/083016 | 10/2002 |
| WO | WO/03/102614 | 12/2003 |
| WO | WO/2005/067563 | 7/2005 |
| WO | WO/2006/081409 | 8/2006 |

(56) References Cited

FOREIGN PATENT DOCUMENTS

| WO | WO/2006/136029 | 12/2006 |
|---|---|---|
| WO | WO/2007/002541 | 1/2007 |
| WO | WO/2007/005367 | 1/2007 |
| WO | WO/2007/033240 | 3/2007 |
| WO | WO/2007/066096 | 6/2007 |
| WO | WO/2008/015605 | 2/2008 |
| WO | WO/2008/023321 | 2/2008 |
| WO | WO/2008/082661 | 7/2008 |
| WO | WO/2008/129510 | 10/2008 |
| WO | WO/2006/094156 | 9/2009 |

OTHER PUBLICATIONS

Atalar et al., "High Resolution Intravascular MRI and MRS using a Catheter Receiver Coil," MRM 36:596-605 (1996).
Bahnson, "Strategies to Minimize the Risk of Esophageal Injury During Catheter Ablation for Atrial Fibrillation: Catheter Ablation for AF Using a Combination of RF and Cryothermy Ablation—a Practical Approach," Pacing Clin. Electrophysiol. 32:248-260 (2009).
Bhakta et al., "Principles of Electroanatomic Mapping," Indian Pacing Electrophysiol. J. 8:32-50 (2008).
Bleier et al., "Real-time Magnetic Resonance Imaging of Laser Heat Deposition in Tissue," Mag. Reson. Med. 21:132-137 (1991).
Burke et al., "Integration of Cardiac Imaging and Electrophysiology During Catheter Ablation Procedures for Atrial Fibrillation," J. Electrocardiol. 39:S188-S192 (2006).
Chen et al., "Right Atrial Focal Fibriliation: Electrophysiologic Characteristics and Radiofrequency Catheter Ablation," J. Cardiovasc. Electrophysiol. 10:328-335 (1999).
Cummings et al., "Assessment of Temperature, Proximity, and Course of the Esophagus During Radiofrequency Ablation within the Left Atrium," Circulation 112:459-464 (2005).
Dick et al., "Real Time MRI Enables Targeted Injection of Labeled Stem Cells to the Borders of Recent Porcine Myocardial Infarction Based on Functional and Tissue Characteristics," Proc. Intl. Soc. Mag. Reson. Med. 11:365 (2003).
Dick et al., "Magnetic Resonance Fluoroscopy Allows Targetd Delivery of Mesenchymal Stem Cells to Infarct Borders in Swine," Circulation 108:2899-2904 (2003).
Dumoulin et al,, "Simultaneous Acquisition of Phase-Contrast Angiograms and Stationary-Tissue Images with Hadamard Encoding of Flow-induced Phase Shifts," JMRI 1:399-404 (1991).
Dumoulin et al. "Real-Time Position Monitoring of Invasive Devices Using Magnetic Resonance," Mag. Reson. Med. 29:411-415 (1993).
Ector et al., Improved Efficiency in the EP Lab with syngo DynaCT Cardiac, AXIOM Innovations 26-32 (2008).
Edelman et al., "Magnetic Resonance Imaging," N. Engl. J. Med. 328:708-716 (1993).
Elgort, "Real-Time Catheter Tracking and Adaptive Imaging for Interventional Cardiovascular MRI," Case Western Reserve University student thesis (2005).
Elgort et al., "Real-time Catheter Tracking and Adaptive Imaging," J. Magnetic Resonance Imaging 18:621-626 (2003).
Fisher et al., "Atrial Fibrillation Ablation: Reaching the Mainstream: Methodology," Pacing Clin. Electrophysiol. 29:523-537 (2006).
Guttman et al., "Imaging of Myocardial Infarction for Diagnosis and Intervention Using Real-Time Interactive MRI without ECG-Gating or Breath-Holding," Mag. Reson. Med. 52:354-361 (2004).
Hamadeh et al., "Anatomy Based Multi-modal Medical Image Registration for Computer Integrated Surgery," SPIE 2355:178-188 (1994).
Hao and Hongo, "Use of Intracardiac Echocardiography During Catheter Ablation for Atrial Fibrillation: Maximizing Safety and Efficacy," EP Lab Digest 5(4) (2005).
Hillenbrand et al., "The Bazzoka Coil: A Novel Dual-Purpose Device for Active Visualization and Reduction of Cable Currents in Electrically Conductive Endovascular Instruments," Proc. Intl. Soc. Mag. Reson. Med. 13:197 (2005).
Jais et al., "Ablation Therapy for Atrial Fibrillation (AF): Past, Present and Future," Cardiovasc. Res. 54:337-346 (2002).
Jerwzewski et al., "Development of an MRI-Compatible Catheter for Pacing the Heart: Initial In Vitro and In Vivo Results," JMRI, ISHRM 6(6):948-949 (1996).
Jolesz et al., "MR Imaging of Laser-Tissue Interactions," Radiol. 168:249-253 (1988).
Kainz, "MR Heating Tests of MR Clinical Implants," J. Magnetic Resonance Imaging 26:450-451 (2007).
Kantor et al., "In vivo 31P Nuclear Magnetic Resonance Measurements in Canine Heart Using a Catheter-Coil," Circ. Res. 55:261-266 (1984).
Karmarkar, "An Active MRI Intramyocardial Injection Catheter," Proc. Intl. Soc. Mag. Reson. Med, 11:311 (2003).
Kerr et al., "Real-time Interactive MRI on a Conventional Scanner," MRM 38:355-367 (1997).
Kumar, "MR Imaging with a Biopsy Needle," Proc. Intl. Soc. Mag. Reson. Med. 9:2148 (2001).
Lewin et al., "Needle localization in MR-guided biopsy and aspiration: effects of field strength, sequence design, and magnetic field orientation," Am. J. Roentgenol. 166:1337-1345 (1996).
Morady, "Mechanisms and Catheter Ablation Therapy of Atrial Fibrillation," Tex. Heart Inst. J. 32:199-201 (2005).
Nademanee et al., "A New Approach for Catheter Ablation of Atrial Fibrillation: Mapping of the Electrophysiologic Substrate," J. Am. Coll. Cardiol. 43:2044-2053 (2004).
Ocali et al., "Intravascular Magnetic Resonance Imaging Using a Loopless Catheter Antenna," Mag. Reson. Med. 37:112-118 (1997).
Oral et al., "A Tailored Approach to Catheter Ablation of Paroxysmal Atrial Fibrillation," Circulation 113:1824-1831 (2006).
Pfister, "Architectures for Real-Time Volume Rendering," Future Generations Computer Systems 15(1):1-9 (1999).
Pickens, "Magnetic Resonance Imaging," Handbook of Medical Imaging (Beutel, et al. eds.) 1:373-461 (2000).
Quick et al., "Endourethral MRI," Mag. Reson. Med. 45:138-146 (2001).
Ratnayaka et al., "Interventional cardiovascular magnetic resonance: still tantalizing," J. Cardiovasc. Mag. Reson.10:62 (2008).
Reddy et al., "Integration of Cardiac Magnetic Resonance Imaging with Three-Dimensional Electroanatomic Mapping to Guide Left Ventiruclar Catheter Manipulation: Feasibility in a Porcine Model of Healed Myocardial Infarction," J. Am. Coll. Cardiol. 44(11):2202-2213 (2004).
Schirra et al., "A View-sharing Compressed Sensing Technique for 3D Catheter Visualization from Bi-planar Views," Proc. Intl. Soc. Mag. Reson. Med. 17:68 (2009).
Silverman et al., "Interactive MR-guided Biopsy in an Open Confiquration MR Imaging System," Radiol. 197:175-181 (1995).
Susil et al., "Multifunctional Interventional Devices for MRI: A Combined Electrophysiology/MRI Catheter," Mag. Reson. Med. 47:594-600 (2002).
Swain, "New MRI, Ultrasound Techniques Could Advance Breast Cancer Treatment," Medical Device & Diagnostic Industry Online (Apr. 1, 2004).
Torres et al.,"La cartografia electroanatomica (CARTO) en la ablacion de la fibrilacion auricular," Arch. Cardiol. Mex. 76(Supp 2):196-199 (2006).
Van Den Elsen et al., "Image Fusion Using Geometrical Features," SPIE 1808:172-186 (1992).
Weiss et al., "Transmission Line for Improved RF Safety of Interventional Devices," Mag. Reson. Med. 54:182-189 (2005).
Yang et al., "New Real-time Interactive Cardiac Magnetic Resonance Imaging System Complements Echocardiology," J. Am. Coll. Cardiol., 32:2049-2056 (1998).
Biosense Webster, Inc., CARTO™ XP Electroanatomical Navigation System [Brochure] (2004) (accessed at www.biosensewebster. com/products/pdf/B0037Carto_V7_Bro_Fnl.pdf).
Robin Medical, Inc., "The EndoScout® Tracking System" Robin Medical Inc. (2009) (accessed at http://www.robinmedical.com/endoscout.html).

(56) References Cited

OTHER PUBLICATIONS

Robin Medical, Inc., "Sensors" Robin Medical Inc. (2009) (accessed at http://www.robinmedical.com/sensors.html).

Robin Medical, Inc., EndoScout® Tracking System for MRI [Brochure] (2009) (accessed at http://www.robinmedical.com/Robin_Medical_Brochure.pdf).

Siemens USA, "Siemens Medical Solutions Revolutionizes Electrophysiology with syngo® DynaCT Cardiac Enhancement 3D Visualization of the Left Atrium, Reducing the Need for Pre-Procedural CT or MR Imaging, and Facilitating Improved Workflow," Siemens USA (2007) (accessed at http://press.siemens.us/index.php?s=43&item=94).

St. Jude Medical, Inc., "EnSite™ System," St. Jude Medical (2011) (accessed at http://www.sjmprofessional.com/Products/US/Mapping-and-Visualization/EnSite-System.aspx).

St. Jude Medical, Inc., "EnSite NavX™ Navigation & Visualization Technology," St. Jude Medical (2011) (accessed at http://www.sjmprofessional.com/Products/US/Mapping-and-Visualization/EnSite-NavX-Navigation-and-Visualization-Technology.aspx).

St. Jude Medical, Inc., "EnSite Array™ Catheter," St. Jude Medical (2011) (accessed at http://www.sjmprofessional.com/Products/Intl/Mapping-and-Visualization/EnSite-Array-Catheter.aspx).

St. Jude Medical, Inc., "EnSite Verismo™ Segmentation Tool," St. Jude Medical (2011) (accessed at http://www.sjmprofessional.com/Products/US/Mapping-and-Visualization/EnSite-Verismo-Segmentation-Tool.aspx).

St. Jude Medical, Inc., "EnSite Fusion™ Registration Module," St. Jude Medical (2011) (accessed at http://www.sjmprofessional.com/Products/US/Mapping-and-Visualization/EnSite-Fusion-Registration-Module.aspx).

St. Jude Medical, Inc., Ensite Fusion™ Registration Module Procedure Guide [Brochure] (2007) (accessed at http://www.ensitefusion.com/downloads/EnSiteFusionRegistrationModuleProcedureGuide.pdf).

Surgivision, Inc., "ClearTrace™ Cardiac Intervention System," Surgivision (2010) (accessed at http://www.surgivision.com/development).

Chorro et al., "Transcatheter ablation of the sinus node in dogs using high-frequency current," Eur Heart J 11:82-89 (1990).

Greenleaf et al., "Multidimensional Cardiac Imaging," Acoustical Imaging 20:403-411 (1993).

Grimson et al., "An Automatic Registration Method for Frameless Stereotaxy, Image Guided Surgery, and Enhanced Reality Visualization," IEEE Trans Med Imaging 15:129-140 (1996).

International Search Report and Written Opinion for corresponding PCT application No. PCT/US2010/037734, date of mailing Jan. 13, 2011.

\* cited by examiner

US 9,439,735 B2

MRI-GUIDED INTERVENTIONAL SYSTEMS THAT CAN TRACK AND GENERATE DYNAMIC VISUALIZATIONS OF FLEXIBLE INTRABODY DEVICES IN NEAR REAL TIME

RELATED APPLICATIONS

This application claims the benefit of and priority to U.S. Provisional Application Ser. No. 61/185,072 filed Jun. 8, 2009, U.S. Provisional Application Ser. No. 61/187,323 filed Jun. 16, 2009, U.S. Provisional Application Ser. No. 61/219,638 filed Jun. 23, 2009, and U.S. Provisional Application Ser. No. 61/261,103 filed Nov. 13, 2009, the contents of which are hereby incorporated by reference as if recited in full herein.

FIELD OF THE INVENTION

The present invention relates to MRI-guided systems and may be particularly suitable for MRI-guided cardiac systems such as EP systems for treating Atrial Fibrillation (AFIB).

BACKGROUND OF THE INVENTION

Conventional Cardiac EP (ElectroPhysiology) Systems are X-ray based systems which use electroanatomical maps. Electroanatomical maps are virtual representations of the heart showing sensed electrical activity. Examples of such systems include the Carto® electroanatomic mapping system from Biosense Webster, Inc., Diamond Bar, Calif., and the EnSite NavX® system from Endocardial Solutions Inc., St. Paul, Minn.

However, there remains a need for MRI-guided systems that can use MRI to obtain details of tissue not provided by X-ray based systems and/or to reduce patient exposure to radiation associated with interventional (diagnostic and/or therapeutic) procedures.

SUMMARY OF EMBODIMENTS OF THE INVENTION

Embodiments of the invention are directed to MRI-guided systems that have a new operational platform.

Some embodiments are directed to systems include a circuit configured to: (a) generate at least one near real time (RT) MRI image of at least a portion of a heart of a patient using relevant anatomical scan planes associated with a 3-D MRI image space having a coordinate system; (b) identify coordinates associated with a location of at least a distal portion of at least one flexible intrabody catheter in the 3-D MRI image space; and (c) render interactive near RT visualizations of the at least one flexible catheter in the 3-D image space. The at least one flexible catheter is not required to be in any of the relevant anatomical scan planes used to obtain MR data for the at least one near RT MRI image and the distal end portion of the flexible catheter can take on a curvilinear shape.

Other embodiments are directed to MRI guided interventional systems. The systems include at least one flexible intrabody interventional or diagnostic medical device configured to be able to take on a non-linear shape and be introduced into a patient via a tortuous and/or natural lumen path, the at least one medical device having at least one tracking coil that is connected to a channel of the MRI scanner; a circuit adapted to communicate with and/or reside in an MRI Scanner; and a display with a User Interface in communication with the circuit configured to display the visualizations during an MRI guided interventional procedure. The circuit is configured to: (a) obtain MR image data and generate a series of near real time (RT) MRI images of target anatomy of a patient during a surgical procedure using relevant anatomical scan planes associated with a 3-D MRI image space having a coordinate system; (b) identify coordinates associated with a location of at least a distal portion of the flexible intrabody medical device using the coordinate system of the 3-D MRI image space; and (c) render near RT interactive visualizations of the at least one flexible medical device in the 3-D image space with at least one near RT image of target patient anatomical structure and a registered pre-acquired volumetric model of the target anatomical structure of the patient. The circuit renders the visualizations to illustrate the at least one flexible medical device with a physical representation in the visualizations. The User Interface is configured to allow a user to (a) rotate the visualizations and (b) alter a displayed visualization to include only a near RT image of the target anatomy, to include the near RT image of the anatomy and the registered model of the anatomical structure, or to include only the registered model of the anatomical structure. The MRI Scanner is configured to interleave signal acquisition of tracking signals from the at least one tracking coil with image data for the near RT MRI images, and wherein the circuit is configured to electronically track the at least one flexible medical device in the 3-D image space independent of scan planes used to obtain the MR image data so that the at least one flexible device is not required to be in any of the relevant anatomical scan planes used to obtain MR image data for the at least one near RT MRI image, and wherein the distal end portion of the flexible medical device can take on a curvilinear shape.

Yet other embodiments are directed to MRI guided cardiac intervention systems. The systems include an MR Scanner having a plurality of channels; a plurality of flexible intrabody catheters, each having a plurality of tracking coils, each tracking coil of each catheter connected to a different MR Scanner channel; and at least one display in communication with the MR Scanner. The MR Scanner is configured to: (a) generate at least one near real time (RT) MRI image of at least a portion of a heart of a patient using relevant anatomical scan planes associated with a 3-D MRI image space having a coordinate system; (b) identify coordinates associated with a location of at least a distal portion of at least one flexible intrabody catheter in the 3-D MRI image space; and (c) render dynamic near RT visualizations of the at least one flexible catheter in the 3-D image space which show a volumetric pre-acquired model of the patient's heart registered to the imaging space with the near RT MRI image, wherein the at least one flexible catheter is not required to be in any of the relevant anatomical scan planes used to obtain MR image data for the at least one near RT MRI image, and wherein the distal end portion of the flexible catheter can take on a non-linear shape.

The circuit may be configured to show at least one of a plurality of user-selectable tissue characteristic maps or data associated therewith on the model or the selected tissue characteristic map in lieu of the model on the display, wherein the display is in communication with a User Interface that is configured to allow a user to selectively turn one or more of the tissue characterization maps on and off. When on, the tissue characteristic map or data therefrom is aligned with and/or registered to the pre-acquired volumetric 3-D model of the patient's heart (or shown in lieu thereof). The selectable tissue characteristic maps include a plurality of the following: a thermal tissue characterization map; an edema tissue characterization map; a first delayed enhancement tissue characterization map; a second delayed enhancement tissue characterization map taken after the first delayed enhancement tissue characterization map; a hypoxic tissue characterization map; a vasculature map; a fibrous map; and an ischemic tissue characterization map.

Still other embodiments are directed to MRI guided cardiac interventional systems. The systems include: a display; a processor in communication with the display and adapted to communicate with a MRI scanner; electronic memory coupled to the processor; and computer program code residing in the memory that is executable by the processor for:

(a) generating at least one near real time (RT) MRI image of at least a portion of a heart of a patient using relevant anatomical scan planes associated with a 3-D MRI image space having a coordinate system;

(b) identifying coordinates associated with a location of at least a distal portion of at least one flexible intrabody catheter in the 3-D MRI image space to track a location of a distal end portion of the catheter;

(c) rendering dynamic near RT visualizations of the at least one flexible catheter in the 3-D image space, wherein the at least one flexible catheter is not required to be in any of the relevant anatomical scan planes used to obtain MR data for the at least one near RT MRI image, and wherein the distal end portion of the flexible catheter can take on a non-linear shape;

(d) displaying a graphical user interface (GUI) containing at least one of the visualizations within the display; and (e) allowing a user to alter the visualizations using the GUI to selectively show different tissue characteristic maps or data from the selected tissue characteristic map.

The computer program code that is executable by the processor may be further adapted to automatically define at least one scan plane used by the MRI scanner for a target catheter-tissue interface site before and/or during the ablating step based on the tracked location of the of the catheter.

The tissue characterization map is color-coded to show scar or lesion formations associated with ablation sites created during the procedure.

Still other embodiments are directed to methods for carrying out an MRI-guided procedure. The methods include: (a) introducing a flexible intrabody medical device into a natural lumen or cavity of a patient during an MRI-guided procedure; (b) electronically obtaining tracking signals from tracking coils connected to an MR Scanner and attached to the flexible intrabody device during the MRI-guided procedure, wherein the intrabody device has a distal end portion that can take on a non-linear shape as it moves into position in the patient's body; (c) electronically identifying X, Y, Z coordinate locations in 3-D MRI image space of each of the tracking coils using the tracking signals; (d) obtaining MR image data and generating near RT MR images of the patient during the MRI-guided procedure; (e) obtaining a pre-acquired 3-D volumetric model of target anatomy of the patient and registering the model to the 3-D image space; and (f) generating near real time (RT) visualizations of the medical device showing: (i) the registered model of the patient's anatomy; (ii) a physical representation of at least a distal end portion of the medical device using the identified locations of the tracking coils; and (iii) at least one of the near RT MR images.

The method may further include electronically calculating a device-tissue interface location proximate a tip location of the device in the three dimensional image space using the identified locations of the tracking coils, wherein the calculating step projects axially forward a defined distance beyond the tip to define the device-tissue interface; and automatically defining at least one scan plane used to obtain the MR image data for the near RT images during and/or proximate in time to delivery of a therapeutic treatment and/or a diagnostic procedure.

The method may also or alternatively include electronically rotating the visualizations based on user input and electronically selectively altering a view of the displayed visualization based on user input so that the visualization includes the at least one flexible device with (a) only a near RT image of the target anatomy, (b) both the near RT image of the anatomy and the registered model of the anatomical structure, or (c) only the registered model of the anatomical structure.

Still other embodiments are directed to computer program products for facilitating an MRI-guided interventional therapy on a heart of a patient. The computer program product includes a computer readable storage medium having computer readable program code embodied in the medium. The computer-readable program code including: computer readable program code that computer readable program code that directs an MRI Scanner to obtain in an interleaved manner (i) tracking signal data from tracking coils associated with an intrabody flexible device and (ii) MR image data, both in the same 3-D image space with a coordinate system; computer readable program code that generates near real time (RT) MRI image of at least a portion of target anatomy of a patient using relevant anatomical scan planes; computer readable program code that identifies spatial coordinates associated with a location of at least a distal end portion of at least one flexible intrabody medical device in the 3-D MRI image space using the tracking signal data; and computer readable program code that renders dynamic near RT visualizations of the at least intrabody flexible medical device in the 3-D image space with near RT MRI images, wherein the at least one device is not required to be in any of the relevant anatomical scan planes used to obtain MR image data for the at least one near RT MRI images, and wherein the distal end portion of the device can take on a non-linear shape.

Some embodiments of the present invention can provide 3D, 4D and/or 4D visualization systems of multiple data sources, (e.g., multiparametric data) of cardiac tissue to provide relevant tissue characterization data and/or cardiac status during a therapy so that ablation and/or other therapy can be more precisely delivered, confirmed and/or visualized. For example, with cardiac ablation systems the visualizations can be rendered with an accurate or "true" lesion pattern from the therapy and/or an associated change in a physiological state of cardiac tissue during the therapy based, at least in part, on MR image data.

Yet other embodiments are directed to MRI guided interventional systems that include a circuit in communication with a display with a User Interface. The circuit is configured to: (a) provide a patient planning map and allow a user to identify at least one target treatment site on the patient planning map using the User Interface; then (b) register the planning map in 3-D MRI image space prior to or during an MRI guided procedure; and (c) define locations of the at least one treatment site in 3-D MRI image space based on the registered planning map.

The circuit can be configured to accept user input via the User Interface to selectively fade and/or turn on and off a visual indication of the at least one target treatment site in position in 3-D MRI imaging space in rendered visualizations during an MRI guided procedure.

The circuit can be configured to allow a user to select whether to show tissue characterization data on the display in interactive visualizations during the MRI guided procedure in different viewing formats including: (a) on a registered map with near RT image data; or (b) in near RT images without a map in visualizations during an MRI guided procedure.

Embodiments of the invention are directed to systems, methods, User Interfaces and a processor configured to automatically obtain MR image data and tracking data for one or more intrabody flexible devices (e.g., catheters, probes, delivery devices, needles and the like). This data alone or with other physiologic or a priori data regarding a particular device and/or anatomy of a patient can be used to generate the visualizations in a manner that visually shows (e.g., via color, opacity and/or intensity) target anatomical tissue using MR image data and a physical representation of at least a distal end portion of the at least one flexible device in near real time on a display during a surgical procedure.

Embodiments of the invention are particularly suitable for MRI-guided EP procedures for ablating tissue to arrhythmias such as AFIB or injecting therapeutics to treat heart failure.

The system may also be suitable for delivering a therapeutic agent or carrying out another treatment or diagnostic evaluation for any intrabody location, including, for example, the brain, heart, gastrointestinal system, genourinary system, spine (central canal, the subarachnoid space or other region), vasculature or other intrabody location.

It is noted that any one or more aspects or features described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF EMBODIMENTS OF THE INVENTION

Figure 1:
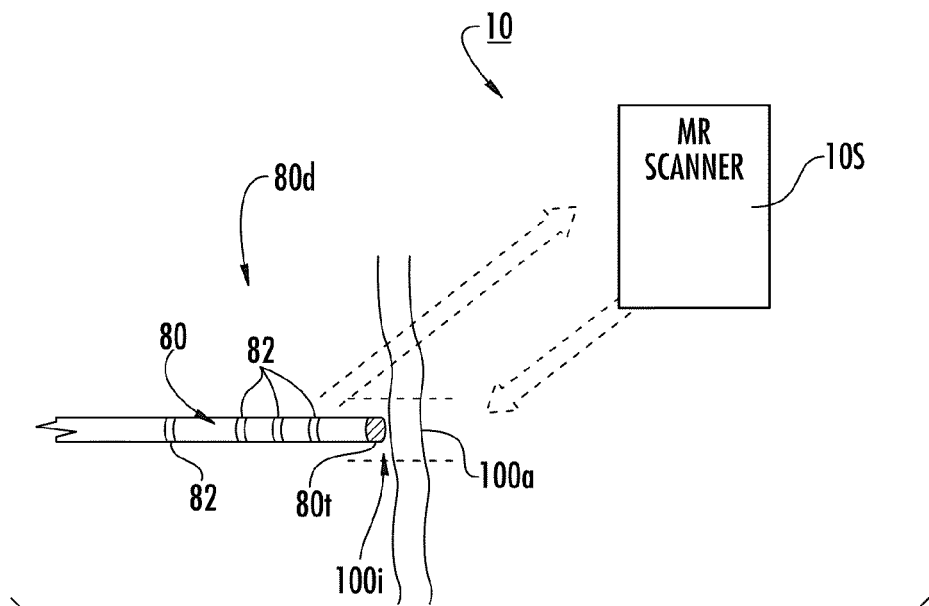
FIG. 1 is a schematic illustration of an MRI-guided system configured to show a device tissue interface using near RT MRI data according to embodiments of the present invention.

The present invention will now be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. It will be appreciated that although discussed with respect to a certain embodiment, features or operation of one embodiment can apply to others.

In the drawings, the thickness of lines, layers, features, components and/or regions may be exaggerated for clarity and broken lines (such as those shown in circuit of flow diagrams) illustrate optional features or operations, unless specified otherwise. In addition, the sequence of operations (or steps) is not limited to the order presented in the claims unless specifically indicated otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when a feature, such as a layer, region or substrate, is referred to as being "on" another feature or element, it can be directly on the other element or intervening elements may also be present. In contrast, when an element is referred to as being "directly on" another feature or element, there are no intervening elements present. It will also be understood that, when a feature or element is referred to as being "connected" or "coupled" to another feature or element, it can be directly connected to the other element or intervening elements may be present. In contrast, when a feature or element is referred to as being "directly connected" or "directly coupled" to another element, there are no intervening elements present. Although described or shown with respect to one embodiment, the features so described or shown can apply to other embodiments.

The term "circuit" refers to an entirely software embodiment or an embodiment combining software and hardware aspects, features and/or components (including, for example, at least one processor and software associated therewith embedded therein and/or executable by and/or one or more Application Specific Integrated Circuits (ASICs), for programmatically directing and/or performing certain described actions or method steps). The circuit can reside in one location or multiple locations, it may be integrated into one component or may be distributed, e.g., it may reside entirely in an MR Scanner control cabinet, partially in the MR Scanner control cabinet, totally in a separate component or system such as a clinician workstation but communicate with MR Scanner electronics and/or in an interface therebetween, in a remote processor and combinations thereof.

The term "map" is used interchangeably with the term "model" and refers to a volumetric rendering of a patient's target anatomy. The term "tissue characterization (or characteristic) map" refers to a rendered volumetric (typically 3-D, 4-D or 4-DMP) visualization and/or image of a target anatomical structure or portion thereof showing one or more selected tissue parameters, conditions, or behaviors of cardiac tissue using MR image data, e.g., the tissue characterization map is a rendered partial or global anatomical map that shows at least one defined tissue characteristic of the target anatomy, e.g., heart or portion thereof (for example, the left atrium) in a manner that illustrates relative degrees or measures of the tissue characteristic(s) of interest, typically in different colors, opacities and/or intensities. Notably, a tissue characterization map or model is to be contrasted with an electroanatomical (EA) map or model which is based on sensed electrical activity of different regions of the heart rather than on MR image data. In some embodiments, tissue data from an electroanatomical map and/or the tissue characteristic map or the map(s) themselves can be selectively turned on and off (on a display) or faded. A tissue characteristic map may be included with an EA model and/or two or more tissue characteristic maps may be merged into or shown as a composite map or may be shown overlying and aligned with one another. Thus, the visualizations can use one or both types of volumetric tissue maps, shown separately, overlaid on each other and/or integrated as a composite or superimposed map. The terms "fade" and "faded" refer to making the so-called feature less visually dominant in a visualization by dimming the intensity, color and/or opacity relative to other features in the visualization.

The actual visualization can be shown on a screen or display so that the map of the anatomical structure is in a flat 2-D and/or in 2-D what appears to be 3-D volumetric images with data representing features or electrical output with different visual characteristics such as with differing intensity, opacity, color, texture and the like. A 4-D map can either illustrate a 3-D anatomical structure (e.g., heart) with movement (e.g., a beating heart and/or a heart with blood flow, breathing lungs or other moving structure) or show additional information over a 3-D anatomic model of the contours of the heart or portions thereof. The term "heart" can include adjacent vasculature, e.g., the branching of the pulmonary veins.

The term "4-D multiparametric visualization" (4-DMP) means a 4-D visualization image (e.g., a 3-D image of a beating heart) with functional spatially encoded or correlated information shown on the visualization. The 4-DMP visualization can be provided with fMRI data and/or one or more tools used to provide the spatially correlated functional data (e.g., electrical) data of the heart based on the 3-D model of the tool. Again, the 3-D, 4-D and/or 4-DMP visualizations are not merely an MRI image or MRI images of the patient during a procedure but are rendered visualizations that can combine multiple sources of data to provide a visualization of spatially encoded function with anatomical shape. Thus, the visualizations can comprise a rendered model of the patient's target anatomy with a rendered visualization of at least one medical device in an intrabody location with respect to the model and along with near RT MRI image data of the anatomical structure. The figures may include prophetic examples of screen shots of visualizations and the like and do not necessarily represent actual screen shots of a surgical system/display.

The term "close-up" means that the associated image is shown enlarged relative to a global image or typical navigation view to show local tissue. The term, "high-resolution" means that the image data is obtained with higher resolution than normal image data (usually requiring longer scan times and/or using an internal antenna to increase SNR). For example, the local tissue ablation views may be shown in higher resolution than MRI images in the navigation view. The term en face refers to a view through a tissue wall (e.g., myocardial wall) and substantially parallel (tangent) to the surface.

The term "programmatically" means that the operation or step can be directed and/or carried out by a digital signal processor and/or computer program code. Similarly, the term "electronically" means that the step or operation can be carried out in an automated manner using electronic components rather than manually or using merely mental steps.

At least a portion of the intrabody medical device is tracked and its position identified in 3-D imaging space (e.g., X, Y, Z coordinates). Various location tracking means for the tool and/or registration means for the catheter to the imaging space can be employed. For example, the intrabody device can include fiducial markers or receive antennas combinations of same. The term "fiducial marker" refers to a marker that can be identified using electronic image recognition, electronic interrogation of MRI image data, or three-dimensional electrical signals to define a position and/or find the feature or component in 3-D space. The fiducial marker can be provided in any suitable manner, such as, but not limited to a geometric shape of a portion of the tool, a component on or in the tool, a coating or fluid-filled coating (or combinations of different types of fiducial markers) that makes the fiducial marker(s) MRI-visible that are active or passive (e.g., if passive, the marker does not provide MR signal) with sufficient intensity for identifying location and/or orientation information for the tool and/or components thereof in 3-D space. As will be discussed further below, in particular embodiments, the device comprises at least one tracking coil electrically connected to the MRI Scanner that generate signals that are detected (received) by the MR Scanner and used to identify respective locations of the coils in a 3-D coordinate system of the imaging space, and hence the device with such tracking coils, in the 3-D image space.

The terms "MRI or MR Scanner" are used interchangeably to refer to a Magnetic Resonance Imaging system and includes the magnet, the operating components, e.g., RF amplifier, gradient amplifiers and operational circuitry including, for example, processors (the latter of which may be held in a control cabinet) that direct the pulse sequences, select the scan planes and obtain MR data.

The term "RF safe" means that the device (e.g., catheter) and any (conductive) lead is configured to operate safely when exposed to RF signals, particularly RF signals associated with MRI systems, without inducing unplanned current that inadvertently unduly heats local tissue or interferes with the planned therapy. The term "MRI visible" means that the device is visible, directly or indirectly, in an MRI image. The visibility may be indicated by the increased SNR of the MRI signal proximate the device. The device can act as an MRI receive antenna to collect signal from local tissue and/or the device actually generates MRI signal itself, such as via suitable medical grade hydro-based coatings, fluid (e.g., aqueous fluid) filled channels or lumens. The term "MRI compatible" means that the so-called component(s) is safe for use in an MRI environment and as such is typically made of a non-ferromagnetic MRI compatible material(s) suitable to reside and/or operate in a high magnetic field environment. The term "high-magnetic field" refers to field strengths above about 0.5 T, typically above 1.0 T, and more typically between about 1.5 T and 10 T. Embodiments of the invention may be particularly suitable for 1.5 T and/or 3.0 T systems.

Generally stated, advantageously, the system can be configured so that the surgical space is the imaging space and the tracking is performed in the imaging space so that there is no requirement to employ a discrete tracking system that must then be registered to the imaging space. In some embodiments, the tracking is carried out in the same 3-D imaging space but the flexible intrabody medical device is tracked independent of the imaging scan planes used to obtain the MR image data for generating images of local anatomy and is shown as a physical representation in the visualization.

The term "near real time" refers to both low latency and high frame rate. Latency is generally measured as the time from when an event occurs to display of the event (total processing time). For tracking, the frame rate can range from between about 100 fps (frames per second) to the imaging frame rate. In some embodiments, the tracking is updated at the imaging frame rate. For near 'real-time' imaging, the frame rate is typically between about 1 fps to about 20 fps, and in some embodiments, between about 3 fps to about 7 fps. For lesion imaging, a new image can be generated about every 1-7 s, depending on the sequence used. The low latency required to be considered "near real time" is generally less than or equal to about 1 second. In some embodiments, the latency for tracking information is about 0.01 s, and typically between about 0.25-0.5 s when interleaved with imaging data. Thus, with respect to tracking, visualizations with the location, orientation and/or configuration of a known intrabody device can be updated with low latency between about 1 fps to about 100 fps. With respect to imaging, visualizations using near real time MR image data can be presented with a low latency, typically within between about 0.01 ms to less than about 1 second, and with a frame rate that is typically between about 1-20 fps. Together, the system can use the tracking signal and image signal data to dynamically present anatomy and one or more intrabody devices in the visualization in near real-time. In some embodiments, the tracking signal data is obtained and the associated spatial coordinates are determined while the MR image data is obtained and the resultant visualization(s) with the intrabody device (e.g., flexible catheter using the tracking coil data) and the near RT MR image(s) is generated.

In some embodiments, MR image data is obtained during an active treatment such as during an ablation, delivery of a drug or other material, valve repair or replacement, lining repair, and the like, and the resultant visualization(s) with the flexible intrabody device used for this treatment (e.g., catheter, needle and the like) along with one or more near RT MR images of local anatomy is substantially continuously rendered/generated. In some particular embodiments, the system is a cardiac EP system used to place a lesion pattern of transmural lesions that creates a desired electrical isolation in the cardiac tissue to treat the at-risk pathology/condition (e.g., AFIB). The ablations are not required to be followed in any particular direction or order. The ablation can be carried out to generate one or more continuous and/or contiguous lesions and/or several non-continuous or non-contiguous lesions. The lesions may be linear (whether straight or with a curvature such as circular or curvilinear).

The term "intrabody device" is used broadly to refer to any diagnostic or therapeutic medical device including, for example, catheters, needles (e.g., injection, suture, and biopsy), forceps (miniature), knives or other cutting members, ablation or stimulation probes, injection or other fluid delivery cannulas, mapping or optical probes or catheters, sheaths, guidewires, fiberscopes, dilators, scissors, implant material delivery cannulas or barrels, and the like, typically having a size that is between about 5 French to about 12 French, but other sizes may be appropriate.

FIG. 1 illustrates an MRI interventional system 10 with a scanner 10S and a flexible intrabody medical device 80 proximate target tissue 100 at a device-tissue interface 100i. The system 10 can be configured to electronically track the 3-D location of the device 80 in the body and identify and/or "know" the location of the tip portion of the device 80t (e.g., the ablation or needle tip) in a coordinate system associated with the 3-D imaging space. As shown in FIG. 1, the device 80 can include a plurality of spaced apart tracking members 82 on a distal end portion thereof. In a particular embodiment, the device 80 can be an ablation catheter and the tip can include an ablation electrode, ablation balloon, or other ablation source 80e (typically at least one at a distal end portion of the device). Where used, the electrode can be both a sensing and ablation electrode.

Figure 2:
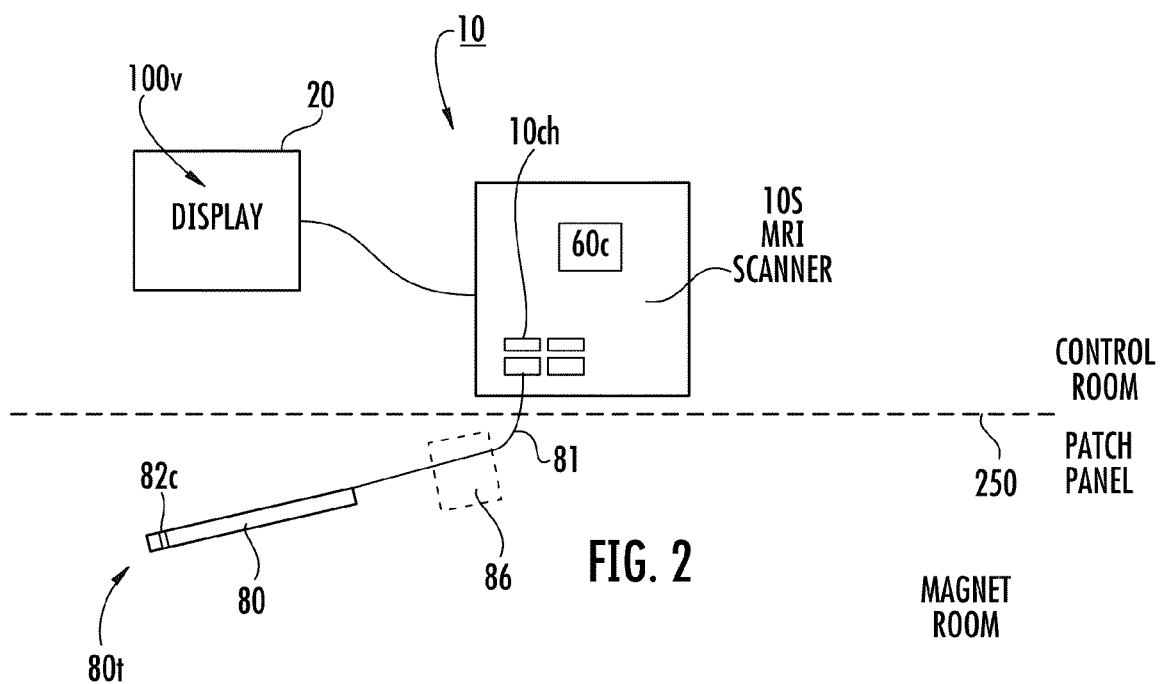
FIG. 2 is a schematic illustration of an intrabody device with a tracking coil electrically connected to a Scanner channel according to embodiments of the present invention.

The tracking members 82 can comprise miniature tracking coils, passive markers and/or a receive antenna. In a preferred embodiment, the tracking members 82 include at least one miniature tracking coil 82c that is connected to a channel 10ch of an MRI Scanner 10S (FIG. 2). The MR Scanner 10S can be configured to operate to interleave the data acquisition of the tracking coils with the image data acquisition. The tracking data is typically acquired in a 'tracking sequence block' which takes about 10 msec (or less). In some embodiments, the tracking sequence block can be executed between each acquisition of image data (the latter can be referred to as an 'imaging sequence block'). So the tracking coil coordinates can be updated immediately before each image acquisition and at the same rate. The tracking sequence can give the coordinates of all tracking coils simultaneously. So, typically, the number of coils used to track a device has substantially no impact on the time required to track them.

Embodiments of the present invention provide a new platform that can help facilitate clinical decisions during an MRI-guided procedure and can present near real time anatomical image data to the clinician in an interactive visualization 100v. The visualizations 100v (FIGS. 5A-5D) can be dynamically generated as the intrabody device 80 moves in the body into and/or about a target location, as a user rotates, crops or otherwise alters a displayed visualization or view and/or during an active therapy or diagnostic procedure step, e.g., while ablating at target lesion sites or while approaching and/or delivering a different therapeutic treatment, with minimal latent time between serial MRI image data acquisitions, typically less than about 5 seconds, typically substantially continuously with a minimal latent time of about 1 second or less, such as between about 0.001 seconds and 1 second. Together, the system 10 can use the tracking signal(s) and image signal data to dynamically track the device 80 (which is typically a plurality of devices) and present visualizations of the anatomy and one or more intrabody devices 80 in near real-time. Notably, while the at least one device is tracked in 3-D image space, the device is not required to be imaged and is not required to be in any of the relevant anatomical scan planes used to obtain MR data for the near RT MRI images.

The term "physical representation" means that a device is not actually imaged but rather rendered with a physical form in the visualizations. Typically, the physical representation is a partial physical representation which shows the distal end portion of the device in the body in the 3-D MR image space. The physical representation may be of any form including, for example, a graphic with at least one geometric shapes, icons and/or symbols. The physical representation is typically in 3-dimensional form. In some particular embodiments, the physical representation may be a virtual graphic substantially replica substantially corresponding to an actual shape and configuration of the physical appearance and/or configuration of a portion (e.g., distal end portion) of the associated device (see, e.g., FIGS. 22A, 22B). The physical representation can be electronically generated based on a priori knowledge of the dimensions and configuration of the device. The tip and each tracking coil on a distal end of a particular device may be shown in a geometric shape (the same or different shapes, e.g., an arrow for the tip and a sphere or block or other (typically 3-D) geometric shape or shapes for tracking coils, each in its real location in the 3-D space and in its relative position on the device and each may be rendered with the same or a different color and with the same or a different shape. For example, the tip and each proximate tracking coil may be shown in a different color.

The term "tortuous" refers to a curvilinear pathway in the body, typically associated with a natural lumen such as vasculature. The term "dynamic visualizations" refers to a series of visualizations that show the movement of the device(s) in the body and can show a beating heart or movement based on respiratory cycle and the like.

The term "pre-acquired" means that the data used to generate the model or map of the actual patient anatomy was obtained prior to the start of an active therapeutic or diagnostic procedure and can include immediately prior to but during the same MRI session or at an earlier time than the procedure (typically days or weeks before).

Embodiments of the present invention can be configured to guide and/or place flexible intrabody diagnostic and/or interventional devices in an MRI environment (e.g., interventional medical suite) to any desired internal region of interest of a subject, typically via a natural lumen and/or tortuous path so that the intrabody devices can take on different non-linear configurations/shapes as it moves into position through a target pathway (which may be a natural lumen or cavity). The subjects can be animal and/or human subjects.

Some embodiments of the invention provide systems that can be used to treat cardiac disorders such as arrythmias including, but not limited to AFIB, or to repair or replace cardiac valves, repair, flush or clean vasculature and/or place stents, and/or to deliver stem cells or other cardio-rebuilding cells or agents or products into cardiac tissue, such as a heart wall, via a minimally invasive MRI guided procedure while the heart is beating (i.e., not requiring a non-beating heart with the patient on a heart-lung machine). The cardiac procedures can be carried out from an inside of the heart or from an outside of the heart. The cardiac procedures may be directed to treating cardiac arrythmias or heart failure (e.g., congestive heart failure, reduced heart function, and the like).

Embodiments of the system are also suitable for delivering a therapeutic agent or carrying out another treatment or diagnostic evaluation for other intrabody locations, including, for example, the brain, gastrointestinal system, genourinary system, spine (central canal, the subarachnoid space or other region), vasculature or other intrabody locations. Additional discussion of exemplary target regions can be found at the end of this document.

Figure 37:
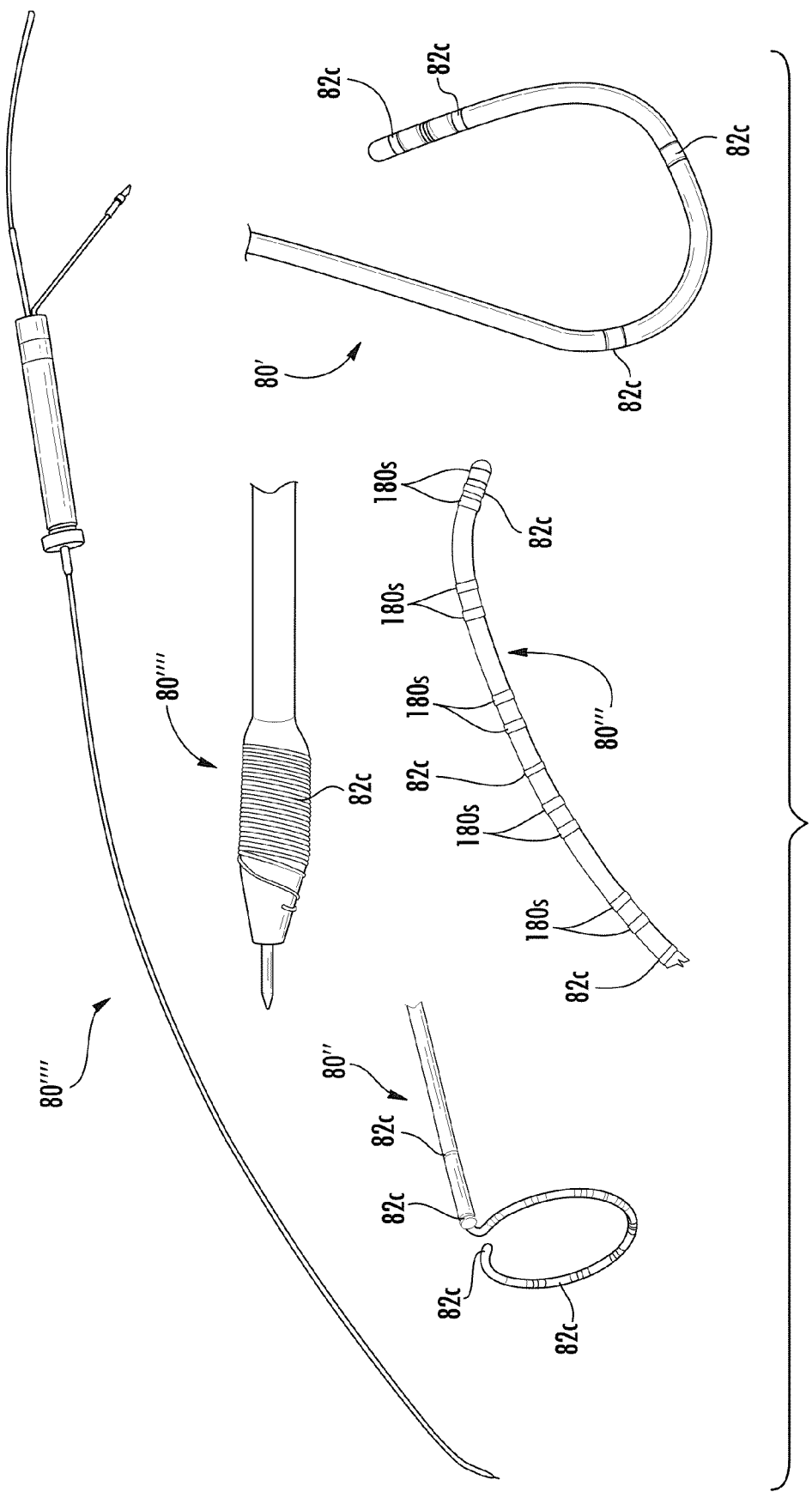
FIG. 37 is a schematic illustration of examples of different intrabody devices that can be used with embodiments of the present invention.

To be clear, while detailed drawings of exemplary flexible devices 80 are shown for tracking coils for transseptal needles (septal puncture kit components) and mapping and/or ablation catheters for cardiac use, embodiments of the invention are not intended to be limited to these devices nor to cardiac use. Exemplary devices are listed above (and see, FIG. 37). Exemplary (non-cardiac) intrabody locations are listed at the end of this document. For example, the device can be implemented as injection catheters or diagnostic biopsy needles and the like for any target anatomical location in the body. See, e.g., U.S. patent application Ser. No. 10/769,994 (intramyocardial injection needle), U.S. Pat. No. 7,236,816 (biopsy needle), and U.S. Pat. No. 6,606,513 (transseptal needle), the contents of which are hereby incorporated by reference as if recited in full herein. Examples of a loop catheter 80", mapping catheter 80'", (deformable) ablation catheter 80', and injection needle catheter 80"" (one 80"" view is an enlarged view of the needle with a tracking coil) are shown in FIG. 37. The loop catheter and mapping catheter includes both tracking coils 82c and sensing electrodes 180s. All of the catheters may also include at least one tracking coil 82c even if not shown in the example views.

The system 10 and/or circuit 60c can calculate the position of the tip of the device 80t as well as the shape and orientation of the flexible device based on a priori information on the dimensions and behavior of the device 80 (e.g., for a steerable device, the amount of curvature expected when a certain pull wire extension or retraction exists, distance to tip from different coils 82 and the like). Using the known information of the device 80 and because the tracking signals are spatially associated with the same X, Y, Z coordinate system as the MR image data, the circuit 60c can rapidly generate visualizations showing a physical representation of the location of a distal end portion of the device 80 with near RT MR images of the anatomy.

In some embodiments, the tracking signal data is obtained and the associated spatial coordinates are determined while a circuit 60c in the MRI Scanner 10S (FIG. 2) and/or in communication with the Scanner 10S (FIG. 3) obtains MR image data. The reverse operation can also be used. The circuit 60c can then rapidly render the resultant visualization(s) 100v (see, e.g., FIGS. 5A-5D) with the flexible device(s) 80 shown with a physical representation based on spatial coordinates of the devices in the 3-D imaging space identified using the associated tracking coil data and the near RT MR image(s).

As will be discussed further below, generally stated, in some embodiments, the circuit 60c can be configured to allow a user (via a User Interface 25 associated with a display, for example) to selectively show or not show (e.g., turn on/off and/or fade) in one or more visualizations on a display one or more of at least four different data sets in either the rendered model 100M or in near RT MRI images 100MRI of relevant scan planes during a procedure. The model 100M can be a planning model 37M or different patient model.

The different data sets can include a first data set associated with a volumetric model or map 100M of the patient (which may be shown in wire form), a second data set associated with tissue data maps 30 (e.g., tissue data based on image data such as edema, DHE and the like, and/or electroanatomical data), a third typically near-RT MRI scan (image) data set of relevant anatomic structure, and a fourth target site 55t data set. As will be discussed further below, a pre-acquired patient planning map can be used to identify at least one target site 55t and the planning map can be registered to the 3-D MRI image space which also registers the location of the target site in the 3-D space to allow the target site 55t to be shown in the visualizations in proper 3-D space location in either or both the near RT images or in the rendered registered model. The model 100M, the tissue data and the target sites (and the images 100MRI) can be turned "on" or "off" in the visualizations by a user and can be used to drive the MRI-guided procedure. For example, a "live" near RT MRI image of patient tissue can be shown in the visualization and a user (physician) can select to show at least one target treatment site in the image space in the near RT MRI image. The user may also show the model 100M in wire form with or without tissue data (e.g., DHE or edema map data). For example, as a therapeutic device/catheter 80 approaches a target site, the model 100M can be turned off or faded to a faint visibility with respect to near RT images can be shown. A user can also or alternatively select to show the target treatment sites 55t in the near RT images 100MRI without the model or with the model faded.

Figure 3:
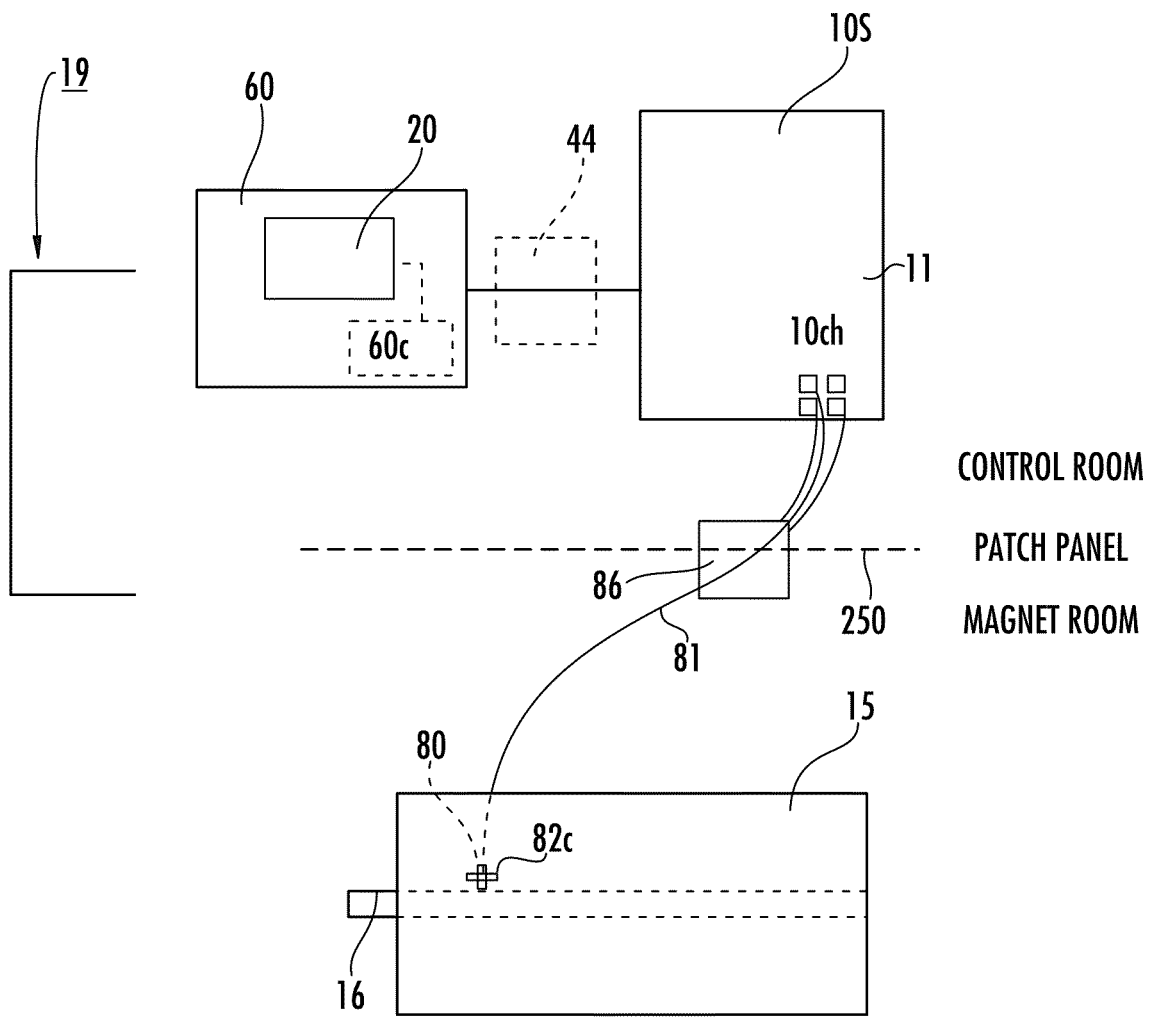
FIG. 3 is a schematic illustration of an MRI system with a workstation and display according to embodiments of the invention.

The circuit 60c can be totally integrated into the MR Scanner 10S (e.g., control cabinet), partially integrated into the MR Scanner 10S or be separate from the MR Scanner 10S but communicate therewith. If not totally integrated into the MR Scanner 10S, the circuit 60c may reside partially or totally in a workstation 60 and/or in remote or other local processor(s) and/or ASIC. FIG. 3 illustrates that a clinician workstation 60 can communicate with the MR Scanner 10S via an interface 44. Similarly, the device 80 in the magnet room can connect to the MR Scanner 10S via an interface box 86 which may optionally be integrated into the patch panel 250.

As shown in FIGS. 2 and 3, for example, the system 10 can include at least one (interactive) display 20 in communication with the circuit 60c and/or the Scanner 10S. The display 20 can be configured to display the interactive visualizations 100v. The visualizations 100v can be dynamic showing the movement of the device 80 relative to the intrabody anatomical structure shown by the displayed near-real time MRI image.

The system 10 can include a User Interface (UI) 25 with several UI controls 25c (FIG. 7), such as a graphic UI (GUI), in communication with the display 20 and may be configured to allow a user to select to show one or more pre-acquired or in situ generated maps and/or images 30 of target tissue including different tissue characterization maps and/or an optional EA map (or data from those maps) which can be shown in and/or with the visualization 100v. For example, the system 10 can be configured to allow a user to select to show a map (or data from the map) of patient vasculature and/or fibrous tissue based on pre-acquired image data (such as segmented MRA (Magnetic Resonance Angiography or other image slices) with the map or data therefrom being registered to and overlaid (superimposed) onto or incorporated into at least one of the models 100M or images 100MRI in the visualization and can be selectively turned on and off by a user. This information may help a clinician select a treatment site or avoid a treatment site or otherwise affect clinical choices. For example, for cardiac use, if vasculature with a relatively large blood flow is shown in a target lesion or injection space in cardiac tissue and/or if fibrous tissue is shown, a clinician may choose another spot or, where ablation is the therapy, may ablate longer to form a transmural lesion. Further examples of display options will be discussed further below.

In some embodiments, the system/circuit can employ interactive application of non-selective saturation to show the presence of a contrast agent in near real-time scanning. This option can help, for example, during image-guided catheter navigation to target tissue that borders scar regions. See, e.g., Dick et al., *Real Time MRI enables targeted injection of labeled stem cells to the border of recent porcine myocardial infarction based on functional and tissue characteristics*, Proc. Intl. Soc. Mag. Reson. Med. 11, p. 365

(2003); Guttman et al., *Imaging of Myocardial Infarction for Diagnosis and Intervention Using Real-Time Interactive MRI Without ECG-Gating or Breath-Holding*, Mag. Reson. Med, 52: 354-361 (2004), and Dick and Guttman et al., *Magnetic Resonance Fluoroscopy Allows Targeted Delivery of Mesenchymal Stem Cells to Infarct Borders in Swine*, Circulation, 2003; 108:2899-2904, which describe, inter alia, imaging techniques used to show regions of delayed enhancement in (near) real-time scans. The contents of these documents are hereby incorporated by reference as if recited in full herein.

FIG. 2 illustrates that the device 80 can include at least one conductor 81, such as a coaxial cable, that connects a respective tracking coil 82c to a channel 10ch of the MR Scanner 10S. The MR Scanner 10S can include at least 16 separate channels, and typically more channels but may operate with less as well. Each device 80 can include between about 1-10 tracking coils, typically between about 2-6. The coils 82c on a particular device 80 can be arranged with different numbers of turns, different dimensional spacing between adjacent coils 82c (where more than one coil is used) and/or other configurations. The circuit 60c can be configured to generate the device renderings based on tracking coil locations/positions relative to one another on a known device with a known shape and/or geometry or predictable or known changeable (deflectable) shape or form (e.g., deflectable end portion). The circuit can identify or calculate the actual shape and orientation of the device for the renderings based on data from a CAD (computer aided design) model of the physical device. The circuit can include data regarding known or predictable shape behavior based on forces applied to the device by the body or by internal or external components and/or based on the positions of the different tracking coils in 3-D image space and known relative (dimensional) spacing.

As shown in FIG. 3, the display 20 can be provided in or associated with a clinician workstation 60 in communication with an MRI Scanner 10. Other displays may be provided. The MRI Scanner 10S typically includes a magnet 15 in a shielded room and a control cabinet 11 (and other components) in a control room in communication with electronics in the magnet room. The MRI Scanner 10S can be any MRI Scanner as is well known to those of skill in the art. Examples of current commercial scanners include: GE Healthcare: Signa 1.5 T/3.0 T; Philips Medical Systems Achieva 1.5 T/3.0 T; Integra 1.5 T; Siemens: MAGNETOM Avanto; MAGNETOM Espree; MAGNETOM Symphony; MAGNETOM Trio; and MAGNETOM Berio.

Figure 4:
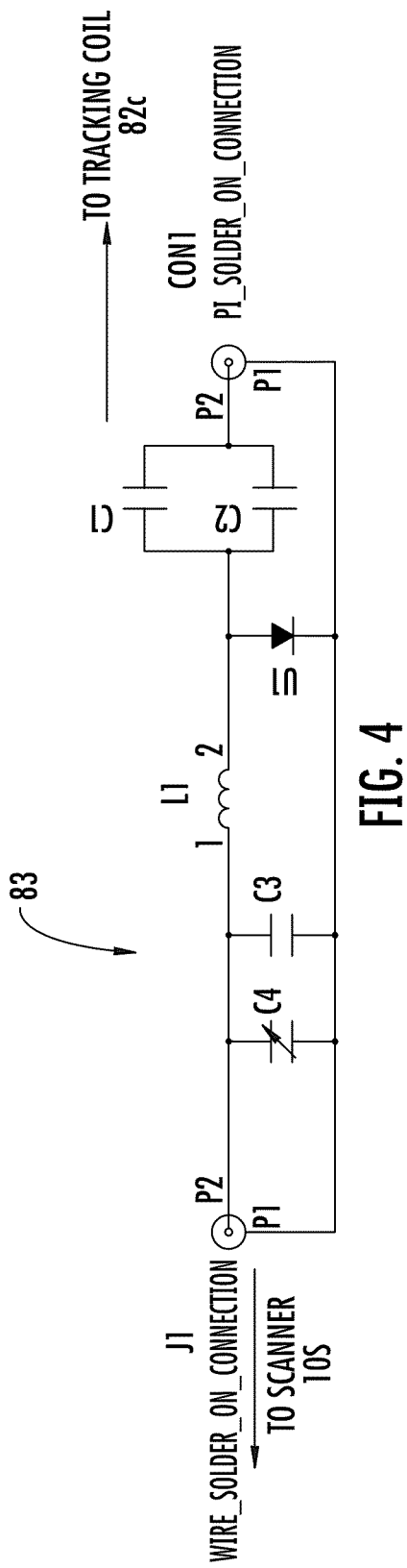
FIG. 4 is a circuit diagram of an exemplary tracking coil tuning circuit according to embodiments of the present invention.

The tracking coils 82c can each include a tuning circuit that can help stabilize the tracking signal for faster system identification of spatial coordinates. FIG. 4 illustrates an example of a tuning circuit 83 that may be particularly suitable for a tracking coil 82c on a catheter. As shown, CON1 connects the coaxial cable to the tracking coil 82c on a distal end portion of the device 80 while J1 connects to the MR Scanner channel 10ch. The Scanner 10S sends a DC bias to the circuit 83 and turns U1 diode "ON" to create an electrical short which creates a high impedance (open circuit) on the tracking coil to prevent current flow on the tracking coil and/or better tracking signal (stability). The tuning circuit can be configured to have a 50 Ohm matching circuit (narrow band to Scanner frequency) to electrically connect the cable to the respective MR Scanner channel. When the diode U1 is open, the tracking coil data can be transmitted to the MR Scanner receiver channel 10ch. The C1 and C2 capacitors are large DC blocking capacitors. C4 is optional but can allow for fine tuning (typically between about 2-12 picofarads) to account for variability (tolerance) in components. It is contemplated that other tuning circuits and/or tracking signal stabilizer configurations can be used. The tuning circuit 83 can reside in the intrabody device 80 (such as in a handle or external portion), in a connector that connects the coil 82c to the respective MRI scanner channel 10ch, in the Scanner 10S, in an interface box 86 (FIG. 2), a patch panel 250 and/or the circuit 83 can be distributed among two or more of these or other components. Where multiple devices 80 are tracked concurrently (and rendered and shown in the visualizations), the circuit 60c can correlate the respective tracking coils to the corresponding device and identify the different devices. Typically, the device identifiers are "unique" electronic identifiers with pre-defined values such as different resistance values.

In some embodiments, each tracking coil 82c can be connected to a coaxial cable 81 having a length to the diode via a proximal circuit board (which can hold the tuning circuit and/or a decoupling/matching circuit) sufficient to define a defined odd harmonic/multiple of a quarter wavelength at the operational frequency of the MRI Scanner 10S, e.g., $\lambda/4$, $3\lambda/4$, $5\lambda/4$, $7\lambda/4$ at about 123.3 MHz for a 3.0 T MRI Scanner. This length may also help stabilize the tracking signal for more precise and speedy localization. The tuned RF coils can provide stable tracking signals for precise localization, typically within about 1 mm or less. Where a plurality (e.g., two closely spaced) adjacent tracking coils are fixed on a substantially rigid material, the tuned RF tracking coils 82 can provide a substantially constant spatial difference with respect to the corresponding tracking position signals.

The tracking sequence used in the system 10 can intentionally dephase signal perpendicular to the read-out direction to attenuate unwanted signal from 1) bulk objects and 2) regions sensed by other signal sensitive parts of the catheter which couple to the tracking coil 82c (e.g. the coaxial cable along the catheter shaft). This tends to leave only a sharp peak indicating the position of the tracking coil.

The tracking sequence block can include or consist of a plurality of (typically about three) repetitions of a small flip-angle excitation. Each repetition is designed to indicate the x, y or z component of the tracking coil coordinates in succession. Frequency encoding is used along the x-direction to obtain the x-coordinate, the y-direction for the y-coordinate, and the z-direction for the z-coordinate. When the frequency encoding is in the x-direction, the other two directions (y and z) are not spatially encoded, producing projection (spatially integrated) signals in those directions from all excitation regions. The dephasing gradient attempts to attenuate unwanted signal included in these projections. Once the tracking sequence block is complete, a spoiler gradient can be used to dephase any transverse signal remaining from the tracking before the imaging sequence block is executed.

The imaging sequence block obtains a portion, depending on the acceleration rate, of the data used to reconstruct an image of a single slice. If the acceleration rate is 1, then all of the data for an image is collected. If the acceleration rate is 2, then half is collected, etc. If multiple slices are activated, then each successive imaging block collects data for the next slice, in 'round robin' fashion. If any magnetization preparation (e.g., saturation pulses) is activated, these are executed after the tracking sequence block, immediately before the imaging sequence block.

Additional discussion of tracking means and ablation catheters can be found in U.S. Pat. No. 6,701,176, and U.S. Provisional Application Ser. No. 61/261,103, the contents of which are hereby incorporated by reference as if recited in full herein. Exemplary ablation catheters will be discussed further below.

Referring now to FIGS. 5A-5D and 6, examples of visualizations 100v with a physical representation 80R of the intrabody device 80, a volumetric model 100M of target anatomical structure and near real-time MRI images 100MRI. The circuit 60c/Scanner 10S is configured to present a 3-D volumetric model of at least a portion of the patient's target anatomy (shown as the heart) 100M in the visualization 100v with the model registered to the 3-D imaging space along with a physical representation of at least the distal end portion of the at least one intrabody device 80R in the imaging space. Optionally, the visualizations can be carried out to show the tracking coils in the physical representation of the distal end portion of the medical device in different colors using the identified location of the tracking coils and defined form factor and/or dimensional data regarding actual coil placement on the device.

The circuit 60c can be configured to generate the visualizations 100v with at least two visual reference planes 41, 42 (shown with a third intersecting plane 43) that are typically oblique or orthogonal to each other and extend through at least a major portion of the visualization 100v. The planes 41, 42 (and 43) can be transparent and/or translucent. They may be shown with different color perimeters that correspond to a respective two-dimensional image slice (which may be shown as thumbnails on the display also with a perimeter of similar or the same color).

The planes 41, 42 can move relative to each other in the imaging space or may be locked together, in any case they can be configured to move relative to the model 100M in the imaging space. As shown in FIGS. 5A-5D, a user can rotate and zoom the visualization 100v which automatically adjusts the visualization shown on the display. As also shown, the flexible device 80 is not required to be in any of the relevant anatomical scan planes used to obtain MR data for the at least one near RT MRI image 100MRI in the visualization and the distal end portion 80d of the flexible device 80 can take on a curvilinear shape and the tip 80t can be steered or guided into different target positions.

Figure 5A:
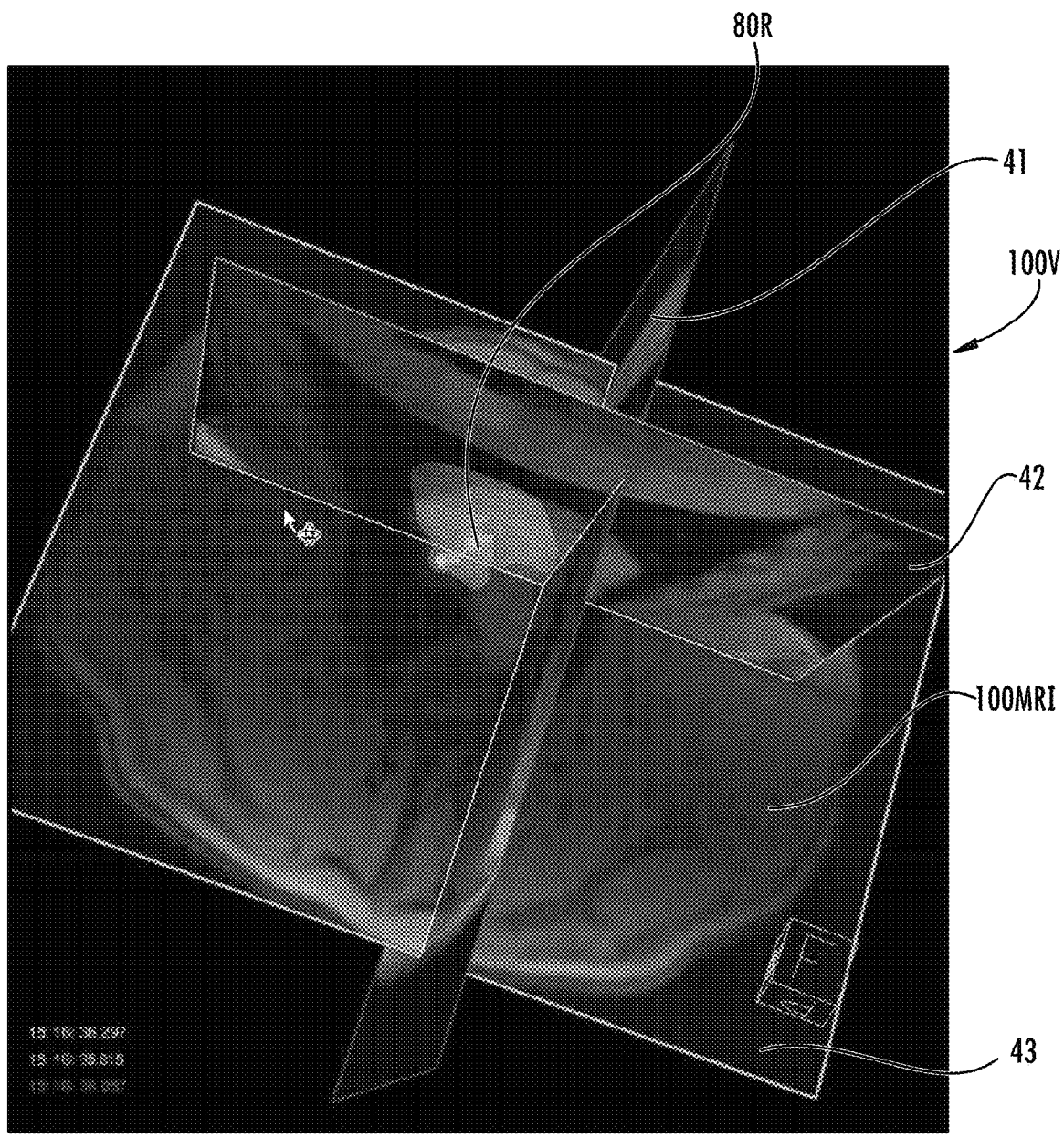
FIGS. 5A-5D are contemplated screen shots of exemplary interactive visualizations with a physical representation of an intrabody flexible medical device according to embodiments of the present invention.
Figure 5B:
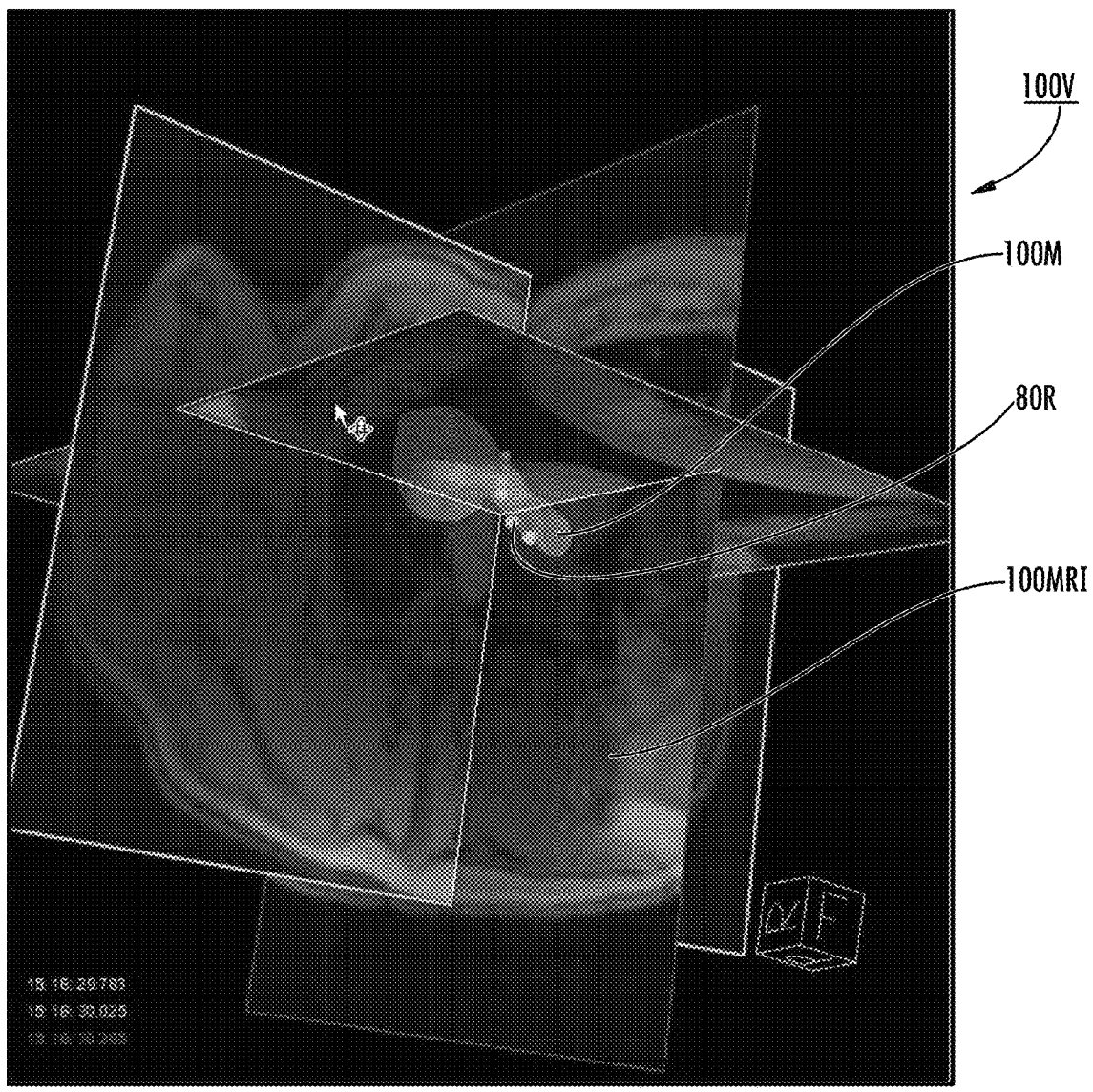
Figure 5C:
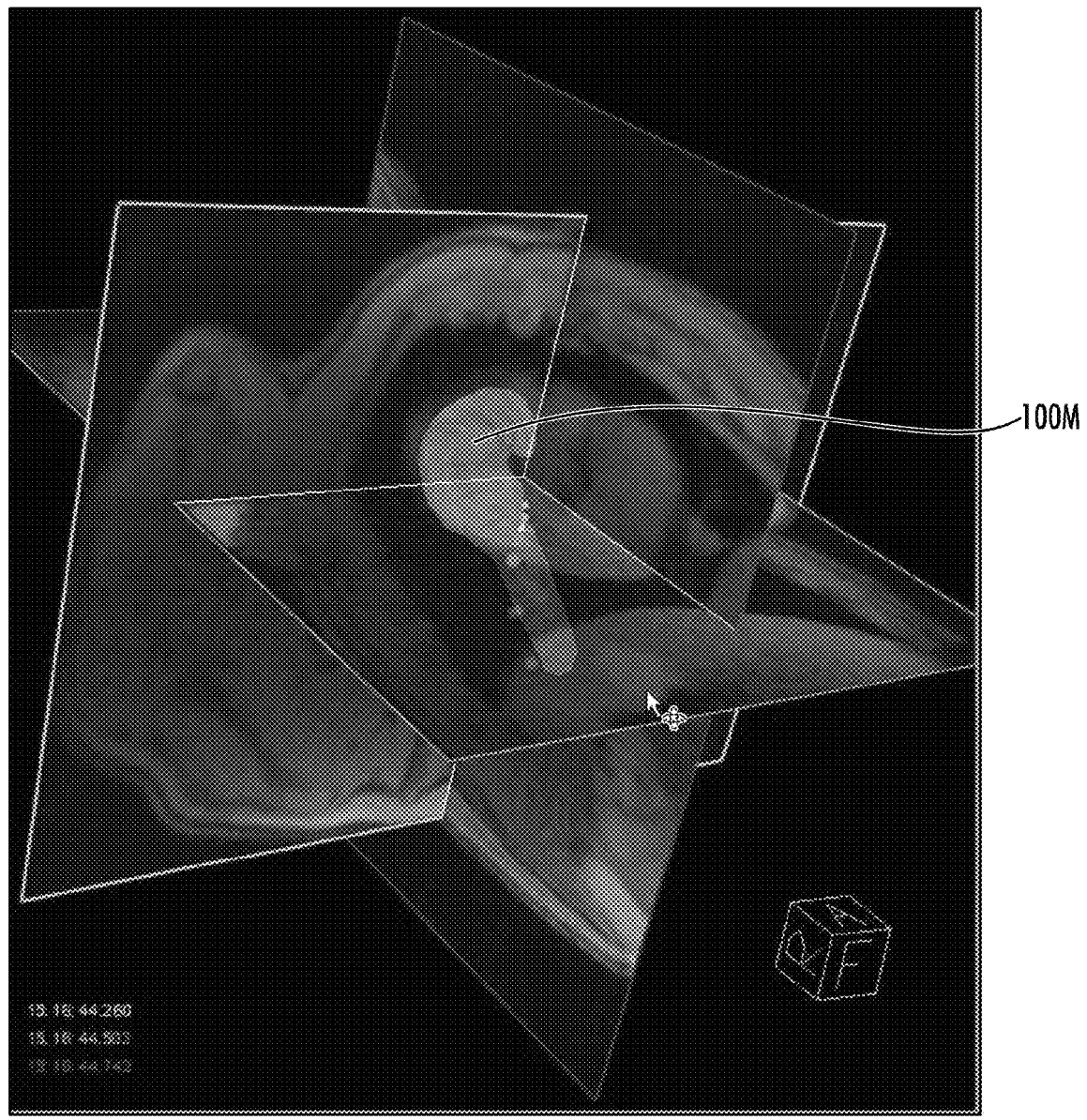
Figure 5D:
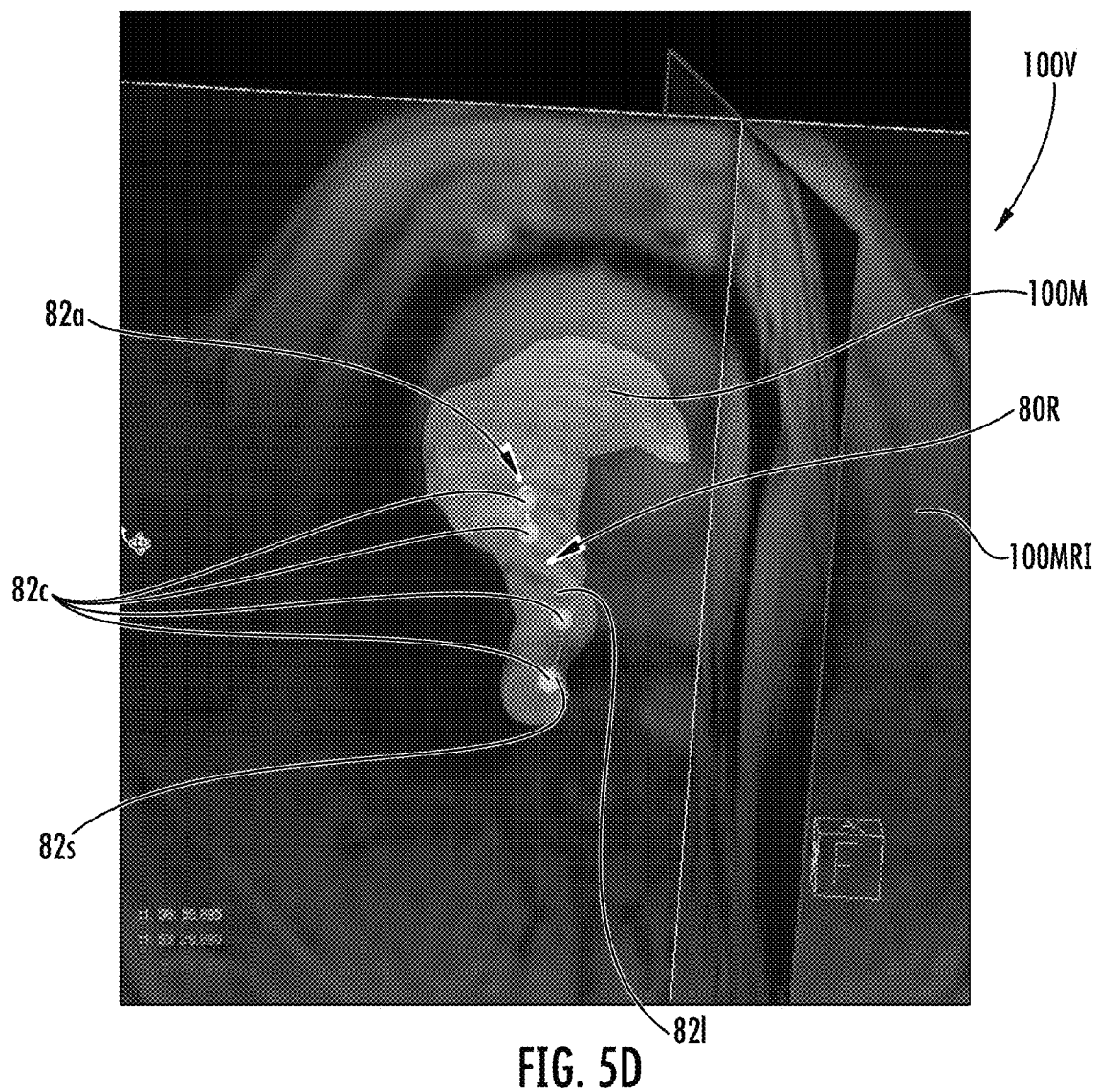

In some embodiments, as shown in FIG. 5D, the circuit 60c is configured to associate a tip location of the at least one device 80 with an arrow 82a and render the visualization so that each tracking coil 82 on the distal end portion 80d has a shape 82s with a color, with each tracking coil 82 having a respective different color from the other tracking coils, and with a line or spline 82l connecting the tip 82a and the coils 82c and the line 82l is able to flex, bend and move to reflect movement of the device 80 in the visualizations 100v. The system/circuit can be configured to display color-highlighted images generated using tracking coil data from the MR Scanner tracking coil channels so as to display the coils as color high-lighted features in the 3D rendering of the physical representation of the device (e.g., catheter).

Figure 6:
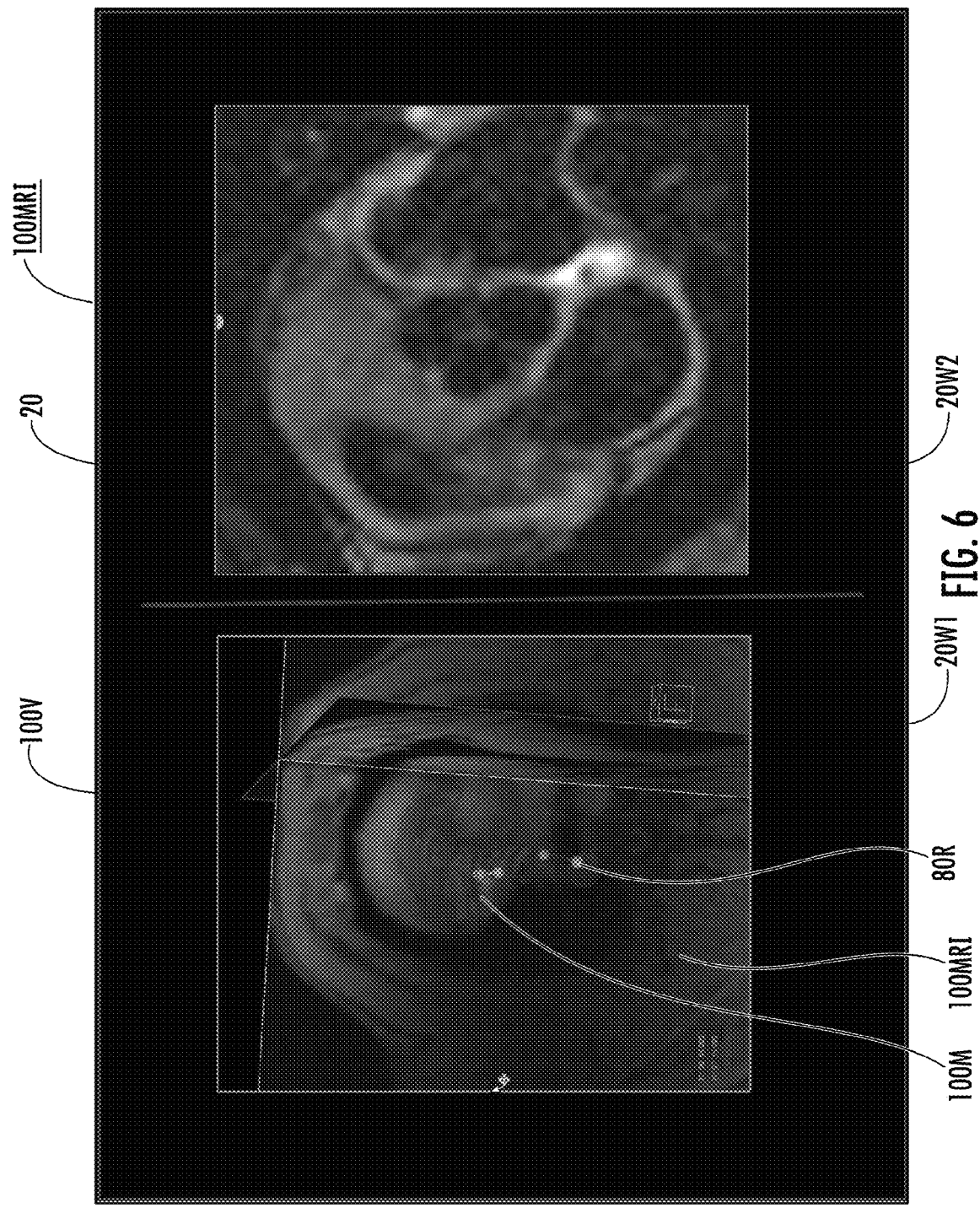
FIG. 6 is a schematic illustration of a display with two viewing windows, one showing an interactive visualization and the other showing relevant near RT MRI image according to embodiments of the present invention.

FIG. 6 illustrates that the system 10 can be configured to show both the interactive visualization 100v in one viewing window $20w_1$ and an MRI image 100MRI alone in a second viewing window $20w_2$. The MRI image 100MRI in the second window $20w_2$ is typically associated with the target anatomy location identified by a user in the interactive visualization 100v in the first viewing window $20w_1$.

Figure 7:
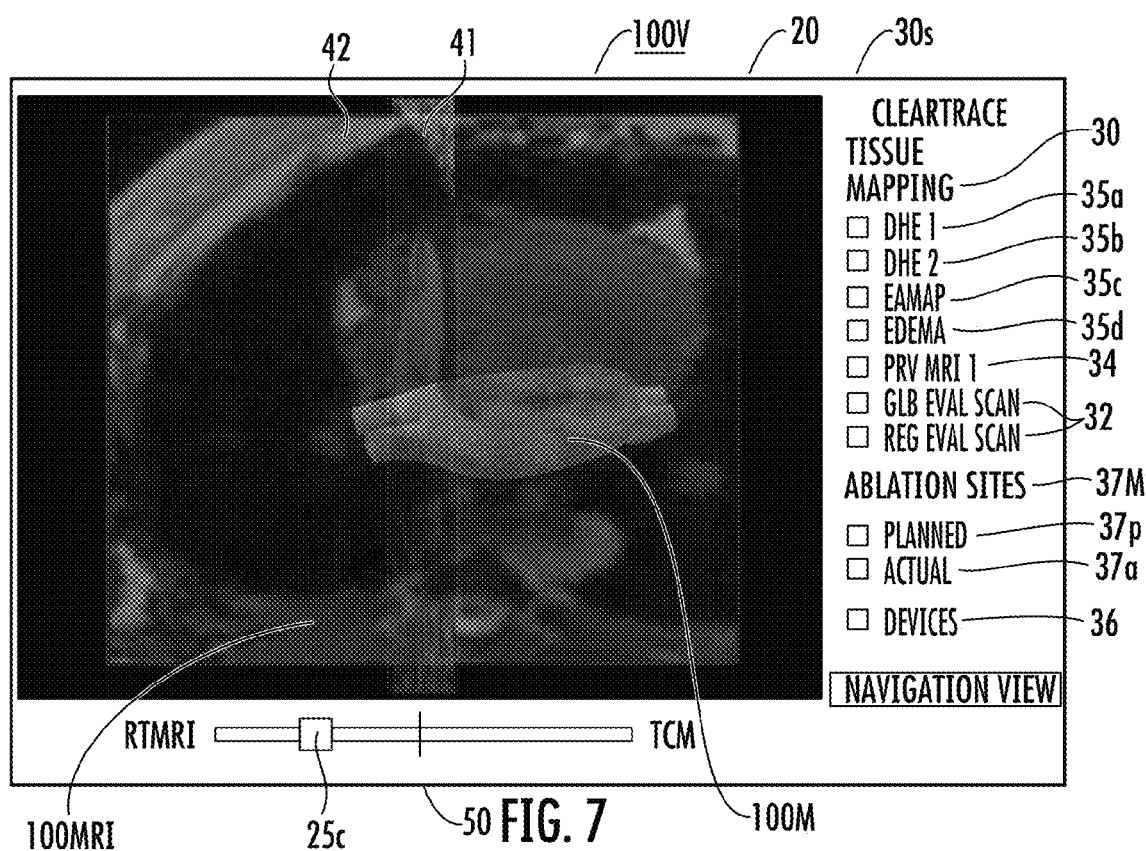
FIGS. 7-21 are contemplated screen shots of exemplary visualizations and images on a display and UI controls that can be generated to facilitate an MRI guided procedure according to embodiments of the present invention.

As shown in FIG. 7, the display 20 can have a UI 25 can be configured to allow a physician or other clinician to select whether to show near real time MR images of target tissue 100MRI either with a model 100M of the target anatomical structure (FIG. 7) and/or in a separate viewing window (FIGS. 6, 13-16). The circuit 60 is in communication with at least one display 20 with the User Interface 25.

Figure 9:
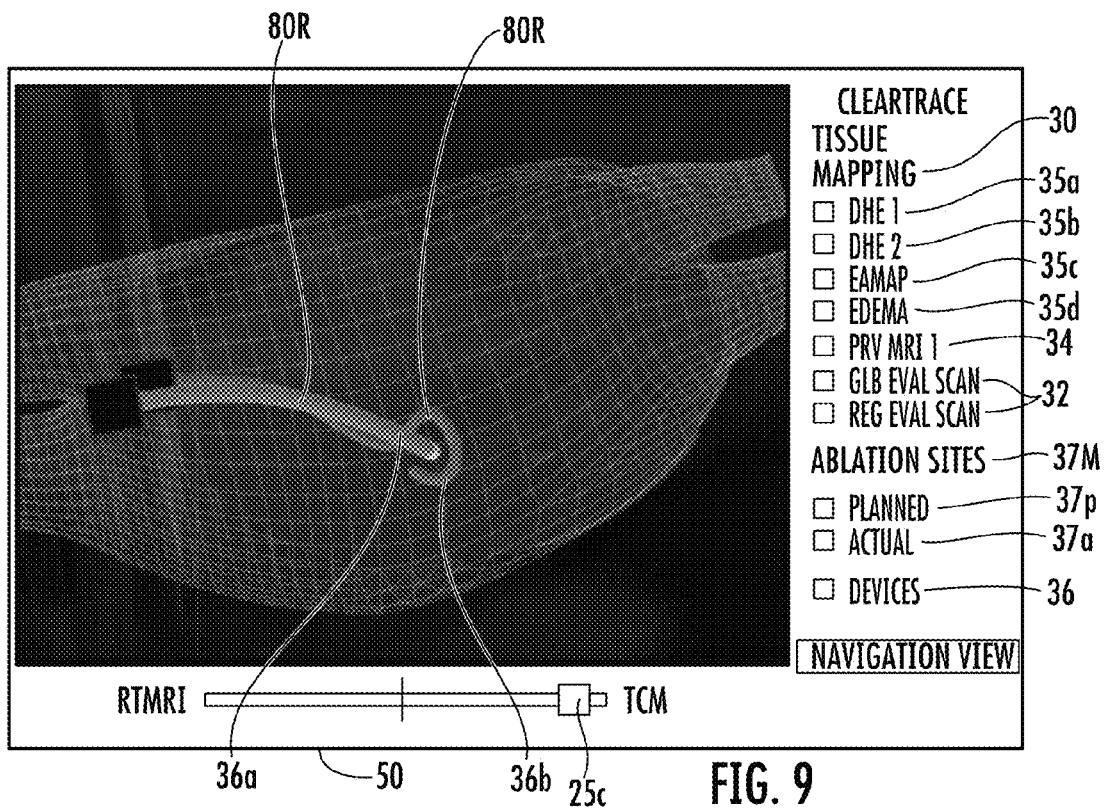

The User Interface 25 can be configured to allow a user to alter the displayed visualization (fade) to include only a near RT image of the anatomy, to include the near RT image of the anatomy and the registered model of the heart, or to include only the registered model, see, for example, FIG. 7 showing both types of images in the visualization 100v with FIG. 9 which shows only the model 100M. The UI 25 can be an on/off selection of these options or may "fade" from one viewing option to another. As shown, a virtual sliding control 25c allows a user to change what is shown ((near) RTMRI 100MRI to only the Model 100M).

The circuit 60c can also be configured to generate MRI images which show the device location in near real time (in the MR image space). The UI 25 can also be configured to allow a user to turn off and/or fade the renderings of the device 80 in and out of the visualizations with rendered views of the device versus actual images of the device to confirm location or for additional visual input. The device may include other fiducial markers (e.g., a passive marker or an active marker such as receive antenna) for facilitating the visual recognition in the MR image.

The UI 25 typically includes multiple GUI controls that can include a touch screen input control to allow a clinician/physician to select a region of interest in the map 100M by placing a cursor or by touching the screen at a region of interest. This can cause the system to obtain real time MR image data of that region and provide the associated image on the display and/or define scan planes (which may be preset scan planes) at that location in space.

Referring again to FIG. 7, for example, the display 20 can be in communication with a UI 25 that provides a plurality of user selectable different maps 30 so that the map or data therefrom can be "turned on and off" on the displayed 3-D anatomical map registered to the imaging space. The different maps can comprise a patient-specific 3-D (volumetric) anatomical map, and/or data that can be shown on the 3-D anatomical map, obtained in or registered to the MRI 3-D imaging space used during the MR guided procedure. For tissue characterization maps, the maps include spatially correlated tissue characterization data taken from MR image data incorporated therein as discussed above. The UI 25 can include multiple different GUI (Graphic User Input) controls 25c for different functions and/or actions. The GUI controls 25c may also be a toggle, a touch screen with direction sensitivity to pull in one direction or other graphic or physical inputs.

Figure 17:
Figure 19:
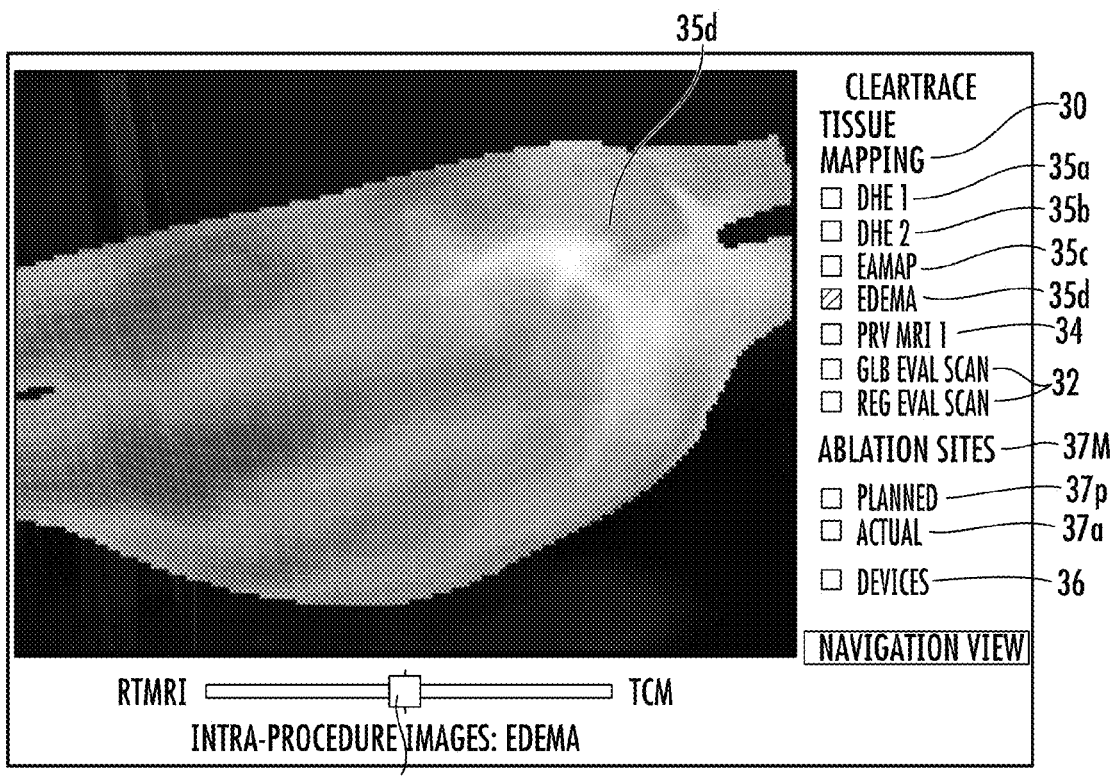
Figure 27:
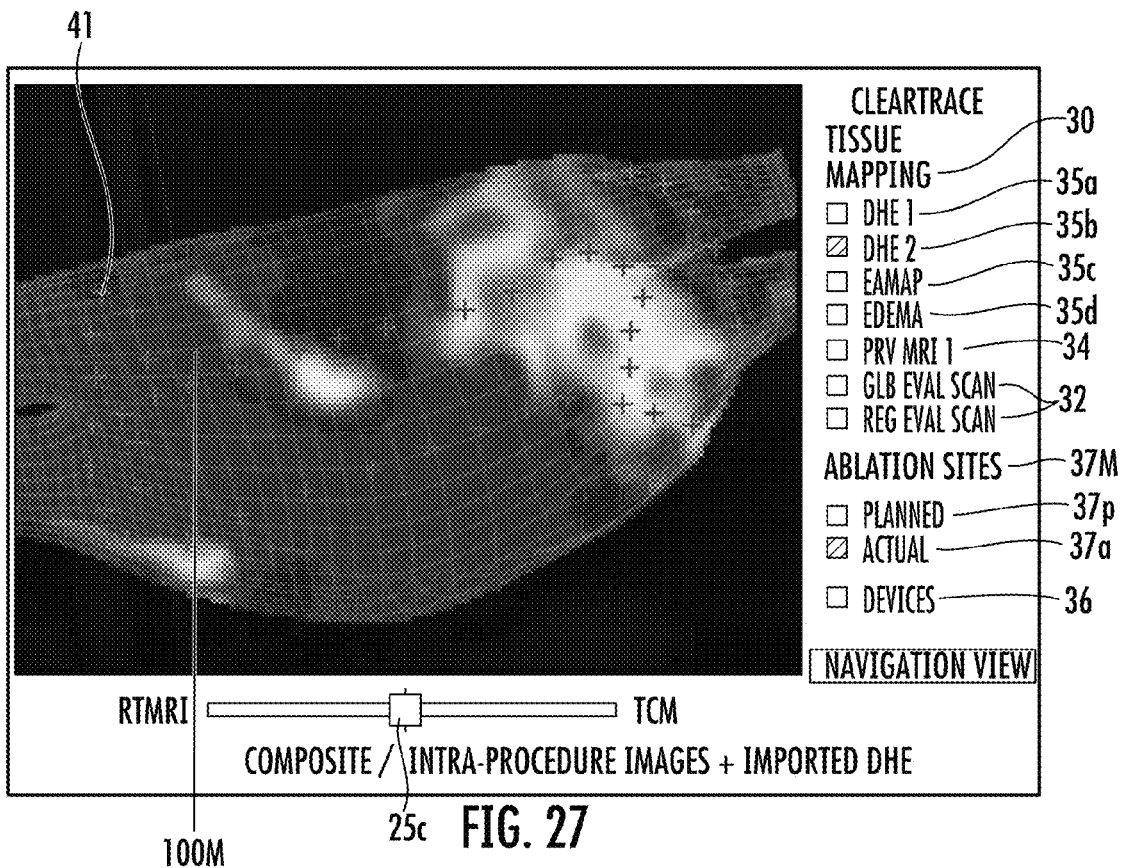
Figure 28:
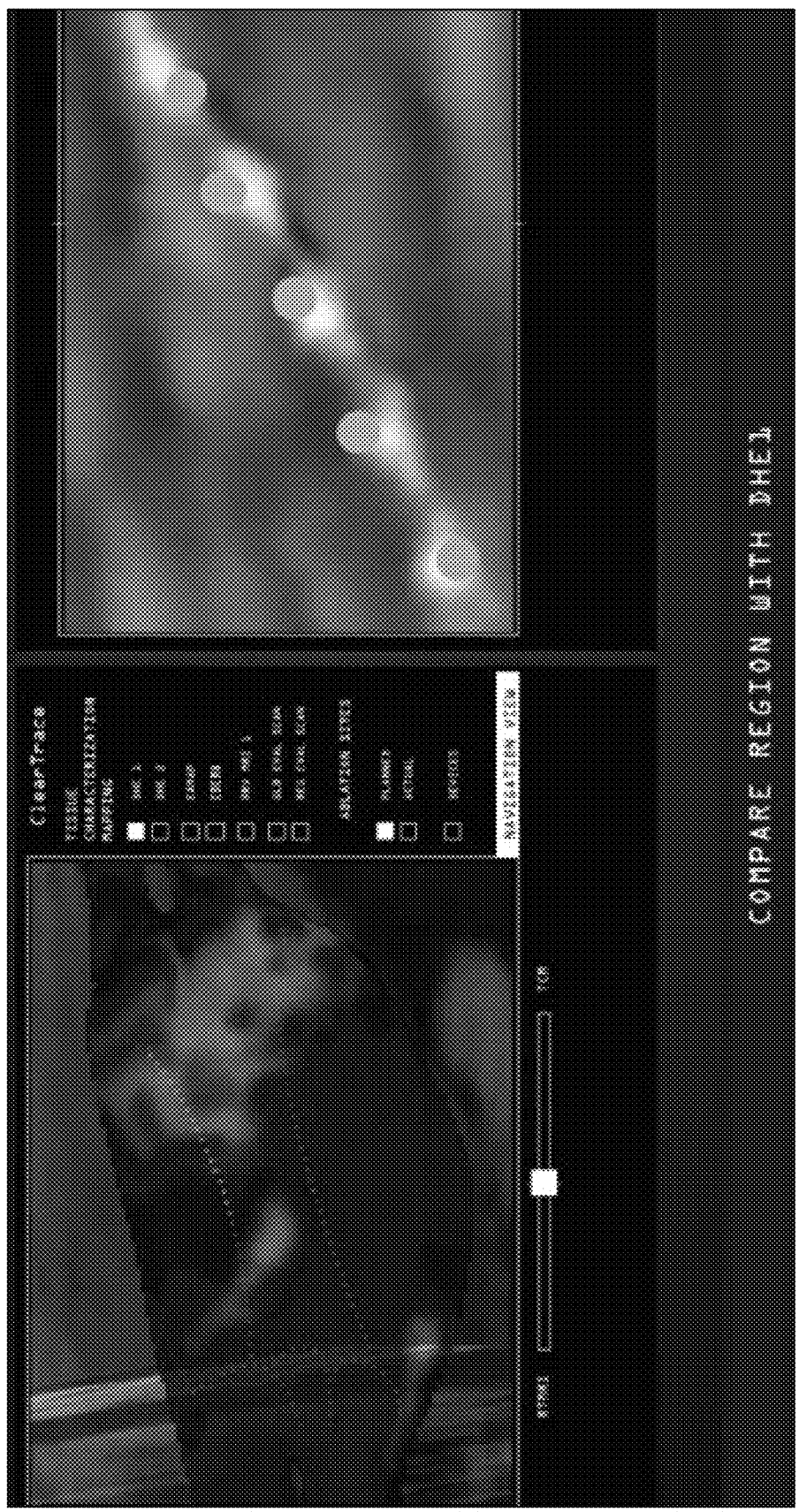

The user selectable patient-specific maps 30 including a plurality of tissue maps, typically including at least one, and more typically several types of, tissue characterization maps (or data associated with such maps to be shown (superimposed) on a registered anatomic model) associated with the procedure that can be selected for viewing by a user. The UI 25 can also include GUI controls that allow a user to select two or more of the tissue maps, with such data able to be shown together (overlaid and registered and/or as a composite image/map) or separately. As shown, the maps 30 and/or data therefrom, may include at least a plurality of the following:

(a) a regional evaluation scan map 32r (FIG. 17) and/or a global evaluation scan map 32g (FIG. 13) which shows tissue information, e.g., actual lesion patterns in one region to allow a clinician to view regional ablation information (such as at the LA (left atrium), a PV (pulmonary vein) and the like);

(b) pre-procedure MRI cardiac scans 34;
(c) DHE 1 (Delayed Hyper Enhancement) tissue characterization map 35a taken at a first point in time (such as a week or just prior to the procedure) (FIG. 28);
(d) DHE 2 tissue characterization map 35b taken at a second point in time, such as during a procedure, potentially toward an end of the procedure (for cardiac ablation procedures that can be used to confirm complete electrical isolation of the PV (pulmonary veins) or other targets prior to terminating the procedure—alternatively the DHE 2 map can be associated with the end of a prior EP ablation procedure) (FIG. 27);
(e) an EA (electroanatomical) map 35c (FIG. 17);
(f) an edema tissue characterization map 35d (FIG. 19);
(g) other tissue characterization maps 35e, for example:
  (i) a composite thermal tissue characterization map that shows positions of increased temperature that were caused by ablation of tissue during the procedure;
  (ii) ischemic (oxygen deprived or lacking) tissue characterization map;
  (iii) hypoxic or necrotic tissue characterization map;
  (iv) fibrous tissue map;
  (v) vasculature map;
  (vi) cancer cell/tissue map (where cancer is the condition being treated);
  (vii) a fluid distribution map (for visualizing injected or otherwise delivered therapeutic fluid in local tissue of the target anatomical structure);
  (viii) light exposure maps;
(h) at least one procedure planning map 37M with one or more target sites 37p (also referred to interchangeably herein as sites 55t) and a later tissue map showing actual sites 37a (e.g., target and actual ablation sites) shown in different colors, opacities and/or intensities for ease of reference (see, e.g., FIG. 10, red/darker spots associated with target and green or lighter spots associated with actual); and
(i) device views 36 that show the physical representation of the device 80 in the surgical/imaging space, e.g., with an ablation catheter 36a shown in position and/or a mapping (loop) catheter 36b as devices 80 shown in position (FIGS. 9, 11). These device maps 36 may be used/displayed, for example, during a navigation mode. The default action may be to show these devices at least in the navigation mode but a user can deselect this choice. The devices may also be "turned" off or faded or shown in wire grid or otherwise in the visualizations subject typically to user input.

The tissue maps 30 (or associated tissue data) are typically registered to the 3-D coordinate MRI image space (manually or via automatic electronic image alignment registration means) or obtained during the procedure so that the MR image data is in the 3-D MRI image space. In some embodiments, relevant image scan planes and MR image data of the patient can be imported and/or incorporated into one or more of the tissue maps so that the map(s) can be updated over time (including in real time) using MR image data correlated with the anatomical location on the (updated) tissue map 30 automatically or upon request by a user. EA maps can be generated using tracking and/or mapping catheters in the 3-D MRI image space which may provide a more accurate or timely EA map (without requiring registration of a pre-acquired map).

The tissue map(s) 30 can be generated using MR image data that shows normal and abnormal status, conditions and/or behavior of tissue or status of tissue in response to a treatment. For example, a tissue characterization map(s) can show a thermal profile in different colors (or gray scale) of cardiac tissue in a region of interest and/or globally. In other embodiments, a tissue characterization map can illustrate one or more of infarct tissue, other injured tissue such as necrotic or scar tissue, hypoxic, ischemic, edemic (e.g., having edema) and/or fibrotic tissue or otherwise impaired, degraded or abnormal tissue as well as normal tissue on an anatomical model of the heart. In yet other embodiments, the tissue maps can illustrate portions of the heart (e.g., LA or posterior wall) with lesser or greater wall motion, and the like.

In some embodiments, the system can be used to deliver a therapeutic to target anatomy using an injection needle or fluid delivery cannula. A fluid distribution map or data therefrom can be shown on the model 100M or in the MRI image 100MRI (without requiring the rendered model). For example, to treat heart failure, a therapeutic agent can be injected into one or more target locations in infarct or abnormal cardiac tissue. Typically, the injection is carried out in several spots to generate a desired coverage pattern or area/volume. The fluid distribution map can be used to confirm that desired coverage of the cardiac tissue was obtained based on the injections. If not, another ("clean-up") target site or sites can be identified and the sites can be injected with the therapeutic agent. In other embodiments, a previous injection site may need additional volumes of the agent, so that same site can be treated again. The fluid distribution map can be generated based on MRI image data alone. In other embodiments, a fluid distribution map can be generated based on a known injection site or sites, and a known volume of injected agent (which may be measured in situ or based on a known flow rate and known time of injection). This data can be used to generate an estimated fluid distribution map. In other embodiments, a fluid distribution map can be generated based on both MR image data and injection amounts. In some embodiments, the system/circuit 60c can identify a spatial grouping of injection sites and electronically select a scan plane or scan planes that can be set through the injection sites to obtain near RT MRI image data or obtain image data after the injections (such as for a regional or global coverage evaluation prior to the end of the MRI-guided procedure). For cardiac injections for some heart repairs, a planning map 37M identifying infarct tissue and normal (healthy) tissue boundaries can be used to identify target injection sites 55t. This map 37M can be registered to the MRI image space. A target site 55t can be associated with the X, Y, Z location in the MRI image space. Near RT images 100MRI can be generated during the injections (similar to the ablations) to allow a physician to see "live" the injection distribution or disbursement. This fluid distribution map can be electronically provided as a data set that can be selectively shown on the anatomical model 100M. The therapeutic agent can be any suitable agent including, for example, stem cells (and may be directed to rebuilding cardiac tissue) and is MRI visible.

Other embodiments can generate light exposure maps to evaluate optical light exposure of target tissue (or light activated drugs in such tissue) similar to the fluid distribution map discussed above. The light exposure map can be based on an internal laser or other light source that exposes the tissue to non-ablative energy.

Whether a parameter or tissue characteristic is shown in a respective tissue map 30 as being impaired, degraded or otherwise abnormal or affected by a therapy versus normal or untreated can be based on the intensity of pixels of the tissue characteristic in the patient itself or based on predefined values or ranges of values associated with a population "norm" of typical normal and/or abnormal values, or combinations of the above.

Thus, for example, normal wall motion can be identified based on a comparison to defined population norms and different deviations from that normal wall motion can be shown as severe, moderate or minimal in different colors relative to tissue with normal wall motion.

In another example, a thermal tissue characterization map 30 can illustrate tissue having increased temperatures relative to other adjacent or non-adjacent tissue. Thus, for example, during or shortly after ablation, the lesioned tissue and tissue proximate thereto can have increased temperatures relative to the non-lesioned temperature or tissue at normal body temperatures. Areas or volumes with increased intensity and/or intensity levels above a defined level can be identified as tissue that has been ablated. The different ablation sites 55t can be shown on the map 30 as areas with increased temperatures (obtained at different times during the procedure) and incorporated into the thermal tissue characterization map 30 automatically and/or shown upon request.

In some embodiments, the tissue characteristic map 30 uses MR image data acquired in association with the uptake and retention of a (e.g., T-1 shortening) contrast agent. Typically, a longer retention in tissue is associated with unhealthy tissue (such as infarct tissue, necrotic tissue, scarred tissue and the like) and is visually detectable by a difference in image intensity in the MR image data, e.g., e.g. using a T1 weighted sequence, to show the difference in retention of one or more contrast agents. This is referred to as delayed enhancement (DE), delayed hyper-enhancement (DHE) or late gadolinium enhancement (LGE). As discussed above, in some embodiments, the system/circuit can employ interactive application of non-selective saturation to show the presence of a contrast agent in near real-time scanning. This option can help, for example, during image-guided catheter navigation to target tissue that borders scar regions. Thus, the DHE image data in a DHE tissue characterization map can be pre-acquired and/or may include near-RT image data.

The tissue map is typically a volumetric, 3-D or 4-D anatomical map that illustrates or shows tissue characterization properties associated with the volume as discussed above. The map can be in color and color-coded to provide an easy to understand map or image with different tissue characterizations shown in different colors and/or with different degrees of a particular characterization shown in gray scale or color coded. The term "color-coded" means that certain features or conditions are shown with colors of different color, hue or opacity and/or intensity to visually accentuate different conditions or status of tissue or different and similar tissue, such as, for example to show fluid distribution from an injected therapeutic or lesions in tissue versus normal or non-lesion or non-injected/affected tissue.

In some embodiments, the UI 25 can be configured to allow a clinician to increase or decrease the intensity or change a color of certain tissue characterization types, e.g., to show lesion tissue or tissue having edema with a different viewing parameter, e.g., in high-contrast color and/or intensity, darker opacity or the like. A treatment site, such as a lesion site(s) in/on the tissue characterization map 30 can be defined based on a position in three-dimensional space (e.g., where an electrode is located based on location detectors, such as tracking coils, when the ablation electrode is activated to ablate), but is typically also or alternately associated with MRI image data in associated scan planes to show an ablation site(s) in an MRI image. The MR image data may also reflect a change in a tissue property after or during ablation during the procedure, e.g., DHE, thermal, edema and the like.

The circuit 60c can be configured to generate a tissue map 37M (FIG. 27) that is a difference or a comparison map that is generated from a pre-procedure or start-of procedure tissue data and an intra-procedure tissue data to show the differences based on the procedure. The "before" and "after" maps can be electronically overlaid on a display and shown in different colors, opacities and/or intensities or corresponding pixel values from each image in a region of interest (ROI) can be subtracted to show a difference map or otherwise integrated into a composite map. Again, the UI 25 can allow a clinician to select or deselect (or toggle between) the before or after tissue characterization maps or adjust display preferences to allow a visual review of differences.

A regional update tissue map 32 can be used to evaluate whether target or actual treatment sites have been successfully treated, e.g., whether ablated locations have the desired transmural lesion formation. For example, the UI 25 can allow the clinician to select a high resolution or enlarged view of the actual ablated tissue merely by indicating on the interactive map 100M, such as a regional evaluation tissue map, a desired region of interest (e.g., by pointing a finger, cursor or otherwise selecting a spot on the display). For example, a high resolution MR image of suspect tissue in the LSPV can be shown so that the physician can see actual tissue in the desired spot indicated on the tissue characterization map. New targets can be electronically marked on the map as needed and scan planes can be automatically electronically be selected, identified or otherwise associated with the new target location.

Figure 13:
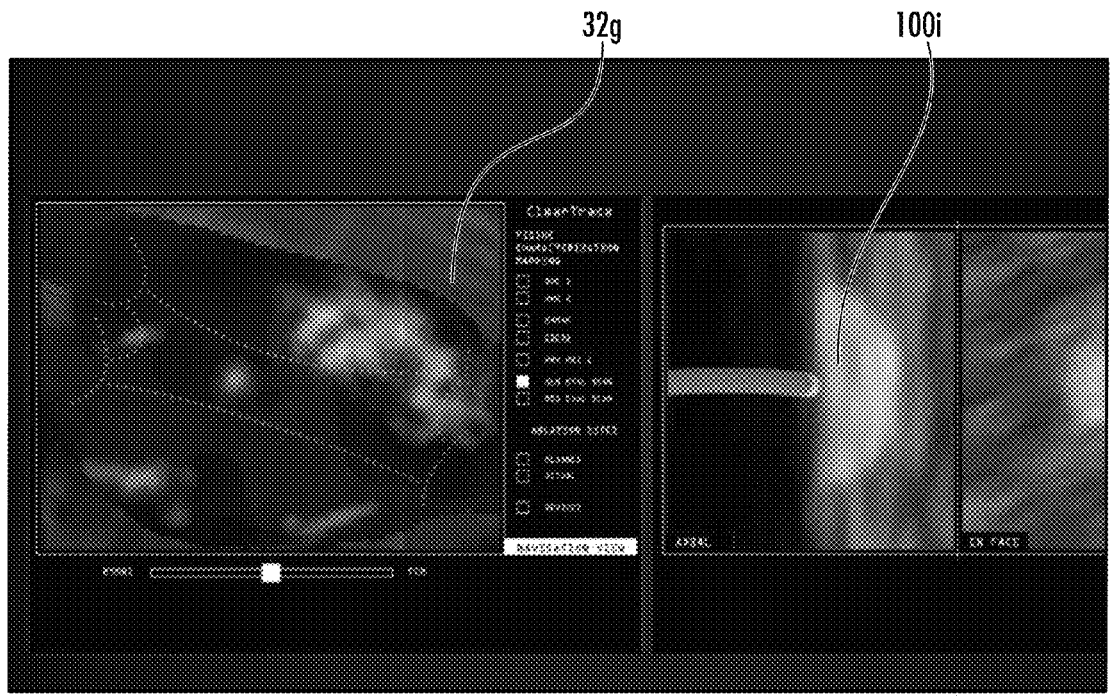

FIG. 13 shows the display 20 with side-by-side viewing windows, one window showing the visualization with the map 100M (which may be a tissue characterization map) and the other window with at least one near RT MRI image of local tissue during an active treatment mode.

Figure 22A:
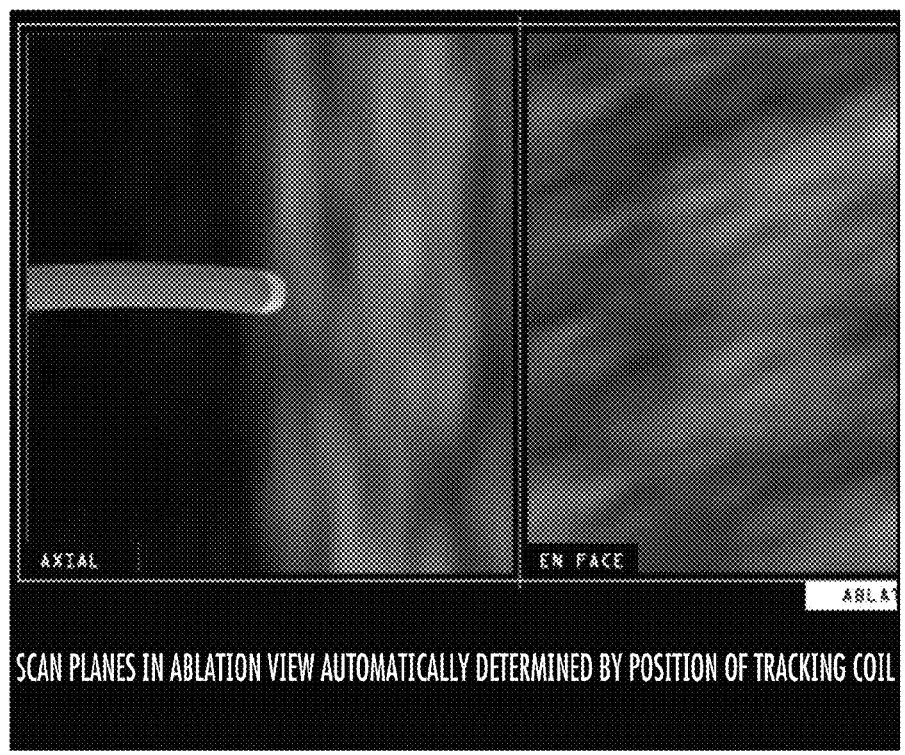
FIGS. 22A and 22B are exemplary (contemplated) screen shots of an intrabody device (e.g., ablation catheter) with the device rendered as a physical representation and the MRI image being in close-up according to embodiments of the present invention.
Figure 22B:
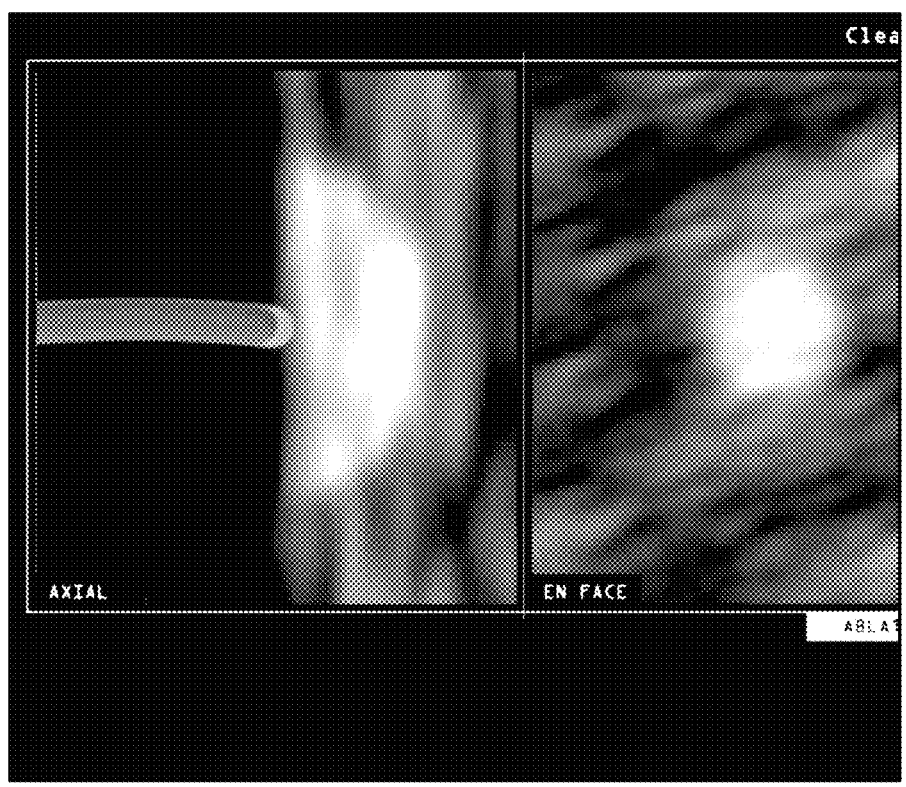

FIGS. 22A and 22B illustrate two windows of the axial and en face views of local tissue. FIG. 22A shows the tissue prior to ablation and FIG. 22B shows the tissue during or after an ablation. For example, during an ablation mode the system can use a default viewing rule to display the near real time MR image data of the affected tissue during the treatment, e.g., ablation, typically showing both en face and side views of the local tissue and treatment (ablation tip) according to embodiments of the present invention. In certain embodiments, the interactive visualization map 100v and/or model 100M may not be displayed during all or some of the ablation.

Figure 8:
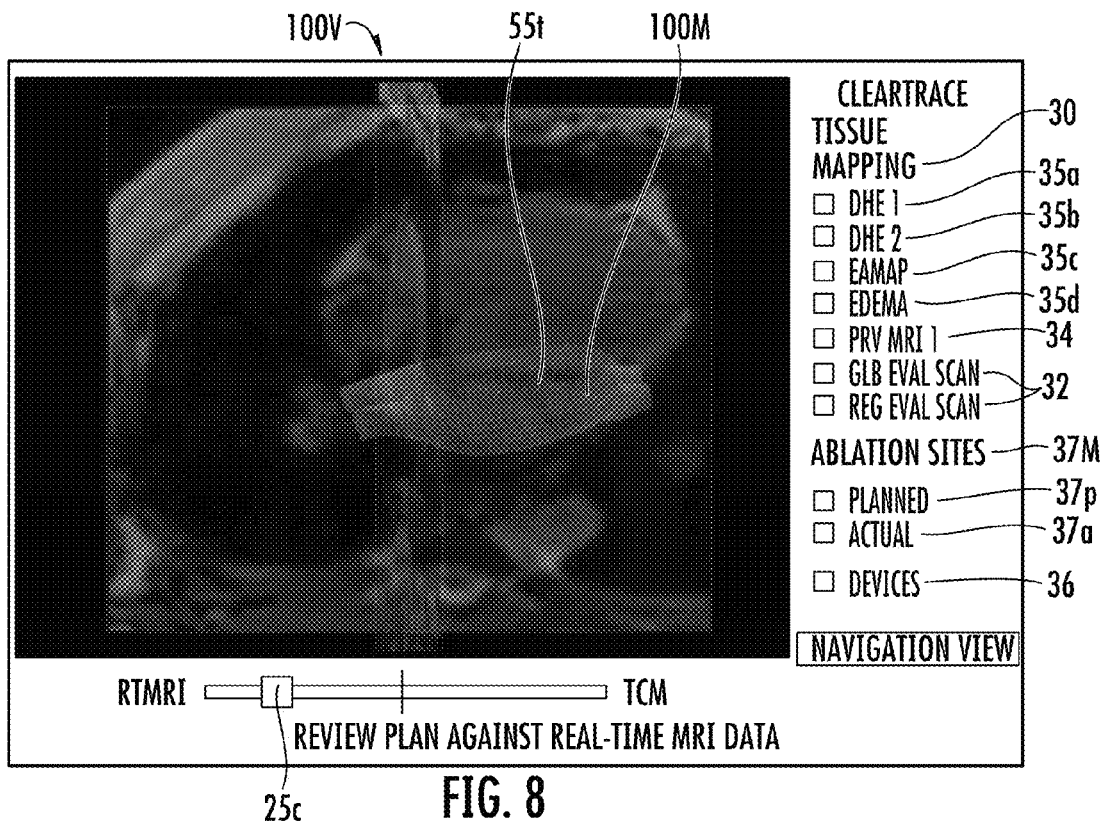
Figure 10:
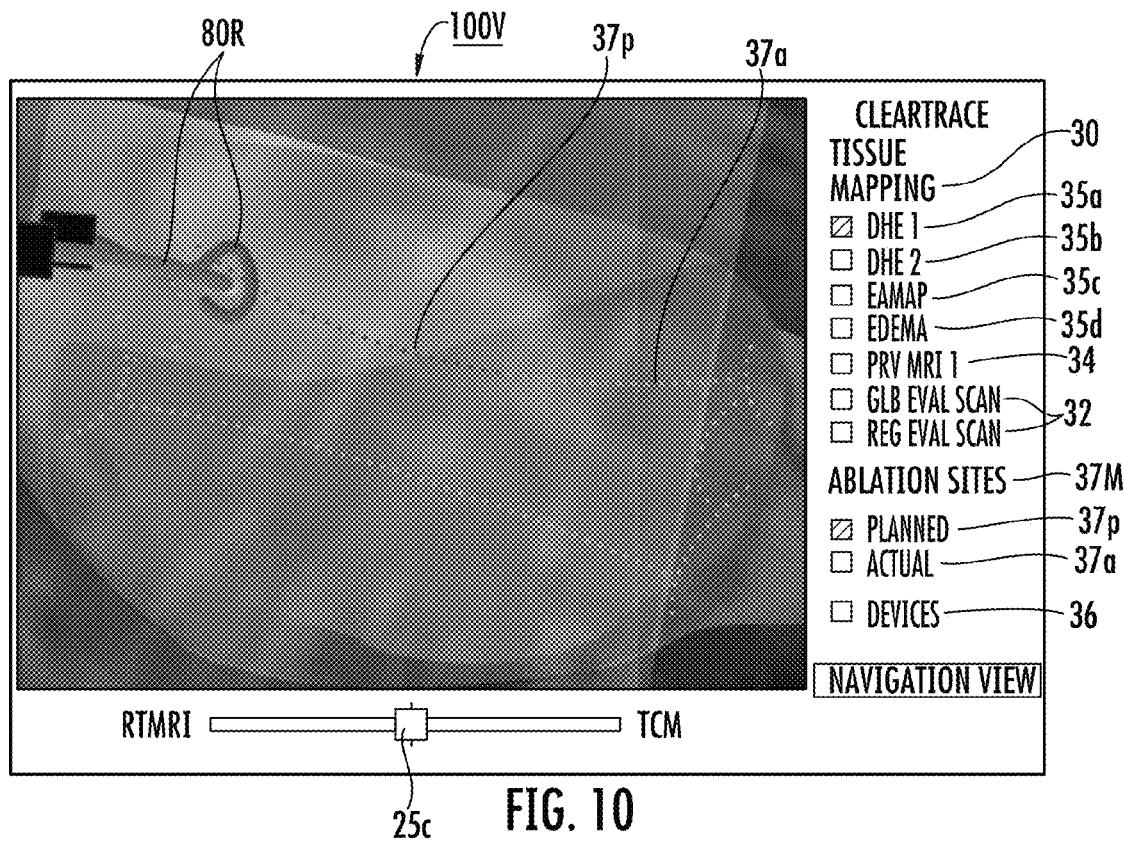
Figure 11:
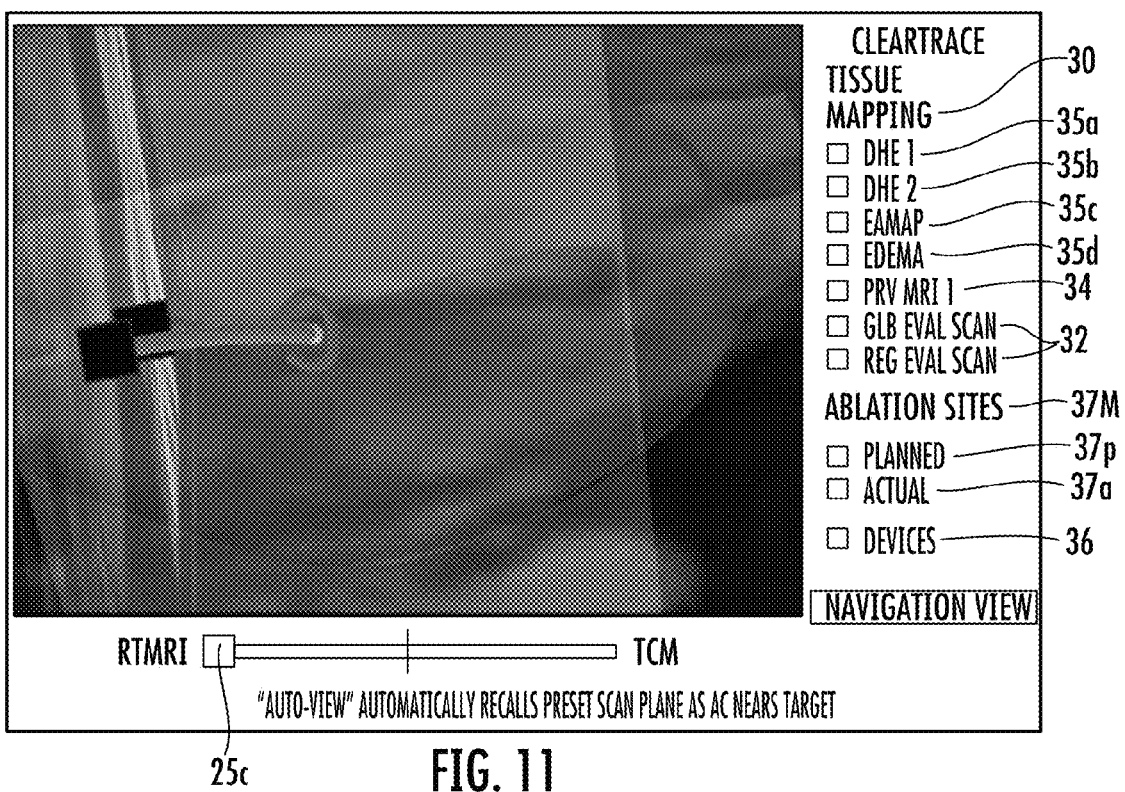
Figure 12:
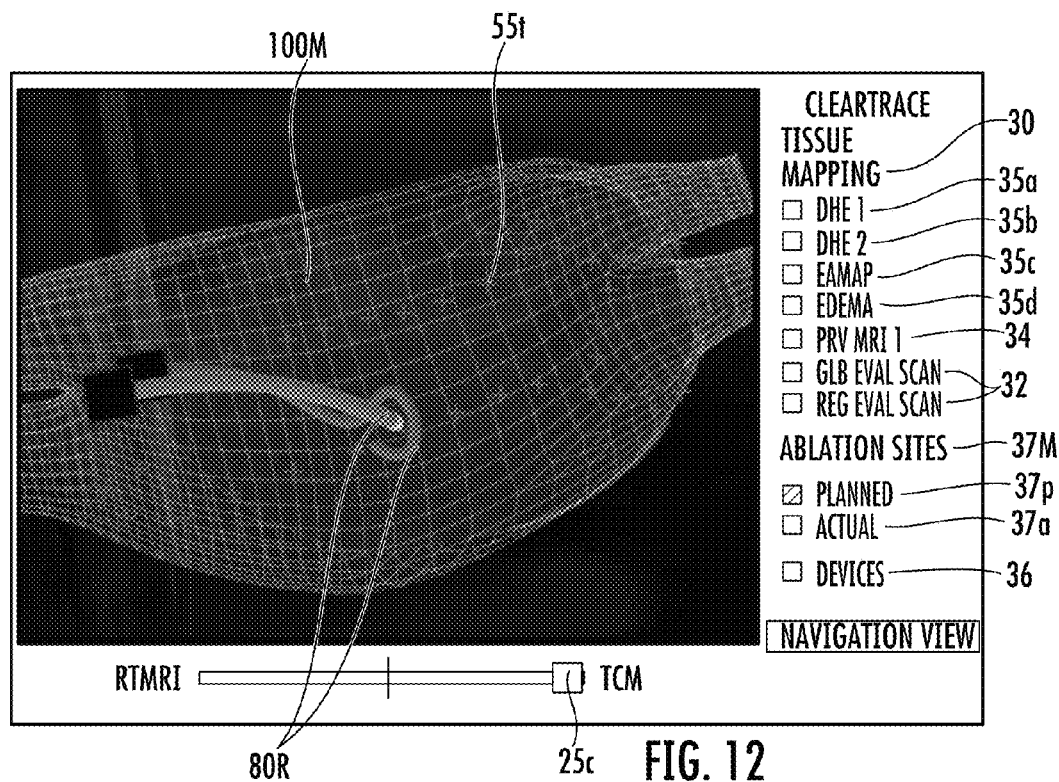
Figure 25:
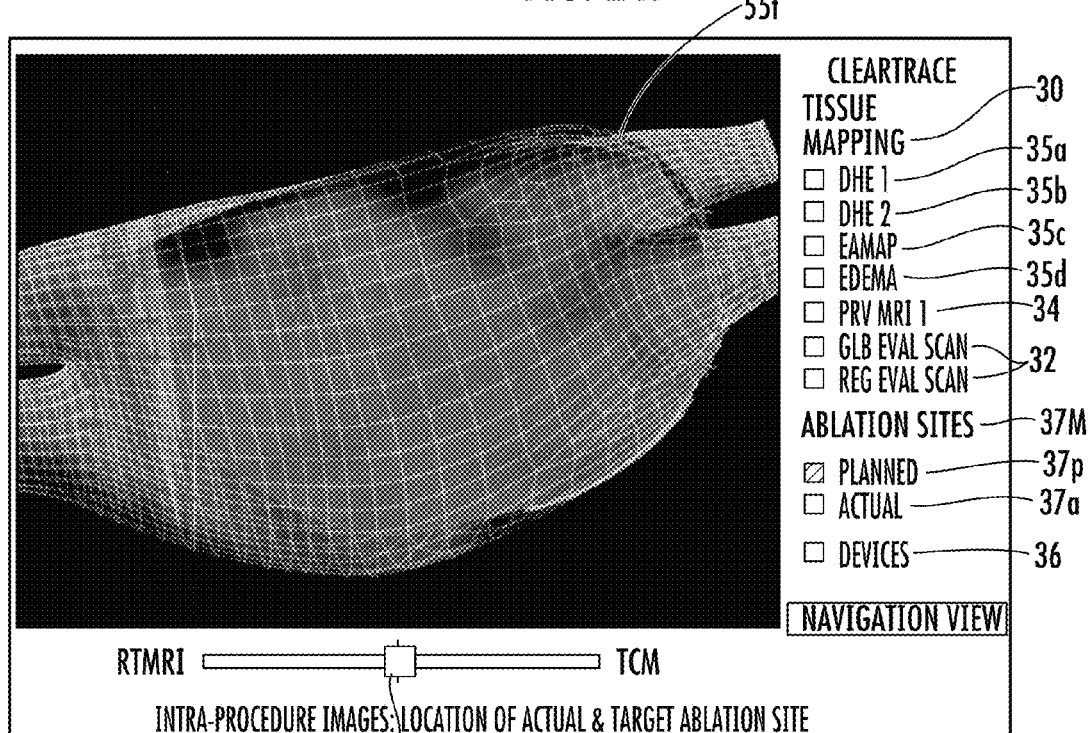
FIGS. 25-28 are yet additional exemplary (contemplated) screen shots illustrating patient data and target (clinician identified) treatment zones that can provide information that can help drive clinical decisions according to embodiments of the present invention.
Figure 26:
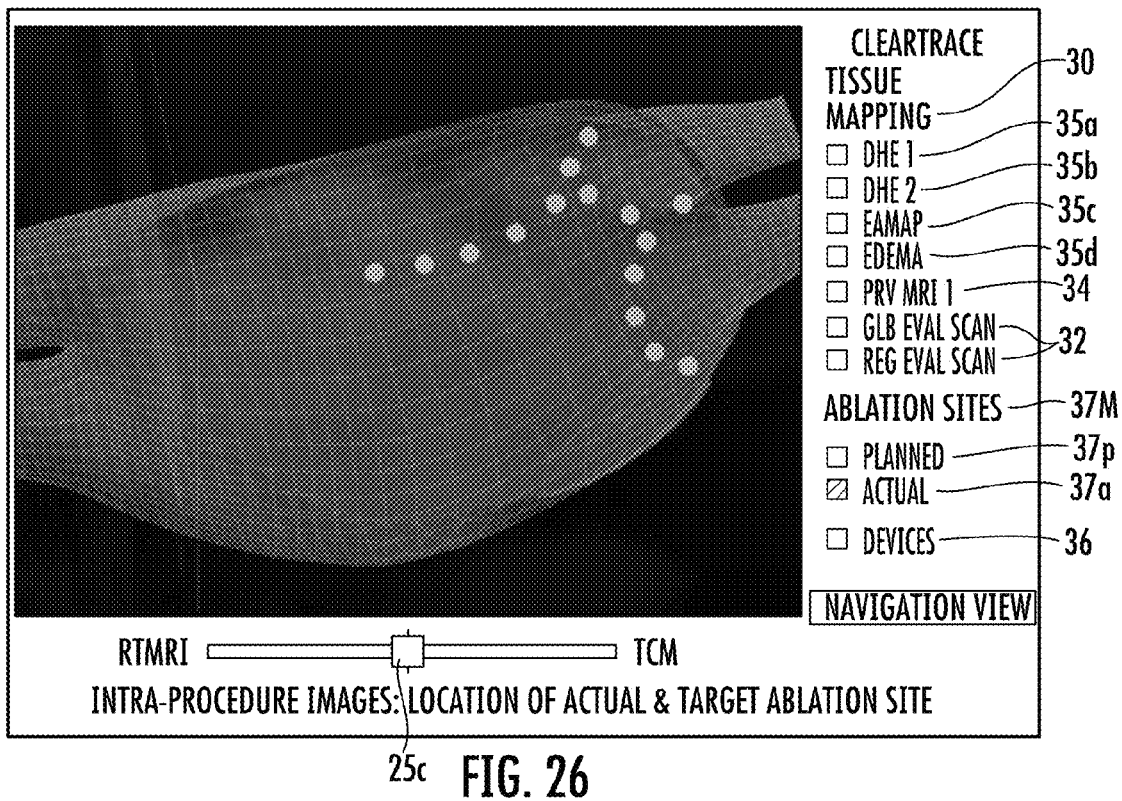

Referring to FIGS. 8, 12, and 25, in some embodiments, the UI 25 can also include a user input control 25c to allow a user to identify and/or select (e.g., mark) target ablation sites 55t on a tissue planning map 37M and subsequently provide planned and actual ablation tissue maps 37a or (which may be overlaid with different colors for easy comparison in viewing) or merged into a composite map that indicates both planned and actual sites (FIG. 10).

Figure 14:
Figure 21:
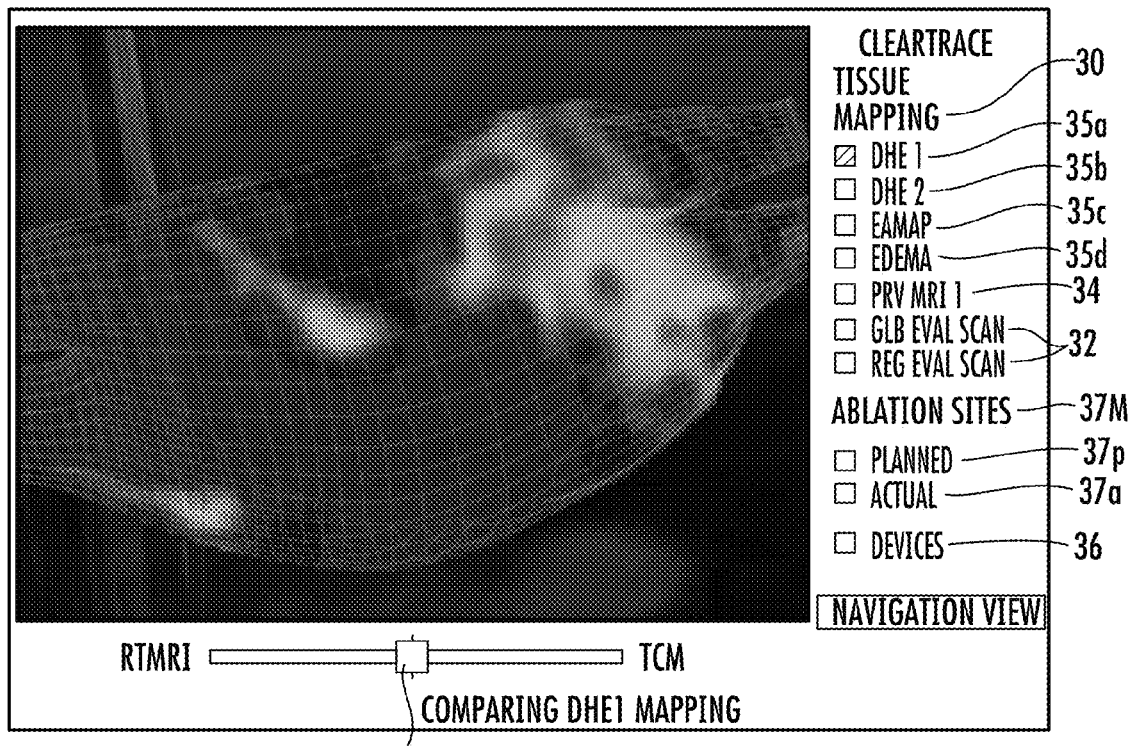

FIGS. 14, 17 and 21 illustrate enlarged (high resolution image) views of tissue that can be shown based on actual MR image data. This allows a physician to see the tissue that is targeted for treatment (e.g., ablation) prior to and/or during treatment (e.g., ablation). This type of viewing can be carried out during a planning stage or to evaluate lesions after ablation rather than just during the treatment for tissue-specific data. In some embodiments, the enlarged image views can be shown in response to user input in the interactive visualization. That is, the image views can be based on the placement of a target treatment site 55t in or on the map 100M.

Figure 15:
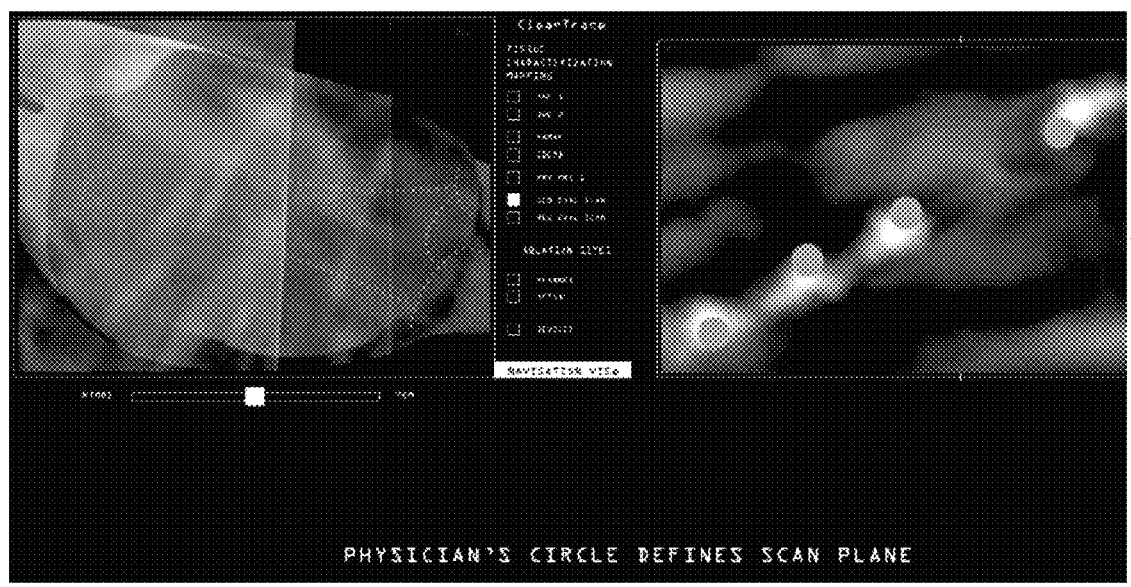
Figure 16:

FIG. 14 illustrates that a clinician (physician) can mark an area on the model 100M of the interactive visualization 100v shown as a circle toward the left side of the left window. FIG. 15 shows that the lesion pattern may be incomplete. FIG. 16 illustrates that the marked area in FIG. 14 may define the scan plane for the close-up views in the right hand viewing window.

FIGS. 10, 12 and 13 illustrate a "complete" planning map 37M with a number of target ablation sites 37p/55t for forming desired transmural lesions and/or electrical isolation patterns as selected by the physician (user). FIG. 10 illustrates both planned and actual treatment sites. After a planned ablation pattern is indicated, or as a mark or particular lesion site is selected and/or placed on the planning map 37M, a physician/user can review real-time MR image data of the spot and affirm the selected site is a desired target ablation site(s) 55t. FIG. 8 illustrates that the display can show a planned ablation site pattern 55t applied to the model 100M along with near real time patient MRI data.

In some embodiments, the planned treatment (e.g., ablation) pattern can use an electronically generated (default) template based on a predefined condition to be treated and certain fiducials associated with the target anatomy. The template may also be based on a clinician-specific preference for such a condition that can be electronically stored for use over different patients. The template can be modified based on patient-specific anatomy or other information. The ablation pattern can be electronically "drawn" or marked on the model 100M prior to its registration in the image space. The system can be configured to electronically identify relevant scan planes for the different marked lesion sites or areas after registration in the image space or propose scan planes that match contour of local anatomy that will include the target ablation site(s).

FIG. 17 illustrates that the display can show the interactive visualization 100v in one viewing window and that previous ablations in the indicated region can have an electronic associated scan plane(s) that can be used to define a new (or current) scan plane for regional evaluation of the lesion or other therapy.

Figure 20:
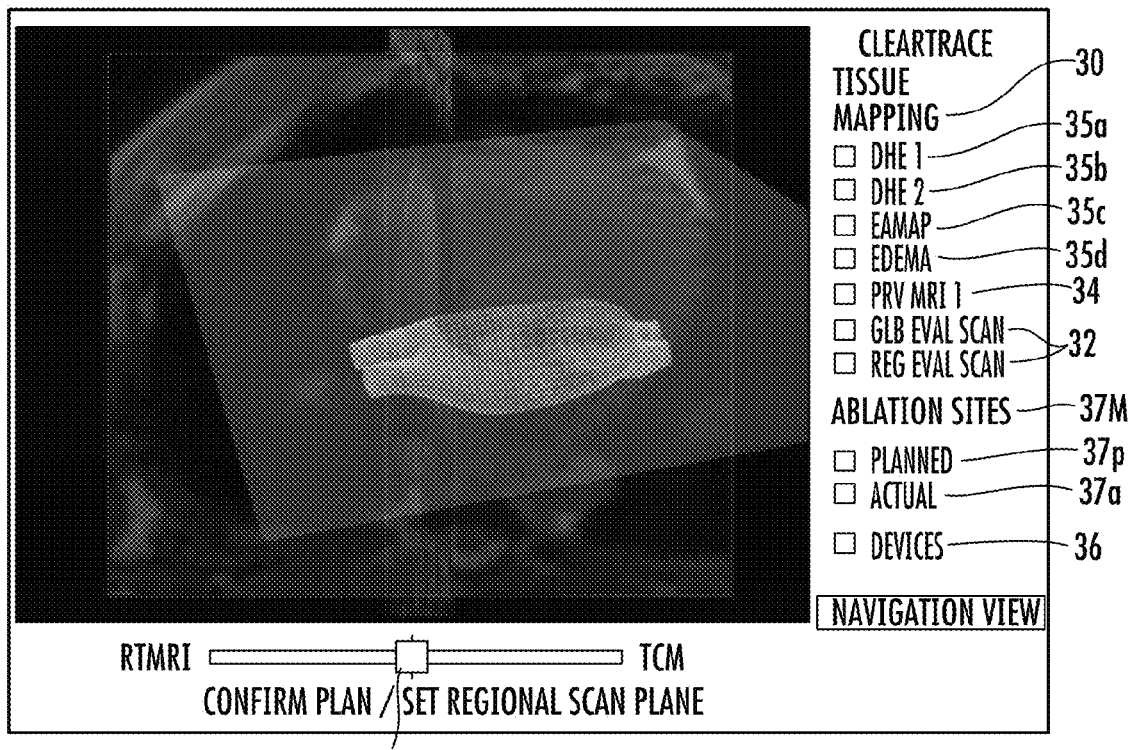

FIG. 20 shows that the visualization 100v can be used to confirm a desired therapy plan (ablation sites) and set a regional scan plane. Note also the difference from FIG. 8 with the visualization showing the model more predominant than the MR image data according to user input.

The model/map 100M can be shown in wire grid form (FIG. 9) or in varying intensity or opacity based on user input or default settings. FIG. 9 also shows the near RT image data suppressed or not shown in the visualization 100v.

FIG. 22A shows that scan planes for the therapeutic (e.g., ablation) view(s) can be automatically determined based on the identified location of the tracking coil(s) 82c as discussed above.

The circuit 60c can electronically define and pre-set scan planes associated with a respective target ablation site correlated to an actual location in 3-D space which is then electronically stored in electronic memory as pre-set scan planes for that target location. The MRI images in treatment-view mode (e.g., ablation-view mode) can automatically be displayed when the treatment device 80 reaches the corresponding physical location in the target anatomy (e.g., heart) during the procedure. The planned target sites 55t may also used to define the physician view (3-D perspective), e.g., a preset view, whenever the treatment device 80 (e.g., ablation catheter) is in proximity to the defined location associated with the target site. Thus, the target sites 55t identified in the planning map 37M can be used to preset both associated scan planes with real time MRI and the 3-D view for display without requiring further clinician input.

During the procedure, as the distal end of the device 80 (e.g., ablation catheter) approaches a location that corresponds to a target treatment (e.g., ablation) site 55t, the circuit 60c (e.g., MR Scanner 10S) can automatically select scan planes that "snap to" the tip and/or distal end portion location using a scan plane defined "on the fly" based on the calculated location of the distal end portion of the device (typically selected so that the slice includes a region offset from and/or projected forward a distance beyond the device such as between about 0-4 mm, typically about 1-2 mm) and/or using one or more of the preset scan planes associated with that location to obtain real-time MR image data of the associated tissue. The scan planes can be adjusted in response to movement of the device (as typically detected by tracking coils) prior to or during treatment. FIG. 11 indicates an auto-view using a recalled preset scan plane as the device 80 nears or contacts target tissue. In some embodiments, the system may automatically enable or disable ECG gating as necessary when defining scan planes, markers, recording electrograms, and the like.

In some embodiments, the snap-to scan plane(s) can be carried out based on the position of two closely spaced tracking coils 82c on a distal end of the device 80. The two coils 82c can be held on a relatively rigid substrate or catheter end with between about 2-10 turns/coil. The tracking coils 82c can be connected via a respective coaxial cable to the MR scanner 10S as noted above. The snap-to or projected scan plane can be projected a distance beyond the calculated tip location, such as between about 0-4 mm as discussed above. This embodiment may be particularly suitable for a deflectable end ablation catheter with a tip RF electrode. In other embodiments, such as for a loop catheter, the tracking coils 82c can be held on a loop end of the device and reside on a common plane. The circuit 60c can be configured to define the plane based on the location of at least three of the tracking coils 82c. The tissue-device interface for the snap-to location can be selected to be parallel and proximate the identified plane (e.g., between about 0-4 mm from the plane). In yet another embodiment, a device can have between about 1-20 tracking coils along its length (e.g., along a distal end portion thereof). The snap-to location can be based on a location that is tangent and in-line with at least two of the tracking coils (e.g., 2, 3, 4 coils on the shaft). The device may deflect and the position of at least some of the tracking coils may change relative to each other. This embodiment may be particularly suitable for a mapping catheter which has a mostly straight configuration but may have a curved portion.

For example, in some embodiments, the circuit 60c and/or MR Scanner 10S can adjust the scan planes if the physician moves the ablation catheter to obtain slices that show the ablation of the lesion including side and en face views showing near real-time MRI of the tissue being ablated. The scan planes are selected to include slices that are projected outward a distance axially along the line of the device to include relevant tissue. For an optimal or proper en face view the scan plane can be oriented to a plane that is substantially parallel to the target tissue surface (e.g., proximate a tip of the device). This can be done based on coordinates of the 3D segmentation/model relative to the tip position.

To obtain a slice with a relevant scan plane for the en face view, the device tip can be used to define one point and the circuit could identify a plurality of additional points (e.g., about three more points) on the surface of the model 100M. Those additional points can be a short radius away from the device tip (i.e., similar to a spoke and wheel pattern). Distance of the (three) radial points should be closely spaced relative to the center point, particularly for curved tissue surfaces (e.g., the cardiac walls being ablated or otherwise treated will usually be curved, and in some cases, even have complex curves like the PV ostia). Choosing this distance may be made with reference to typical human cardiac anatomy, the distance of those points may be between about 3 to 5 mm. In some particular embodiments, the following steps may be used to obtain the en face views.

1. Project a line forward from the most distal tracking coils on the intrabody device.
2. Electronically generate (e.g., mark) a temporary point where that projected line intersects the surface of the 3D model
3. Use that temporary point of intersection as the center of the "wheel" and calculate the location of three points on the rim of the wheel.
4. Proscribe a temporary plane that includes the three rim points.
5. Translate the temporary plane until the temporary center point becomes coterminous with the actual tip of the device (assuming that the tip is actually against the target tissue (e.g., cardiac wall).
6. Set the scan plane based on this calculated plane for the en face view.

It is noted that the above steps may not be suitable where the device is a loop catheter. When using a loop catheter as the intrabody device with the tracking coils, the physician typically ablates on the inside of the loop and the circuit can use the coordinates of the tracking coils on the loop catheter to describe the scan plane for, the en face view.

In some embodiments, the system can keep track of the shortest line from the tip of the device to the registered model, and can even display this line in near real-time in the rendering(s). Then, with user input, e.g. on a button press, the circuit 60c can define a plane tangent to the model surface for the en face view, or along this line for the axial view. Gating may be used. The axial view may be more robust as it cuts through the wall.

In addition to substantially continuous collection of "new" image data in the visualizations and/or ablation or other therapy view modes, the data can also be processed by algorithms and other means in order to generate and present back to the surgeon in near real-time or upon request, a continuously updated, patient specific anatomical tissue characterization map of the anatomy of interest.

Figure 23:
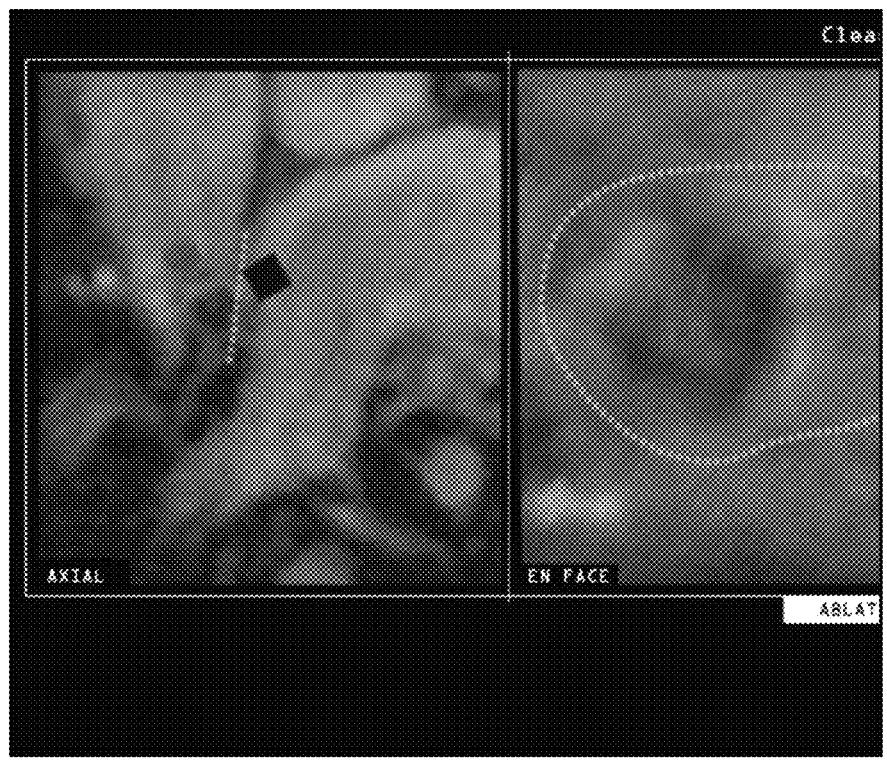
FIGS. 23 and 24A-D are exemplary (contemplated) screen shots illustrating navigational indicia that can be used to help guide and/or position an intrabody device according to embodiments of the present invention.
Figure 24A:
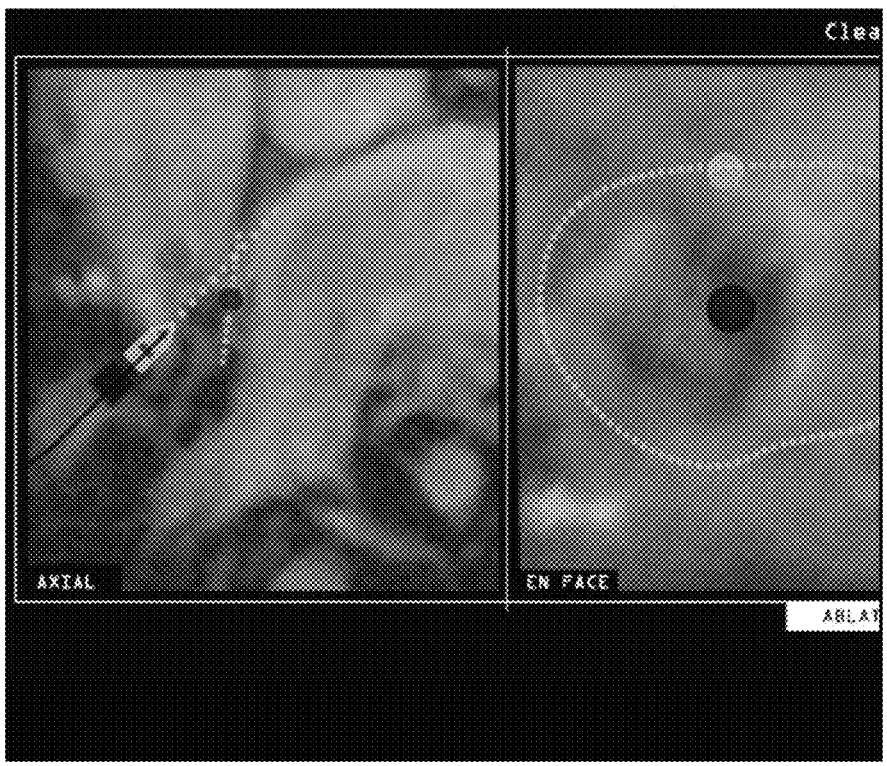
Figure 24B:
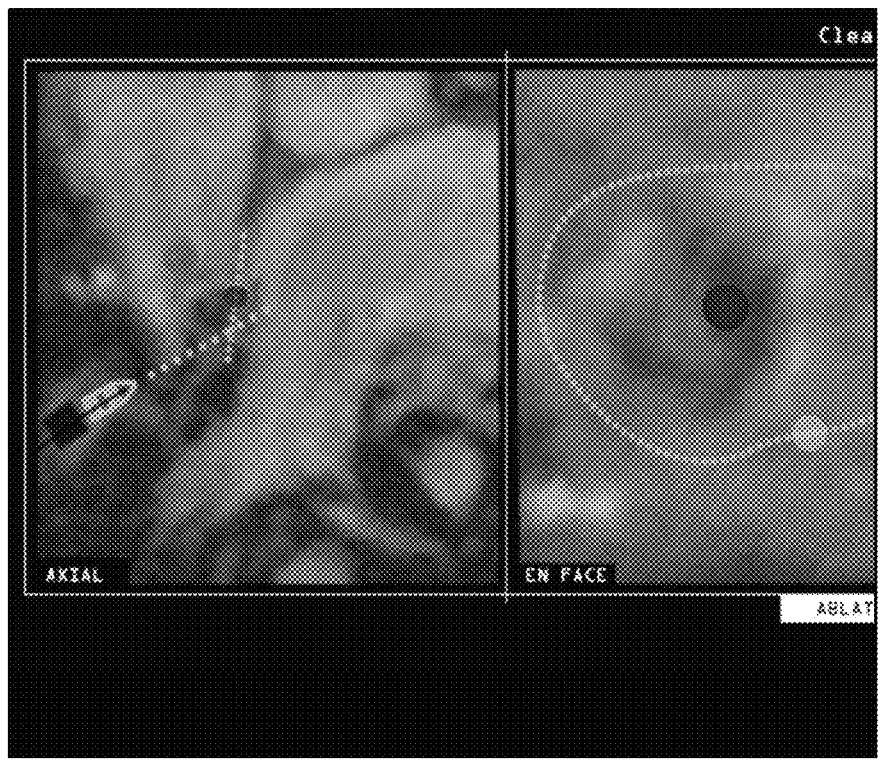
Figure 24C:
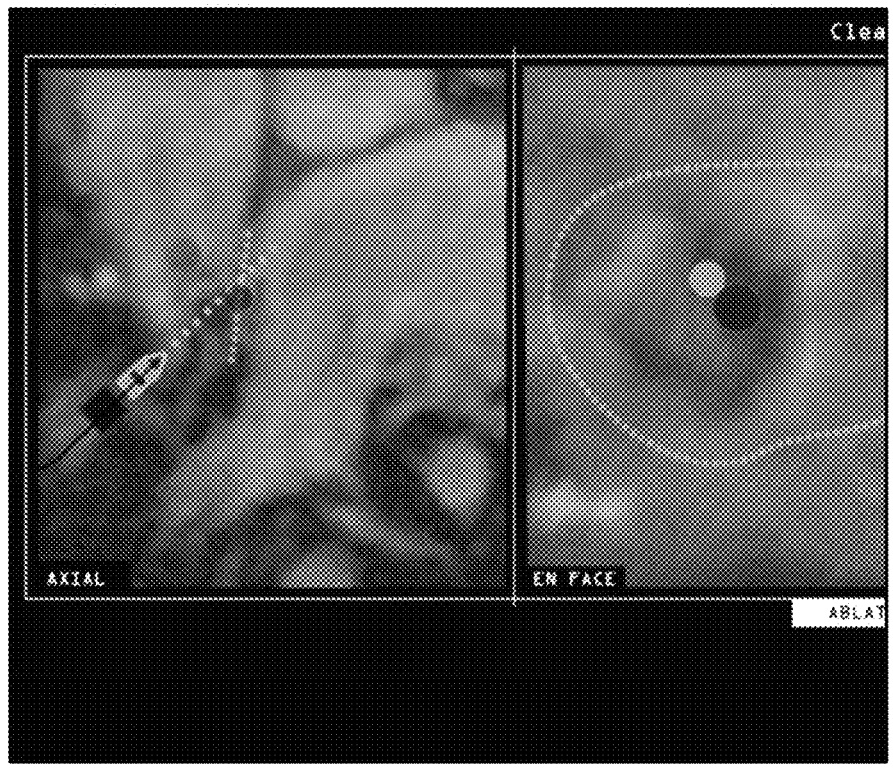
Figure 24D:
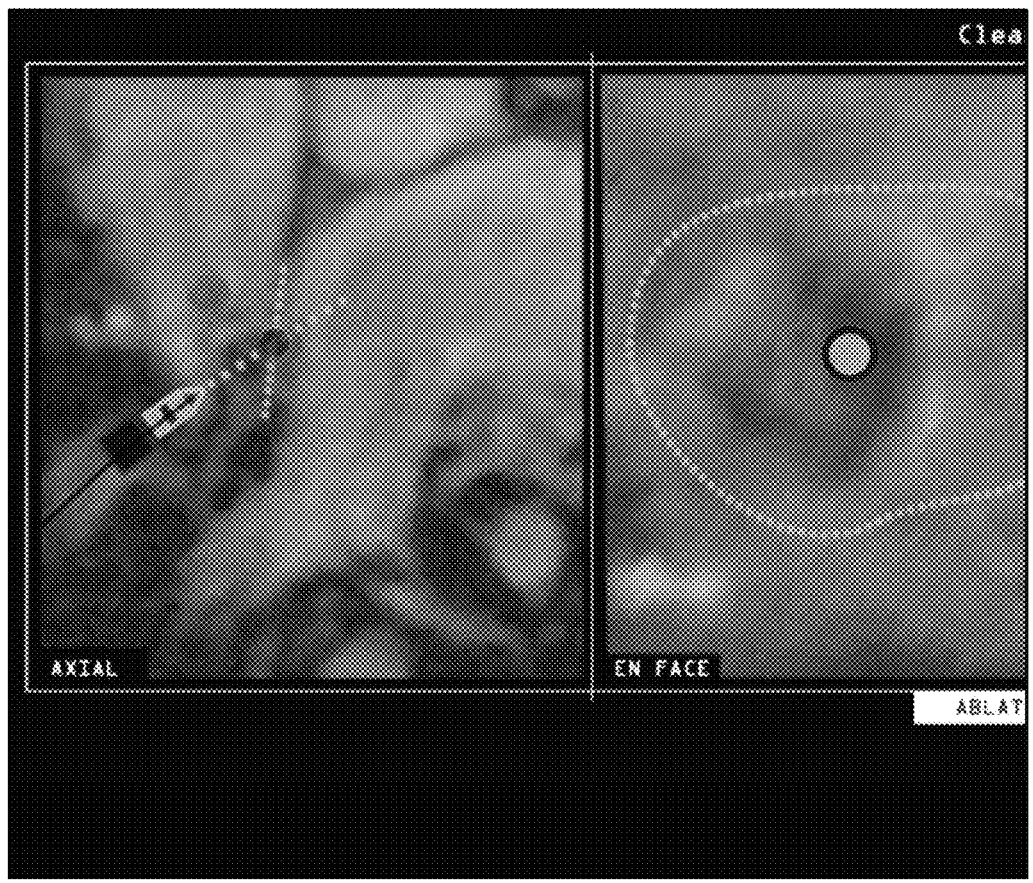

FIG. 23 illustrates that the system can illustrate the location of the treatment device 80 with additional visual indicators and a "target" navigational indicia (e.g., mark) for visual help in navigation to the site.

FIGS. 24A-24D illustrate that the system can generate visual navigational markers for facilitating alignment using MRI-guidance.

In particular embodiments, during ablation, MR thermometry (2-D) can be used to show real-time ablation formation taking a slice along the catheter and showing the temperature profile increasing. It is contemplated that 2D and/or 3D GRE pulse sequences can be used to obtain the MR image data. However, other pulse sequences may also be used.

Figure 18:
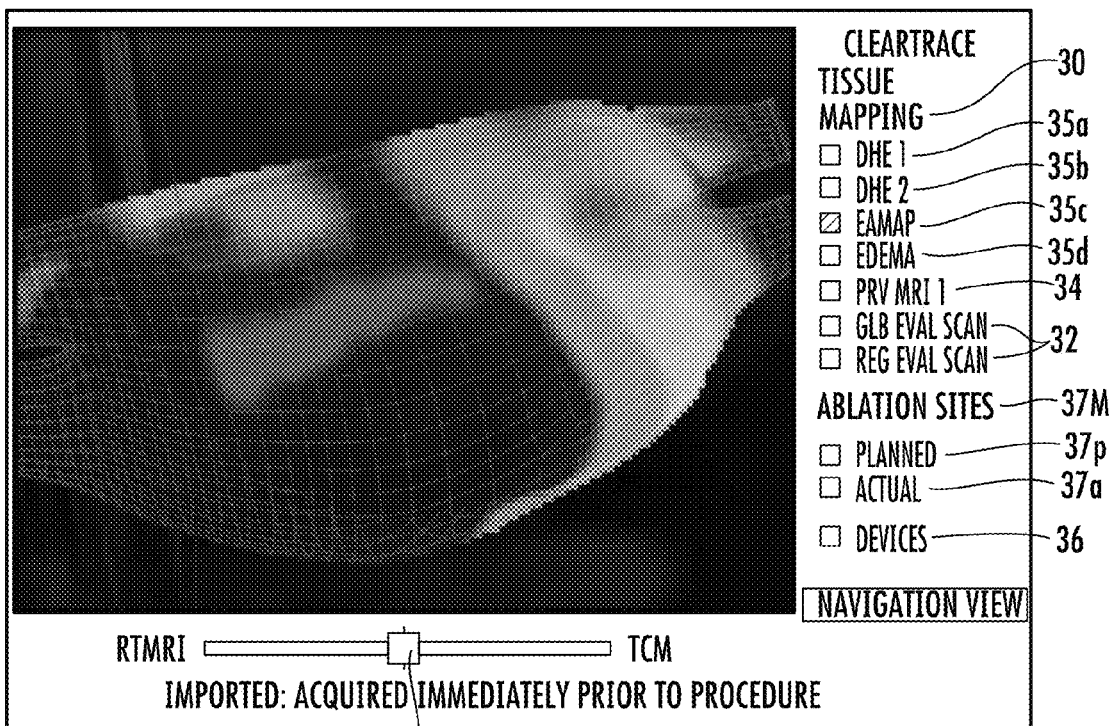

FIGS. 18 and 19 illustrate examples of maps 30 of pre-acquired patient data that can be imported (and registered to the image space) for use during a cardiac interventional procedure, typically used as the map 100M in the interactive visualization 100v. As shown in FIG. 18, an EA map can be obtained prior to (typically immediately prior to) the actual interventional procedure either while the patient is in the MRI scanner or from an X-ray based system from which the EA map can be registered to a different map, such as a tissue characterization map 30 and shown on the display 20. In some embodiments, the tissue characterization map can include, incorporate, overlay or underlay data from or an EA map (which may be imported from an X-ray imaging modality or generated in an MRI Scanner) to define an integrated electro and tissue characterization combination map. The electrical activity can be detected via electrical activity sensors that can detect impedance or other electrical parameter that can sense fractionated or normal electrical activity in cardiac tissue as is known to those of skill in the art. The electroanatomical map or data therefrom, where used, can be registered to the visualization map 100M (e.g., a different tissue-characterization map) so that MR data updates using MR data that is generated during the intervention can be generated and displayed on the integrated map.

Also, the UI 25 can be configured to allow a clinician to select or deselect the EA map (where used) so that the information from the EA map is electronically stripped or removed (and/or added back in) to the map 100M as desired. In other embodiments, the map 100M is maintained separate from the EA map, and if used, the EA map is shown in a separate window or screen apart from the tissue characterization map.

FIGS. 21 and 27 show examples of MRI DHE tissue characterization maps. FIG. 21 shows a pre-procedure "planning" DHE image taken before, typically about 1 week before, the planned procedure. In some embodiments, a DHE image can be taken after a prior ablation procedure illustrating locations of incomplete electrical isolation/scar formation for helping plan the target sites for the current procedure. A planning map can be placed over the map in the visualization so that a user/physician can mark the target ablation sites 55t as discussed above (which may in some embodiments also define preset scan planes and views before ablating during a procedure). FIG. 27 shows an intraprocedure DHE map that can be used to evaluate the ablation sites.

FIG. 28 illustrates that the map 100M can be rendered to show locations of target and actual ablation sites (in different colors) to allow a clinician to evaluate the scar formations and/or variation from the planned procedure intra-procedure according to embodiments of the present invention.

The MRI Scanner 10S (FIGS. 1-3) can be operated substantially continuously to provide image data that can be used to generate updated maps 100M in the visualizations upon request or automatically. This operation can be "in the background", e.g., transparent to the user so as not to slow down the procedure while providing updated image and tracking data during the course of the procedure.

In some embodiments, the device-tissue interface 100i (FIG. 1, 22A, 22B) can be visualized with a T1-weighted FLASH sequence (T1w FLASH) to localize the tip 80t. RF or other ablative energy can be delivered and myocardial or other target tissue changes and lesion formation can be visualized in near real-time using a T2 weighted HASTE (T2w HASTE) sequence. Real Time (RT)-MRI sequence, T1w FLASH and T2w HASTE image slices can be aligned to allow visualization of the device 80 upon tissue contact or activation of the ablation energy to allow visualization of the device 80 (e.g., catheter), the device-tissue interface 100*i* and/or the (myocardium) tissue while receiving the therapy, e.g., ablative energy.

In some particular embodiments, during navigation mode (rather than an ablation mode), the catheter 80 can be visualized using a different pulse sequence from that used in the high-resolution ablation mode, such as, for example, an RT MRI sequence using GRE or SSFP (e.g., TrueFISP) pulse sequence with about 5.5 fps), the tracking coils 82*c* can be used for spatial orientation and positioning. Typical scan parameters for (near) real-time include: echo time (TE) 1.5 ms, repetition time (TR) 3.5 ms, a flip angle of about 45 degrees or about 12 degrees, slice thickness 5 mm, resolution 1.8 mm×2.4 mm, parallel imaging with reduction factor (R) of 2. In some embodiments using SSFP, the flip angle is about 45 degrees.

Once the device position is deemed appropriate (using tracking coils 82*c*), a pulse sequence at the associated scan plane can be used to generate high resolution visualization of the catheter tip 80*t* and (myocardial) tissue interface. For example, a T1-weighted 3D FLASH sequence (T1w FLASH) as noted above. Myocardial or other target tissue images during ablation or other therapy can be acquired using an Inner Volume Acquisition (IVA) dark-blood prepared T2-weighted HASTE (T2w HASTE) or dark-blood prepared Turbo Spin Echo (TSE) sequence. Examples of HASTE and TSE sequence parameters include: TE=79 ms/65 ms, TR=3 heart beats, 3 contiguous slices with thickness of about 4 mm, resolution 1.25 mm×1.78 mm/1.25 mm×1.25 mm, fat saturation using SPAIR method, and parallel imaging with R=2, respectively.

Typical heart beat rates and free breathing can present imaging challenges. In some embodiments, (near) RT navigation imaging slices (e.g., GRE pulse sequence at 5.5 fps) can be aligned with high-resolution tissue interface slices (e.g., T1w FLASH) for visualization of the catheter-tissue interface. Subsequently, those slices obtained with T1w FLASH can be aligned with those obtained with dark-blood prepared T2w Haste images for myocardial tissue/injury characterization during energy delivery. This stepwise approach can allow confident localization of specific points within the atrium and while ablating tissue and simultaneously visualizing the tissue for near-real time assessment of tissue injury associated with lesion formation.

In some embodiments, slices acquired with different sequences can be interlaced to provide an interactive environment for catheter visualization and lesion delivery, a UI can allow a user to toggle between these views or can alternate the views based on these image slices or navigation versus ablation or interventional modes/views. It is also noted that the sequences described herein are provided as examples of suitable sequences and it is contemplated that other known sequences or newly developed sequences may be used for cardiac ablation or other anatomy or interventional procedures.

Figure 29:
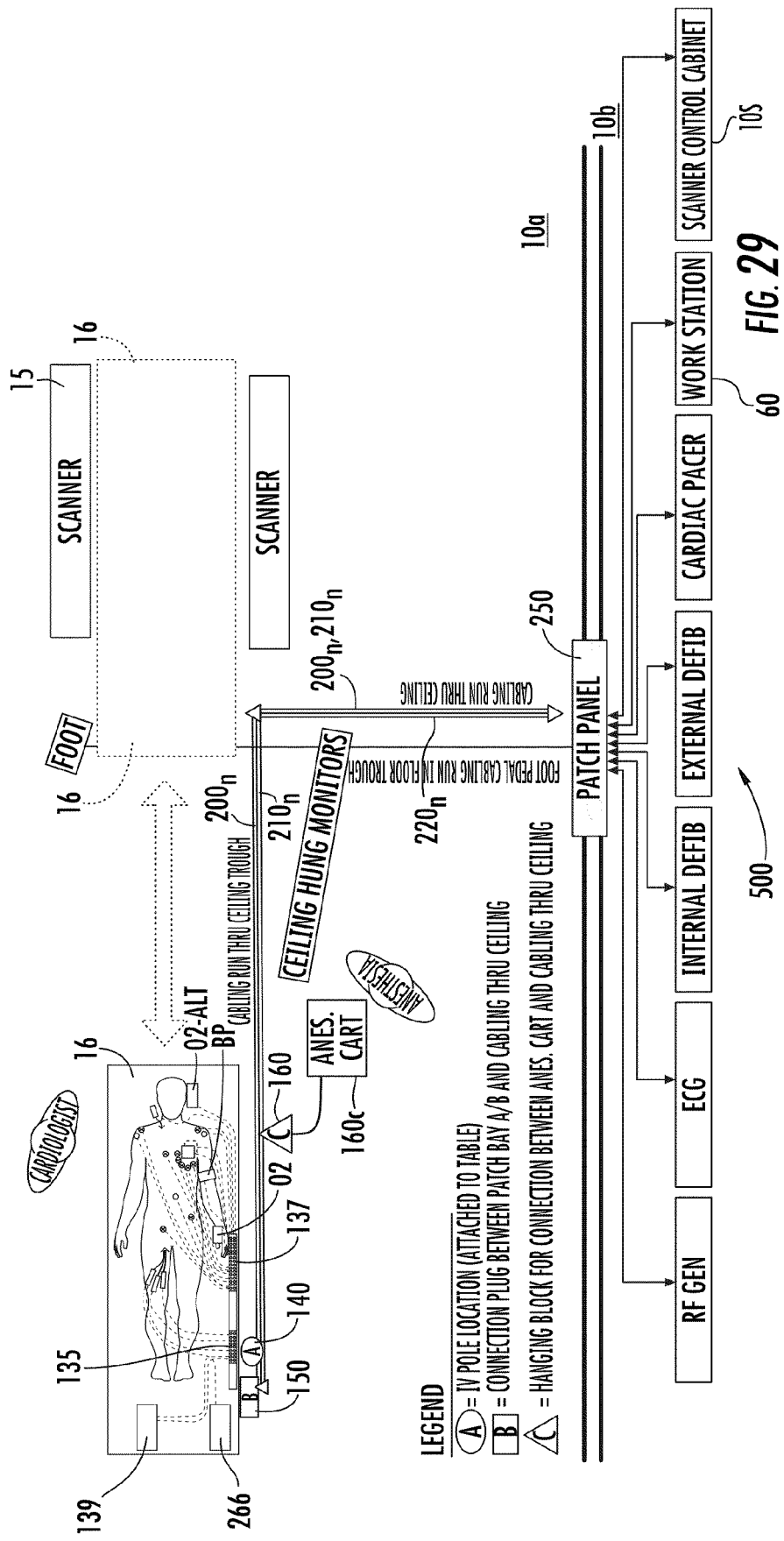
FIG. 29 is a schematic illustration of an MRI-interventional suite according to embodiments of the present invention.

FIG. 29 illustrates one particular embodiments using a cardiac MRI Interventional suite 19 with an integrated cable management system that connects multiple patient connected leads that remain in position even when a patient is translated in or out of a magnet bore on the gantry 16 (the magnet can be an open face or closed magnet configuration) to allow a clinician direct access to a patient. The other ends of the leads connect to power sources, monitors and/or controls located remote from the patient (typically in the control room not the magnet room). As shown in FIG. 29, the MRI interventional suite 19 can include an IV pole 140 (typically attached to the scanner table/gantry 16) and a connection block 150 of cables 200*n* that are routed through a ceiling (e.g., they extend up, through and above a ceiling) (where "n" is typically between about 1-400, typically between about 5-100), that connect to patch bay 135 and/or 137. Cabling 210*n* for anesthesia cart 160 can also be routed through the ceiling (where n is typically between about 1-400, typically between about 5-100). The cabling 200*n*, 210*n* extends through the ceiling between the rooms 10*a*, 10*b* and can connect to the remote devices 500 through a patch panel 250. In some embodiments foot pedal cabling 220*n* can extend through a floor trough to the patch panel/second room 10*b* as well (where "n" is typically between about 1-100 cables). For additional description of an exemplary cardiac suite, see, U.S. patent application Ser. No. 12/708,773, the contents of which are hereby incorporated by reference as if recited in full herein. The cables may also alternately be routed under, on or over the floor, suspended on walls, employ wireless connections and the like (and combinations of same).

As is known to those of skill in the art, there are typically between about 60-100 lesions generated during a single patient cardiac (AFIB) EP procedure. Other cardiac procedures may only require about 1 ablation or less than 60. A typical patient interventional cardiac procedure lasts less than about 4 hours, e.g., about 1-2 hours. Each lesion site can be ablated for between about 30 seconds to about 2 minutes. Linear transmural lesions (such as "continuous" drag method lesions) may be generated or "spot" lesions may be generated, depending on the selected treatment and/or condition being treated. The continuous lesion may be formed as a series of over lapping spot ablation lesions or as a continuous "drag" lesion.

The system can include a monitoring circuit can automatically detect which devices are connected to the patient patch bay. One way this can be achieved is by using ID resistors in the patch bay and/or interface as well as in various devices that connect thereto. The MRI scanner computer or processor or the clinician workstation module or processor can monitor resistors via connections CON1, CON2 and CON3. The devices 80 (FIG. 1) can have built-in resistors that modify the resistance by lines that connect to CON1, CON2 and CON3. Variation in resistance values helps the monitor which device is connected. Once that determination is made the scanner may automatically load special acquisition parameters, display parameters and update the progress of the procedure to display on the display 20 such as at workstation 60 (FIG. 3), for example.

Electrical isolation between the MR Scanner 10S and the device 80 can be provided via low pass filters inside and outside the MRI suite. As is known to those of skill in the art, components in the MRI Suite can be connected to external components using a waveguide built into the RF shield that encloses the MRI suite. Where used, the ablation catheter 80*a* can be an RF ablation catheter connected to an appropriate energy source, such as, for example, a Stockert 70 RF generator (Biosense Webster, Diamond Bar, Calif., USA) with MR compatible interface circuits configured for 3 T magnetic fields (where a 3 T system is used). The system can comprise an EP Suite with a Siemens Verio system (Siemens Healthcare, Erlangen, Germany) or other suitable scanner as well as suitable external imaging coils, such as spine and/or body array coils as is known to those of skill in the art. Other ablation catheters including balloon (cryoablation), laser, ultrasound and RF array electrodes and the like may also be used. Other therapeutic catheters or devices may be used including an injection needle catheter and the like.

FIGS. 30A, 30B, and 31-33 illustrate exemplary embodiments of a flexible (steerable) ablation catheter as the device 80. The ablation catheter 80A includes an elongated flexible housing or shaft 102 having a lumen 104 (FIG. 30B) therethrough and includes opposite distal and proximal end portions, only the distal end portion 106 is illustrated. The distal end portion 106 includes a tip portion 101 that contains an ablation electrode 110 at its tip 80t for ablating target tissue, and a pair of RF tracking coils 82c, individually identified as 112, 114. The distal end portion can include a second electrode for sensing local electrical signal or properties or the ablation electrode 110 can be bipolar and both ablate and sense. The proximal end portion of the catheter 80 is operably secured to a handle as is well known. The catheter shaft 102 is formed from flexible, bio-compatible and MRI-compatible material, such as polyester or other polymeric materials. However, various other types of materials may be utilized to form the catheter shaft 102, and embodiments of the present invention are not limited to the use of any particular material. In some embodiments, the shaft distal end portion can be formed from material that is stiffer than the proximal end portion and/or a medial portion between the distal and proximal end portions.

The device 80 can be configured to reduce the likelihood of undesired deposition of current or voltage in tissue. The device 80 can include RF chokes such as a series of axially spaced apart Balun circuits or other suitable circuit configurations. See, e.g., U.S. Pat. No. 6,284,971, the contents of which are hereby incorporated by reference as if recited in full herein, for additional description of RF inhibiting coaxial cable that can inhibit RF induced current.

Figure 30A:
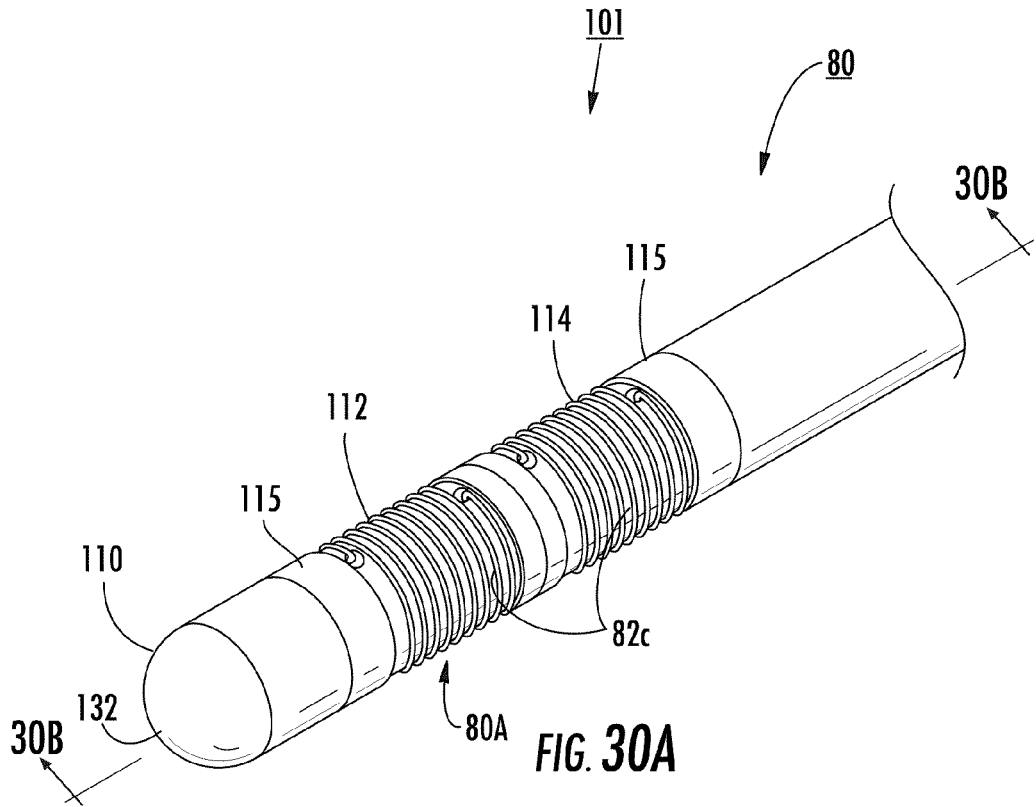
FIG. 30A is an enlarged partial perspective view of a tip portion of an exemplary ablation catheter according to particular embodiments of the present invention.
Figure 30B:
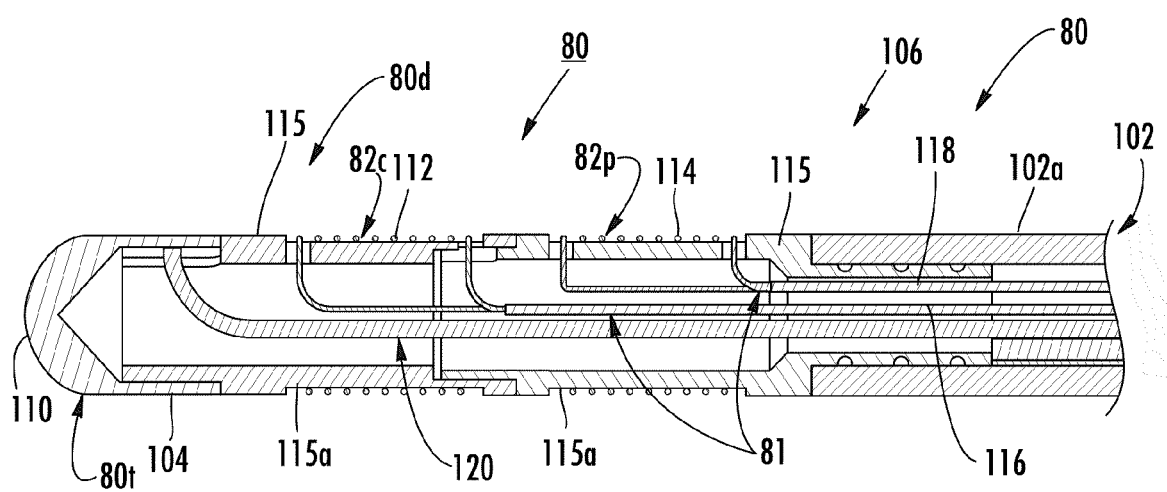
FIG. 30B is a cross-section of the tip portion of the catheter taken along lines 30B-30B in FIG. 30A.
Figure 31:
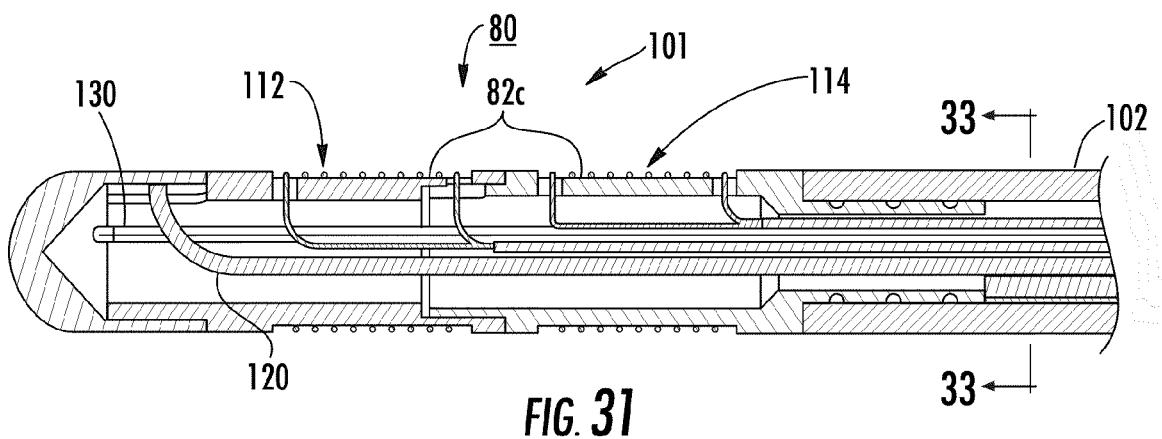
FIG. 31 is an enlarged axial cross section of a tip portion of another example of an ablation catheter according to embodiments of the present invention.

The device 80 can include tracking coils 112, 114 (FIGS. 30A, 30B, 31) on a distal end portion. In some embodiments, the tracking coils 82c reside upstream of the tip of the device (e.g., needle or ablation electrode). As shown in FIGS. 30A, 30B and 31, the ablation catheter includes a pair of tracking coils that reside adjacent to but typically upstream of the ablation electrode 110 on the tip of the catheter 80t) as all or some of tracking members 82 (FIG. 1). The catheter 80 can include an RF wire 120 that connects the ablation electrode 110 to an RF generator (FIGS. 30B, 31).

The device 80 can comprise coaxial cables 81 that connect the tracking coils 82c to the MR Scanner for tracking the location of the catheter in 3-D space. The cables or conductors 81 (and/or RF wire 120 where used) can include a series of back and forth segments (e.g., it can turn on itself in a lengthwise direction a number of times along its length), include stacked windings and/or include high impedance circuits. See, e.g., U.S. patent application Ser. Nos. 11/417,594; 12/047,832; and 12/090,583, the contents of which are hereby incorporated by reference as if recited in full herein. The conductors (e.g., coaxial cables) 81 (and/or RF wire 120, where used) can be co-wound in one direction or back and forth in stacked segments for a portion or all of their length.

In some embodiments, the ablation tip 80t is provided with one or more exit ports 132 (FIG. 30A) in communication with a fluid channel through which a fluid/solution (irrigant), such as saline, can flow before, during, and/or after the ablation of tissue. Fluid/solution is provided to the one or more exit ports 132 via an irrigation lumen 134 that extends longitudinally through the catheter shaft lumen 104 from the exit port(s) 132 to a handle. The irrigation lumen 134 is in fluid communication with a fluid/solution source at the proximal end portion 108 of the catheter shaft, typically at the handle. The fluid/solution can provide coolant and/or improve tissue coupling with the ablation electrode 110.

In some embodiments, a pull wire 136 (FIG. 32, 33) extends longitudinally within the catheter shaft lumen 104 from the distal end portion 106 to the handle at the catheter proximal end portion. The pull wire 136 extends longitudinally within a sleeve 138 (FIG. 32) that is attached to the internal wall of the lumen 104. The pull wire 136 is attached to the sleeve 138 near the distal end portion 106 of the catheter 80 and otherwise is slidably disposed within the sleeve. Pulling the pull wire 136 in a direction towards the handle causes the tip portion 101 of the catheter to articulate in one direction. Pushing the pull wire 136 in the opposite direction away from the handle causes the tip portion 101 to articulate in another different direction.

Figure 32:
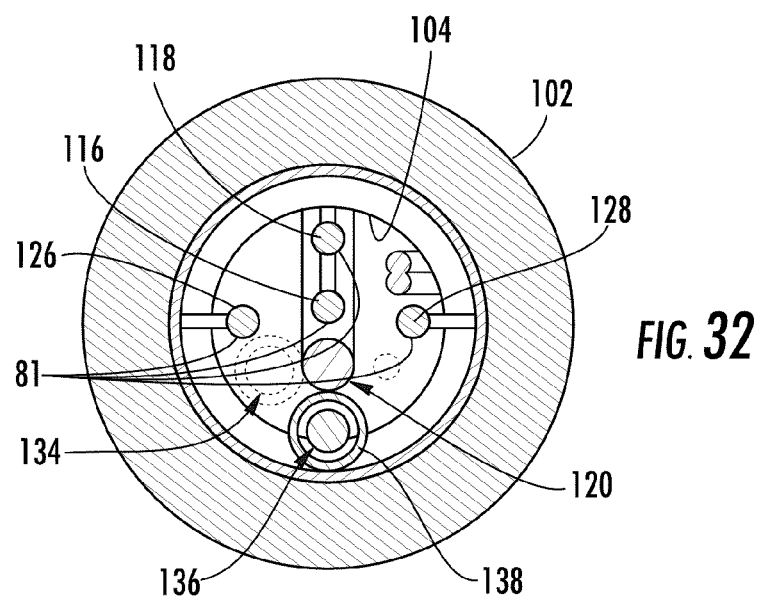
FIG. 32 is an enlarged cross-section of the catheter shown in FIG. 31.
Figure 33:
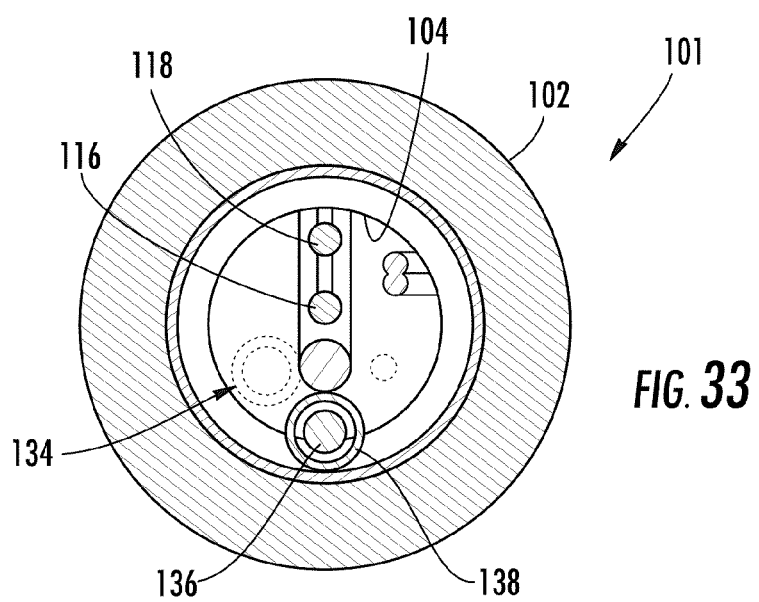
FIG. 33 is an enlarged cross-section of the catheter shown in FIG. 31 taken along lines 33-33 in FIG. 31. The FIG. 32 section view is taken at a location upstream of that shown in FIG. 33.

FIGS. 32 and 33 are cross sectional views of the distal end portion 101 of the illustrated catheter 80 according to some embodiments of the present invention. The sectional view shown in FIG. 32 is taken further upstream from that shown in FIG. 33. FIG. 32 illustrates the location and configuration of the coaxial cables (generally referred to as element 60) particularly referred to as 116, 118, 126 and 128 which are connected to the tracking coils 112, 114, 122 and 124, respectively. Coils 122, 124 are upstream of the portion of the device shown in FIGS. 30A and 30B. FIG. 32 also illustrates the location and configuration of the RF wire 120 that is connected to the ablation tip electrode 110 and that provides RF energy to the ablation tip electrode 110. FIG. 32 also illustrates the location of an exemplary thermocouple 130, and the location of an irrigation lumen 134. FIG. 33 illustrates the location and configuration of the coaxial cables 116, 118 which are connected to the RF tracking coils 112, 114. FIG. 33 also illustrates the location and configuration of the RF wire 120 connected to the ablation tip electrode 110, the location of thermocouple 130, and the location of irrigation lumen 134.

As discussed above with respect to FIG. 4, each tracking coil circuit can include a PIN diode and DC blocking capacitor and is typically located within the handle, although in other embodiments, the tracking coil circuits can be located within the catheter shaft lumen 104 closer to a medial or distal end portion (not shown) or in an interface, connector or other location. Each tracking coil circuit can be electrically connected to an MRI scanner, and can reduce signal noise within a respective channel caused by undesired coupling during scanner operation. In some embodiments, the tracking coil circuit can produce about 100 ohms impedance across an RF tracking coil when the PIN diode is shorted, for example, by an MRI scanner during scanner operations.

In some embodiments of the present invention, RF tracking coils 112, 114, 122, 124 may be between about 2-16 turn solenoid coils, typically 2-10 turn solenoid coils. However, other coil configurations may be utilized in accordance with embodiments of the present invention. Each of the RF tracking coils 112, 114, 122, 124 can have the same number of turns or a different number of turns, or different ones of the RF tracking coils 112, 114, 122, 124 can have different numbers of turns. It is believed that an RF tracking coil with between about 2-4 turns at 3.0 T provides a suitable signal for tracking purposes.

Embodiments of the present invention may be utilized in conjunction with navigation and mapping software features. For example, current and/or future versions of devices and systems described herein may include features with adaptive projection navigation and/or 3-D volumetric mapping technology, the latter may include aspects associated with U.S.

patent application Ser. No. 10/076,882, which is incorporated herein by reference in its entirety.

Figure 34:
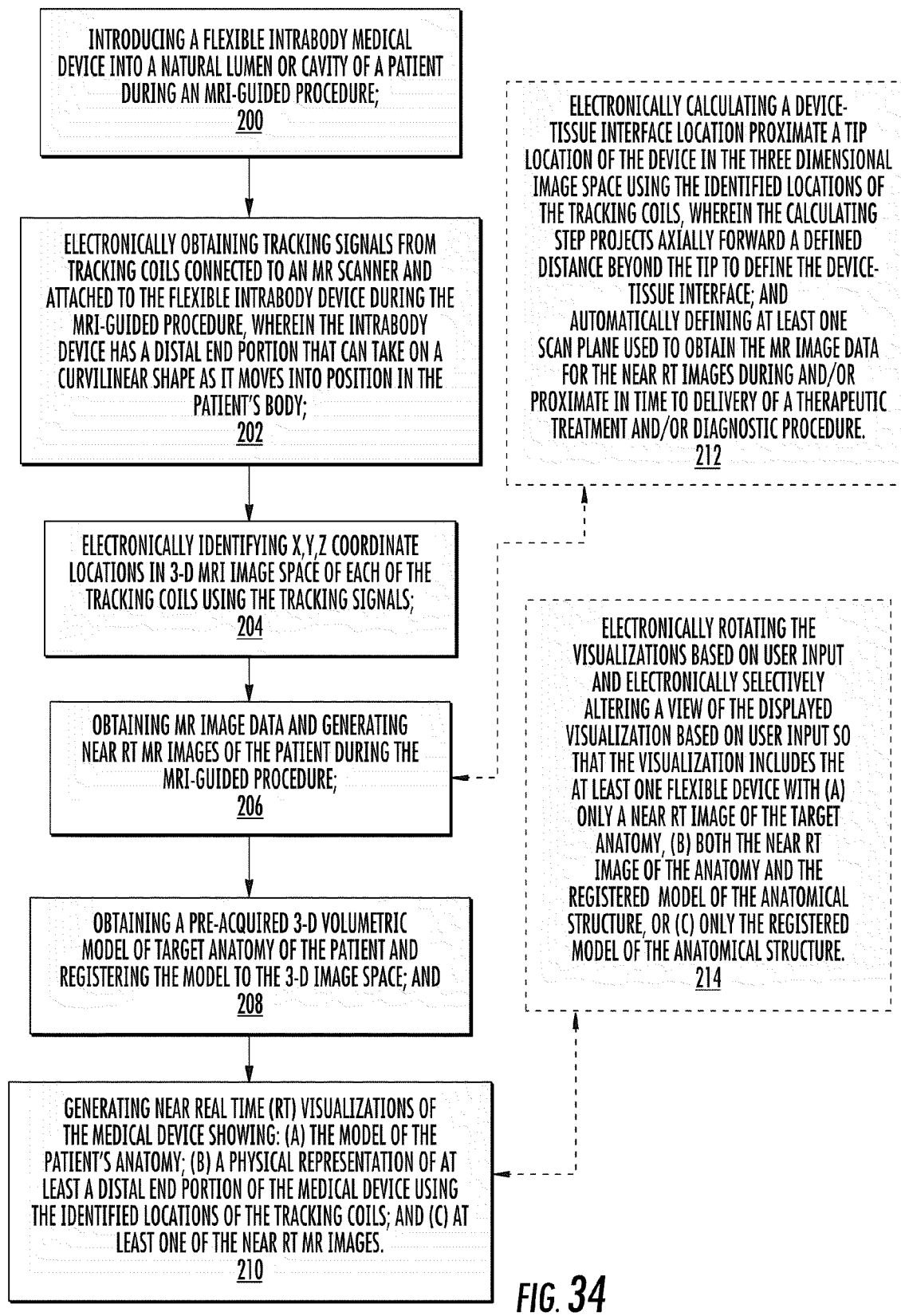
FIG. 34 is a flow chart of exemplary operations that can be used to carry out embodiments of the present invention.
Figure 35:
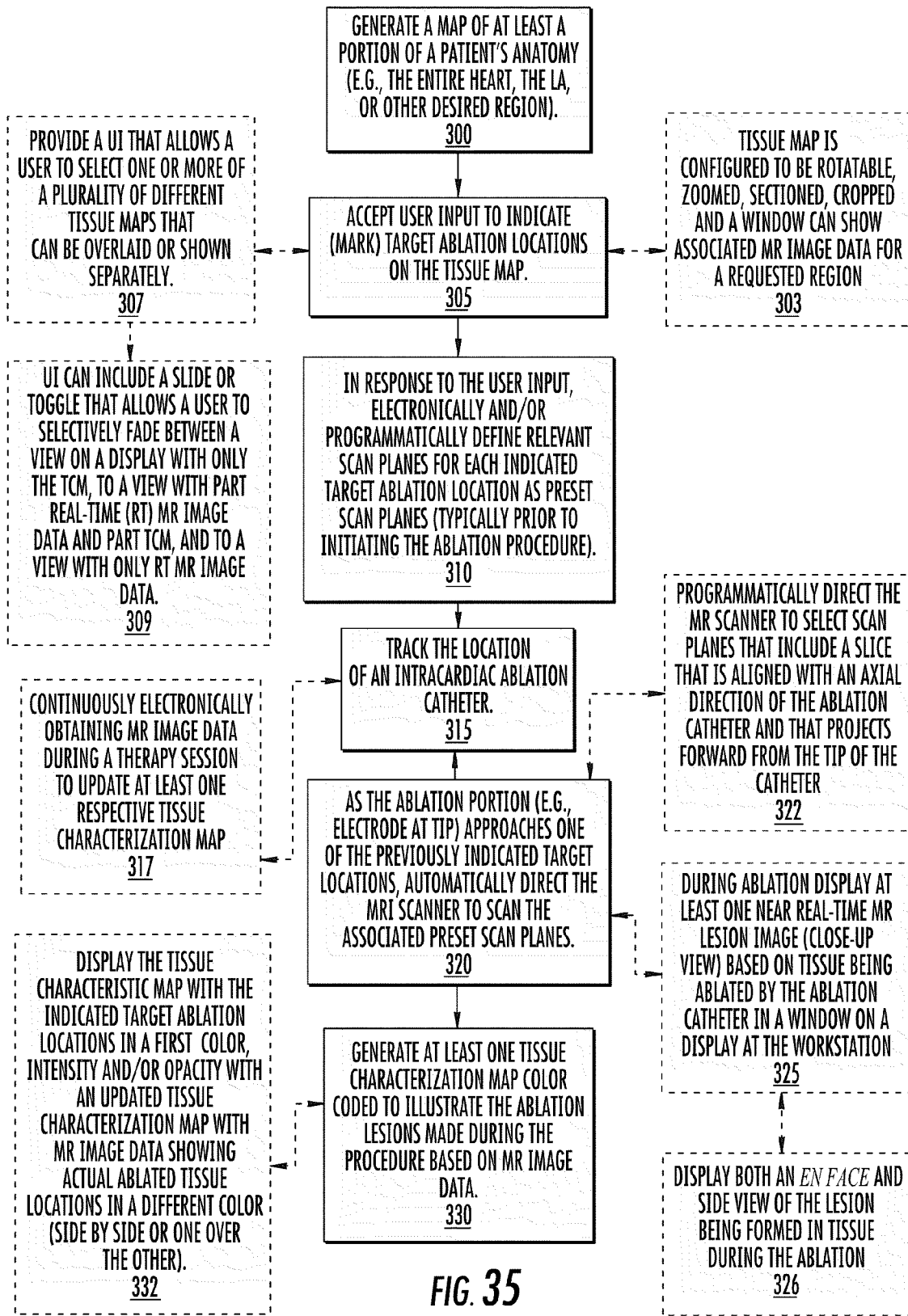
FIG. 35 is a flow chart of exemplary operations that can be used to carry out additional aspects of embodiments of the present invention.

FIGS. 34 and 35 are flow charts of steps that can be implemented to carry out embodiments of the present invention. Although the steps are shown in a particular order in these figures, neither the order of steps in these figures or the order of these figures is meant to indicate any required order in the implementation of one or more of the methods and/or method steps. Further, it will be appreciated that certain of the steps can be carried out simultaneously rather than serially and the blocks are stated for ease of discussion rather than as a limitation on how or when the operations are carried out.

A flexible intrabody medical device is introduced into a natural lumen or cavity of a patient during an MRI-guided procedure (block 200). Tracking signals are electronically obtained from tracking coils connected to an MR Scanner and attached to the flexible intrabody device during the MRI-guided procedure. The intrabody device has a distal end portion that can take on a curvilinear shape as it moves into position in the patient's body (block 202). X, Y, Z coordinate locations are electronically identified in 3-D MRI image space for each of the tracking coils using the tracking signals (block 204). MR image data are obtained and near RT MR images of the patient are generated during the MRI-guided procedure (block 206). A pre-acquired 3-D volumetric model of target anatomy of the patient is obtained and registered to the 3-D image space (block 208). Near real time (RT) visualizations of the medical device are generated showing: (a) the model of the patient's anatomy; (b) a physical representation of at least a distal end portion of the medical device using the identified locations of the tracking coils; and (c) at least one of the near RT MR images (block 210).

Optionally, a tip location and/or a device-tissue interface location proximate a tip location of the device in the three dimensional image space is electronically calculated using the identified locations of the tracking coils. The calculating step may project axially forward a defined distance (e.g., between about 0-4 mm, typically between about 0-2 mm) beyond the tip to define the device-tissue interface and at least one scan plane used to obtain the MR image data for the near RT images during and/or proximate in time to delivery of a therapeutic treatment and/or a diagnostic procedure is electronically defined using the calculated location (block 212). A user (via a UI) may be able to select the desired projection forward distance for the scan plane/slice location. The system may include a default distance (e.g., the end of the tip or distance forward=about 0 or 0.1 mm) that can be adjusted prior to or during a procedure.

Optionally, the visualizations can be electronically rotated based on user input and electronically selectively altering a view of the displayed visualization based on user input so that the visualization includes the at least one flexible device with (a) only a near RT image of the target anatomy, (b) both the near RT image of the anatomy and the registered model of the anatomical structure, or (c) only the registered model of the anatomical structure (block 214).

As shown in FIG. 35, at least one tissue characterization map or data therefrom can be electronically (programmatically) generated to render and display at least a portion of a patient's heart (e.g., the entire heart, the LA, or other desired region) (block 300). Optionally, the tissue characterization map is configured to be rotatable, zoomed, sectioned, cropped and a window can show associated MR image data for a requested region (block 303). User input can be accepted to indicate (mark) target ablation locations on the tissue characterization map or an EA map registered to image space (block 305). Optionally, a UI can allow a user to select a plurality of different tissue characterization maps that can be overlaid or shown separately or merged into a composite map (block 307). In response to the user input, the system can electronically and/or programmatically define relevant scan planes for each indicated target ablation location as preset scan planes (typically prior to initiating the ablation procedure) (block 310). The preset scan planes are for generating real time MRI when the ablation catheter is at the corresponding site. Although, the preset scan planes are described as defined by a UI that allows a clinician/physician to mark/indicate target ablation sites on a tissue characterization map, it is contemplated that the planning map can be another type of map, such as, for example, an electroanatomical map registered to the anatomical space.

In some embodiments, the UI can include a slide or toggle or other input means that allows a user to selectively fade between a view on a display with only the tissue characterization map, to a view with part Real-Time (RT) MR image data and part tissue characterization map and to a view with only RT MR image data (block 109) on the same viewing window.

During a procedure, the location of an intracardiac ablation catheter can be shown with respect to the registered map (block 315). Optionally, MR image data can substantially continuously be electronically obtained and used to update one or more respective tissue characterization maps during a therapy session (block 317). As the ablation portion of the catheter (e.g., electrode at tip) approaches one of the previously indicated target locations, the MRI Scanner is directed to scan ("snap to") the associated preset scan planes (block 320). Optionally, the MR Scanner can be programmatically directed to select scan planes that includes a slice that is aligned with an axial direction of the ablation catheter and that projects forward from the tip of the catheter (block 322). Also optionally, during ablation at least one real-time MR lesion image (close-up view) can be displayed based on tissue being ablated by the ablation catheter in a window on a display at the workstation (block 325). This may be a high resolution image of the local tissue using an internal receive antenna. Optionally, during the ablation, both an en face and side view of the lesion being formed in tissue can be displayed (block 326).

At least one tissue characterization map can be generated and displayed, color coded to illustrate the ablation lesions made during the procedure based on MR image data (block 330). Optionally, the tissue characterization map can be displayed with the (planned) indicated target ablation locations in a first color, intensity and/or opacity along with an updated tissue characterization map with MR image data showing actual ablated tissue locations in a different color (side by side or one over the other) (block 332).

Although described primarily herein with respect to Cardiac EP procedures using ablation electrodes, other ablation techniques can be used, such as, for example, laser ablation, thermal (heated liquid) ablation and cryoablation. Where used, the ablation catheter 80a can be an RF ablation catheter but can also or alternatively be configured to apply other ablations including cryogenic (e.g., cryoablation usually via an inflatable cryoballoon), laser, microwave, and even chemical ablation. In some embodiments, the ablation can be carried out using ultrasound energy. In particular embodiments, the ablation may be carried out using HIFU (High Intensity Focused Ultrasound). When MRI is used this is sometimes called Magnetic Resonance-guided Focused Ultrasound, often shortened to MRgFUS. This type of energy using a catheter to direct the energy to the target tissue can heat the tissue to cause necrosis.

Similarly, the systems and components can be useful for other MRI guided surgical intervention procedures, including, for example, delivering biologics or other drug therapies to target locations in cardiac or other tissue using MRI.

Some interventional tools may include an MRI receive antenna for improved SNR of local tissue. In some embodiments, the antenna has a focal length or signal-receiving length of between about 1-5 cm, and typically is configured to have a viewing length to receive MRI signals from local tissue of between about 1-2.5 cm. The MRI antenna can be formed as comprising a coaxial and/or triaxial antenna. However, other antenna configurations can be used, such as, for example, a whip antenna, a coil antenna, a loopless antenna, and/or a looped antenna. See, e.g., U.S. Pat. Nos. 5,699,801; 5,928,145; 6,263,229; 6,606,513; 6,628,980; 6,284,971; 6,675,033; and 6,701,176, the contents of which are hereby incorporated by reference as if recited in full herein. See also U.S. Patent Application Publication Nos. 2003/0050557; 2004/0046557; and 2003/0028095, the contents of which are also hereby incorporated by reference as if recited in full herein. Image data can also include image data obtained by a trans-esophageal antenna catheter during the procedure. See, e.g., U.S. Pat. No. 6,408,202, the contents of which are hereby incorporated by reference as if recited in full herein.

As discussed above, embodiments of the present invention may take the form of an entirely software embodiment or an embodiment combining software and hardware aspects, all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices. Some circuits, modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller. Embodiments of the present invention are not limited to a particular programming language.

Computer program code for carrying out operations of data processing systems, method steps or actions, modules or circuits (or portions thereof) discussed herein may be written in a high-level programming language, such as Python, Java, AJAX (Asynchronous JavaScript), C, and/or C++, for development convenience. In addition, computer program code for carrying out operations of exemplary embodiments may also be written in other programming languages, such as, but not limited to, interpreted languages. Some modules or routines may be written in assembly language or even micro-code to enhance performance and/or memory usage. However, embodiments are not limited to a particular programming language. It will be further appreciated that the functionality of any or all of the program modules may also be implemented using discrete hardware components, one or more application specific integrated circuits (ASICs), or a programmed digital signal processor or microcontroller. The program code may execute entirely on one (e.g., a workstation computer or a Scanner's computer), partly on one computer, as a stand-alone software package, partly on the workstation's computer or Scanner's computer and partly on another computer, local and/or remote or entirely on the other local or remote computer. In the latter scenario, the other local or remote computer may be connected to the user's computer through a local area network (LAN) or a wide area network (WAN), or the connection may be made to an external computer (for example, through the Internet using an Internet Service Provider).

The present invention is described in part with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing some or all of the functions/acts specified in the flowchart and/or block diagram block or blocks.

The flowcharts and block diagrams of certain of the figures herein illustrate exemplary architecture, functionality, and operation of possible implementations of embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order or two or more blocks may be combined, depending upon the functionality involved.

The workstation 60 and/or interface 44, 84, or patch bay, may also include a decoupling/tuning circuit that allows the system to cooperate with an MRI scanner 10S and filters and the like. See, e.g., U.S. Pat. Nos. 6,701,176; 6,904,307 and U.S. Patent Application Publication No. 2003/0050557, the contents of which are hereby incorporated by reference as if recited in full herein.

In some embodiments, the intrabody device 80 is configured to allow for safe MRI operation so as to reduce the likelihood of undesired deposition of current or voltage in tissue (inhibit or prevent undesired heating). The device 80 can include RF chokes such as a series of axially spaced apart Balun circuits or other suitable circuit configurations. See, e.g., U.S. Pat. No. 6,284,971, the contents of which are hereby incorporated by reference as if recited in full herein, for additional description of RF inhibiting coaxial cable that can inhibit RF induced current. The conductors connecting electrodes or other components on or in the catheter (or other interventional device) can also include a series of back and forth segments (e.g., the lead can turn on itself in a lengthwise direction a number of times along its length) and/or include high impedance circuits. See, e.g., U.S. patent application Ser. Nos. 11/417,594; 12/047,602; and 12/090,583, the contents of which are hereby incorporated by reference as if recited in full herein.

Although not shown, in some embodiments, the device can be configured with one or more lumens and exit ports and can be used and/or deliver desired cellular, biological, and/or drug therapeutics to a target area.

Figure 36:
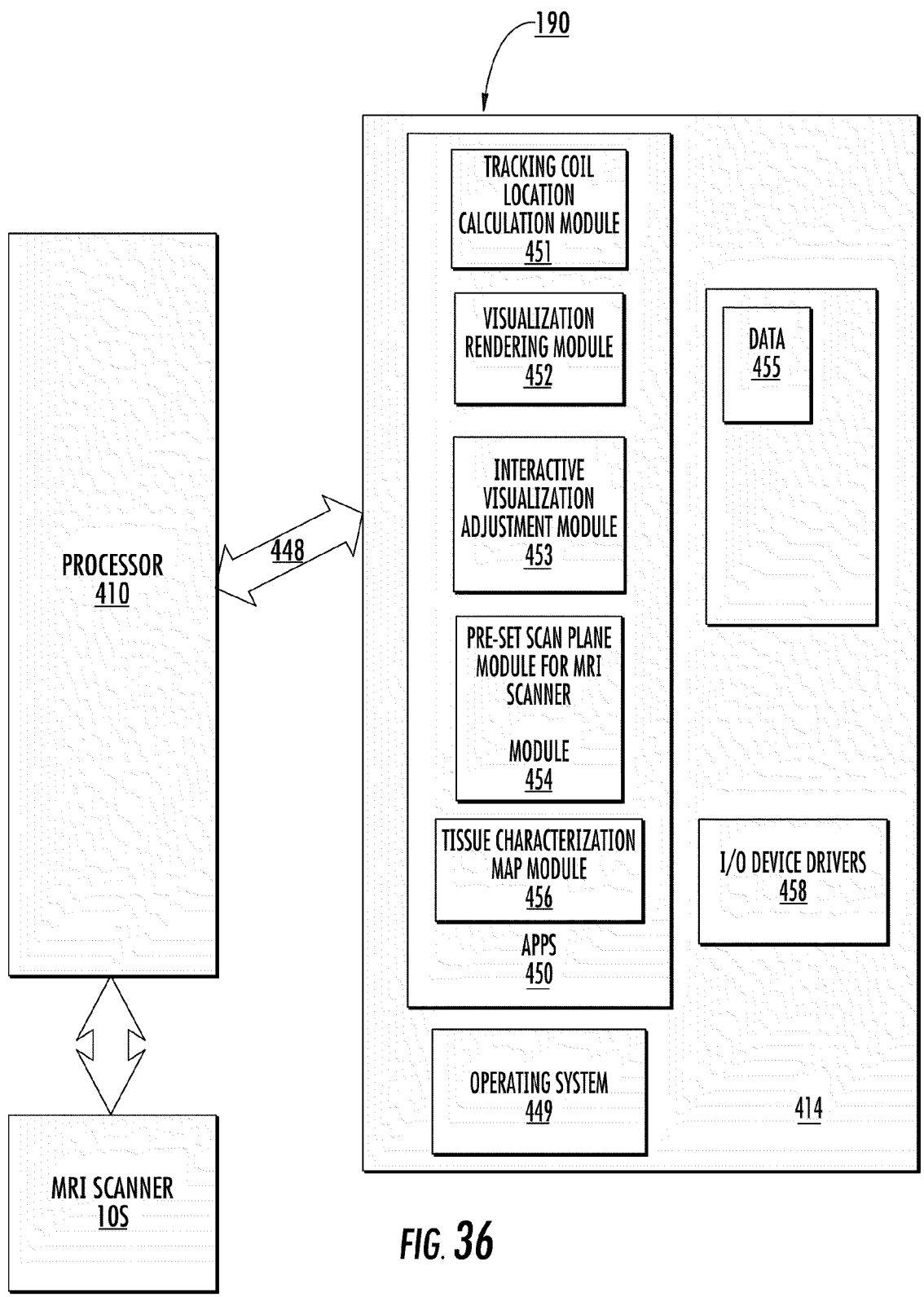
FIG. 36 is a schematic illustration of a data processing circuit or system according to embodiments of the present invention.

FIG. 36 is a schematic illustration of a circuit or data processing system that can be used with the system 10. The circuits and/or data processing systems 190 may be incorporated in a digital signal processor in any suitable device or devices. As shown in FIG. 36, the processor 410 communicates with and/or is integral with an MRI scanner 10S and with memory 414 via an address/data bus 448. The processor 410 can be any commercially available or custom microprocessor. The memory 414 is representative of the overall hierarchy of memory devices containing the software and data used to implement the functionality of the data processing system. The memory 414 can include, but is not limited to, the following types of devices: cache, ROM, PROM, EPROM, EEPROM, flash memory, SRAM, and DRAM.

FIG. 36 illustrates that the memory 414 may include several categories of software and data used in the data processing system: the operating system 449; the application programs 450; the input/output (I/O) device drivers 458; and data 456. The data 456 can also include device (ablation catheter) dimensions (e.g., distance of a tracking coil to the tip) and patient-specific image data 455. FIG. 36 also illustrates the application programs 454 can include a Tracking Coil Location Identification Calculation Module 451, a Visualization Rendering Module 452, an Interactive Visualization (and UI) Module 453, a Tissue Characterization Map Module 456, and a Pre-Set Scan Plane to Target Ablation Site Module 454, a and a UI Interface Module 453.

As will be appreciated by those of skill in the art, the operating systems 449 may be any operating system suitable for use with a data processing system, such as OS/2, AIX, or zOS from International Business Machines Corporation, Armonk, N.Y., Windows CE, Windows NT, Windows95, Windows98, Windows2000, WindowsXP, Windows Visa, Windows7, Windows CE or other Windows versions from Microsoft Corporation, Redmond, Wash., Palm OS, Symbian OS, Cisco IOS, VxWorks, Unix or Linux, Mac OS from Apple Computer, LabView, or proprietary operating systems. For example, VxWorks which can run on the Scanner's sequence generator for precise control of pulse sequence waveform timings.

The I/O device drivers 458 typically include software routines accessed through the operating system 449 by the application programs 450 to communicate with devices such as I/O data port(s), data storage 456 and certain memory 414 components. The application programs 450 are illustrative of the programs that implement the various features of the data processing system and can include at least one application, which supports operations according to embodiments of the present invention. Finally, the data 456 represents the static and dynamic data used by the application programs 450, the operating system 449, the I/O device drivers 458, and other software programs that may reside in the memory 414.

While the present invention is illustrated, for example, with reference to the Modules 451, 452, 453, 454, 456 being application programs in FIG. 35, as will be appreciated by those of skill in the art, other configurations may also be utilized while still benefiting from the teachings of the present invention. For example, the Modules and/or may also be incorporated into the operating system 449, the I/O device drivers 458 or other such logical division of the data processing system. Thus, the present invention should not be construed as limited to the configuration of FIG. 36 which is intended to encompass any configuration capable of carrying out the operations described herein. Further, one or more of modules, i.e., Modules 451, 452, 453, 454, 456 can communicate with or be incorporated totally or partially in other components, such as separate or a single processor, an MRI scanner 10S or workstation 60.

The I/O data port can be used to transfer information between the data processing system, the workstation, the MRI scanner, and another computer system or a network (e.g., the Internet) or to other devices controlled by the processor. These components may be conventional components such as those used in many conventional data processing systems, which may be configured in accordance with the present invention to operate as described herein.

Non-Limiting Examples of Tissue Characterization Maps will be discussed below.

Thermal Tissue Characterization Map

The thermal tissue characterization map can be based on thermal status at a given point in time or may be provided as a composite of heating of different tissue locations at different times (e.g., during and/or after ablation of different points at different times of the ablation procedure). The thermal map can be registered to a location of the internal ablation catheter (e.g., tip) at different times so that the location of the ablation catheter tip is correlated to the thermal activity/status at that location at that time as that is the time frame that the image data for that region illustrating increased thermal activity/heating is generated. That is, the image scan planes are taken to show the tissue at the location of the ablation catheter tip. The image scan planes are typically projected forward a known distance from the tracking coil so that the lesion tissue in front of the ablation tip is imaged.

The MR thermal data can be obtained using temperature imaging techniques (MR thermometry) to show temperature or phase variance. Examples of pulse sequences include, for example, SSFP and 2D GRE.

Vasculature Tissue Characterization Map

Segmented MRA (Magnetic Resonance Angiography) imaging volumes of a patient can be used to generate a vasculature tissue characteristic map which may indicate areas of increased blood flow and/or larger and smaller channels within the vasculature structure.

Fibrous Tissue Characterization Map

Contrast-based or non-contrast based MRI images of the patient can identify fibrous tissue in target tissue (e.g., the heart).

Contrast-Based Tissue Characterization Maps

Tissue damage can be shown or detected using MR image data based on contrast agents such as those agents that attach to or are primarily retained in one of, but not both, healthy and unhealthy tissue, e.g., the contrast agent is taken up by, attaches to, or resides or stays in one more than in the other so that MR image data will visually identify the differences (using pixel intensity). The contrast agent can be one or more of any known or future developed biocompatible agent, currently typically gadolinium, but may also include an antibody or derivative or component thereof that couples to an agent and selectively binds to an epitope present in one type of tissue but not the other (e.g., unhealthy tissue) so that the epitope is present in substantially amounts in one type but not the other. Alternatively, the epitope can be present in both types of tissue but is not susceptible to bind to one type by steric block effects.

A tissue characteristic map registered to the imaging space can allow a clinician to assess both scar formation (isolation of the PV) and the volume of enhancement on a LA myocardial volume may indicate a poor outcome prediction and a clinician may decide to continue ablating or alter the ablation location or protocol (e.g., drive a clinical decision).

Examples of pulse sequences that can be used for delayed hyper-enhancement MRI include, for example, gradient echo, SSFP (steady state free precession) such as TrueFISP on Siemens MRI Scanners, FIESTA on GE MRI Scanners, and b-FFE on Philips MRI Scanners.

Edema Tissue Characterization Maps

After (and/or during) ablation, tissue will typically have edema. This can be detected in MRI using, for example, pulse sequences such as T2-weighted Turbo-Spin-Echo, HASTE (a Siemens term), SSFP, or T2-weighted gradient recalled echo (GRE).

Some tissue characterization maps may show edema and thermal maps overlaid or otherwise combined as a composite map that can be used to evaluate a procedure. For example, to visually assess whether there is complete or incomplete scar formation to isolate pulmonary veins. It is believed that complete scar formation to isolate PV is associated with a better prognosis for AFIB.

Heart Wall Motion Tissue Characterization Maps

MRI can be used to assess heart wall motion. Abnormal motion can be visually indicated on the tissue characterization map. Examples of pulse sequences that may be used to determine heart wall motion include, for example, DENSE, HARP and MR tagging.

Thus, it will be appreciated that embodiments of the present invention are directed to systems, including hardware and/or software and related methodology to substantially continuously collect and construct, throughout an MRI-guided cardiac procedure, e.g., an MRI-guided procedure, a patient-specific anatomical tissue characterization map or associated data that can be shown on a map of a target anatomical structure/region (e.g., a chamber of the heart such as the atrium). Embodiments of the system can generate and show in pre-set views and in near-real time during the procedure tissue while it is being treated, e.g., ablated.

While embodiments have been primarily discussed with respect to an MRI-guided cardiac system, the system can be used for other anatomical regions and deliver or apply other therapies as well as for diagnostic procedures. For example, the esophagus and anatomy near the esophagus, e.g., the aorta, coronary arteries, mediastinum, the hepaticobiliary system or the pancreas in order to yield anatomic information about the structures in those areas, "pancreaticohepaticobiliary" structures (collectively the structures of the liver, gallbladder, bile ducts and pancreas), the tracheobronchopulmonary structure (structures including the lungs and the tracheobronchial tree), the nasopharynx system (e.g., a device introduced transnasally may be adapted for evaluating the arterial circle of Willis and related vascular structures for abnormalities, for example congenital or other aneurysms), the proximal aerodigestive system or the thyroid, the ear canal or the Eustachian tube, permitting anatomic assessment of abnormalities of the middle or inner ear, and further permitting evaluation of adjacent intracranial structures and lesions.

The systems and methods of the present invention may be particularly useful in those lesions whose extent is not readily diagnosed, such as basal cell carcinomas. These lesions may follow nerves into the orbit or into the intracranial area, extensions not evident with traditional imaging modalities to the surgeon undertaking the resection to provide real time information to the resecting surgeon or the surgeon performing a biopsy as to the likely areas of lymph node invasion.

It is also contemplated that the systems can be used in the "head and neck" which refers collectively to those structures of the ear, nose and throat and proximal aerodigestive system as described above, traditionally falling within the province of otorhinolaryngology. The term "head and neck," as used herein, will further include those structures of the neck such as the thyroid, the parathyroid, the parotid and the cervical lymph nodes, and will include also the extracranial portions of the cranial nerves, including but not limited to the facial nerve, this latter nerve being included from its entry into the internal auditory meatus outward. The term "head and neck, as used herein, will also include those structures of the orbit or of the globe, including the oculomotor muscles and nerves, lacrimal glands and adnexal structures. As used herein, the term "head and neck" will further include those intracranial structures in proximity to the aforesaid head and neck structures. These intracranial structures may include, as examples, the pituitary gland, the pineal gland, the nuclei of various cranial nerves, the intracranial extensions of the cranial nerves, the cerebellopontine angle, the arterial circle of Willis and associated vascular structures, the dura, and the meninges.

In yet other embodiments, the systems can be used in the genitourinary system, such as the urethra, prostate, bladder, cervix, uterus, and anatomies in proximity thereto. As used herein, the term "genitourinary" shall include those structures of the urinary tract, the male genital system and the female genital system. The urinary tract structures include the urethra, the bladder, the ureters, the kidney and related neural, vascular, lymphatic and adnexal structures. The male genital tract includes the prostate, the seminal vesicles, the testicles, the epididymis and related neural, vascular, lymphatic, ductal and adnexal structures. The female genital tract includes the vagina, the cervix, the non-gravid and gravid uterus, the fallopian tubes, the ovaries, the ova, the fertilized egg, the embryo and the fetus. The term "genitourinary" further refers to those pelvic structures that surround or support the abovementioned structures, such as the paraurethral tissues, the urogenital diaphragm or the musculature of the pelvic floor. The devices can be configured for transurethral placement for evaluation and treatment of female urinary incontinence or bleeding and may use high resolution images of the local tissue, e.g., different layers of the paraurethral tissues. It is understood, for example, that a clearly identified disruption in the muscle layers surrounding the urethra may be repaired surgically, but also must be guided by detailed anatomic information about the site of the abnormality. The devices may also be configured for placement in the genitourinary system such as into the ureter or renal pelvis, urinary tract, or transvaginal use in analysis of the vagina and anatomies in proximity thereto. For example, transvaginal or transcervical endouterine placement may be useful in the diagnosis of neoplasia, in the diagnosis and treatment of endometriosis and in the evaluation of infertility or diagnosis, treatment of pelvic disorders resulting in pelvic pain syndromes, evaluation/treatment of cervical and uterine malignancies and to determine their stages, obstetric use such as permitting anatomic evaluation of mother and fetus.

In another embodiment, the systems can be used for evaluating and/or treating the rectum or colon, typically by the transrectal route that can be inserted through the anus to a level within the rectum, sigmoid or descending colon where the designated anatomy can be visualized. For example, this approach may be used to delineate the anatomy of the prostate gland, and may further guide the biopsy or the extirpation of lesions undertaken transrectally or transurethrally.

In other embodiments, the systems and methods of the present invention may be used for the evaluation, diagnosis or treatment of a structure in the gastrointestinal system, or for the evaluation, diagnosis or treatment of a region of the gastrointestinal anatomy. As used herein, the term "gastrointestinal" shall include structures of the digestive system including the esophagus, the stomach, the duodenum, jejunum and ileum (small intestine), the appendix and the colon. The term "gastrointestinal anatomy" shall refer to the structures of the gastrointestinal system as well as the surrounding supporting structures such as the mesentery and the enclosing structures such as the peritoneum, the diaphragm and the retroperitoneum. Disorders of the gastrointestinal system are well-known in the medical arts, as are disorders of the gastrointestinal anatomy. In an exemplary embodiment, the intrabody device may be passed into the stomach.

In other embodiments, the systems and methods of the present invention may be used for the evaluation, diagnosis and treatment of the vascular system. The vascular system is understood to include the blood vessels of the body, both arterial and venous. The vascular system includes both normal and abnormal blood vessels, named and unnamed vessels, and neovascularization. Access to the vascular system takes place using techniques familiar to practitioners of ordinary skill in the art. The present invention may be used in blood vessels of all size and the intrabody devices may be dimensionally adapted to enter smaller caliber vessels, such as those comprising the distal coronary circulation, the intracranial circulation, the circulation of the distal extremities or the distal circulation of the abdominal viscera. According to these systems and methods, furthermore, positioning a device within the vascular system may be useful for evaluating, diagnosing and treating conditions in structures adjacent to or in proximity to the particular vessel within which the device is situated. Such structures are termed "perivascular structures." As an example, a device placed within a coronary artery may provide information about the vessel itself and about the myocardium that is perfused by the vessel or that is adjacent to the vessel. A device thus positioned may be able to guide therapeutic interventions directed to the myocardial tissue, and may also be able to guide endovascular or extravascular manipulations directed to the vessel itself. It will be readily appreciated by those of ordinary skill in the art that a number of other applications exist or may be discovered with no more than routine experimentation using the systems and methods of the present invention within the vascular system.

It is understood that access to anatomic structures using the systems, devices modified to fit the intended purpose and anatomy, and methods of the present invention may be provided via naturally occurring anatomic orifices or lumens, as indicated in the examples above. It is further understood, however, that access to anatomic structures using these systems and methods may be additionally provided using temporary or permanent orifices that have been created medically.

Further, the methods and systems may cooperate with robotic driven systems rather than manual systems.

The aforesaid embodiments are understood to be exemplary only. Other embodiments wherein devices may be used within body areas such as body canals, cavities, lumens, passageways, actual or potential spaces will be apparent to practitioners of ordinary skill in the relevant arts In the drawings and specification, there have been disclosed embodiments of the invention and, although specific terms are employed, they are used in a generic and descriptive sense only and not for purposes of limitation, the scope of the invention being set forth in the following claims. Thus, the foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A circuit for an MRI-guided cardiac interventional system, comprising:
  at least one processor configured to: (a) generate near real time (RT) MRI images of at least a portion of a heart of a patient using relevant anatomical scan planes associated with a 3-D MRI image space having a coordinate system; (b) identify coordinates in the 3-D MRI image space coordinate system associated with a location of at least a distal end portion of at least one flexible intrabody catheter in the 3-D MRI image space using tracking coil data from a plurality of longitudinally spaced apart tracking coils on the distal end portion of the at least one flexible intrabody catheter; and (c) render interactive near RT visualizations with MR image data and at least the distal end portion of the at least one flexible intrabody catheter shown with a three-dimensional physical representation; and
  at least one display in communication with the at least one processor configured to display the rendered interactive near RT visualizations,
  wherein the at least one processor is configured to direct an MRI scanner to generate a tracking sequence and an imaging sequence, the imaging sequence using the anatomical scan planes used to generate the near RT MRI images, wherein the tracking sequence is carried out independent of the imaging sequence, wherein the tracking sequence generates X, Y, Z coordinates of the tracking coils of the distal end portion of the flexible catheter from signals from different MR scanner channels associated with coaxial cables from the tracking coils of the at least one flexible intrabody catheter which, during operation, are connected to the different channels of the MR scanner, wherein the at least one processor is configured to generate the three dimensional physical representation of at least the distal end of the flexible catheter showing orientation and shape using the X, Y and Z coordinates of the tracking coils and pre-defined information of the at least one flexible intrabody catheter including a distance to a tip of the at least one flexible intrabody catheter from one or more of the tracking coils and a spatial relationship of the tracking coils to select relevant anatomical scan planes for the near RT MRI images that can include scan volumes that exclude the catheter, wherein the at least one processor is configured to calculate a location in the 3-D MRI image space coordinate system associated with the tip and/or distal end portion of the at least one flexible intrabody catheter using the tracking coil data to identify at least one of the relevant anatomical scan planes, wherein the at least one processor is configured to calculate a catheter-tissue interface location proximate the tip of the at least one flexible intrabody catheter in the 3-D MRI image space using the X, Y, Z coordinates of locations of the tracking coils, wherein the calculation is carried out to place the catheter tissue interface location a distance of between about 0-5 mm beyond a calculated location of the tip of the at least one flexible intrabody catheter, and wherein the calculated catheter-tissue interface is either (a) calculated to be tangent and substantially in-line with at least two of the tracking coils or (b) calculated as a plane in the 3-D MRI image space proximate a projected plane defined by at least three points associated with three different ones of the tracking coils.

2. The circuit of claim 1, , wherein the at least one processor is further configured to provide a window on the at least one display of the catheter-tissue interface, the window providing near RT high resolution MRI images separate from the visualizations, and wherein the visualizations are provided in an adjacent separate window on the at least one display.

3. The circuit of claim 1, wherein the at least one processor is further configured to provide a patient planning map with at least one target treatment site identified thereon registered to the 3-D MRI image space.

4. The circuit of claim 3 wherein the at least one display comprises a User Interface that allows a user to select whether to show the at least one target treatment site in the visualizations so that: (i) the at least one treatment site is shown with the near RT MRI images without the planning map or with the planning map faded relative to the at least one treatment site and near RT MRI images; or (ii) the at least one treatment site is shown with the planning map and with the near RT MRI images.

5. The circuit of claim 1, further comprising the at least one flexible intrabody catheter, and wherein the at least one processor is configured to generate the physical representation of at least the distal end portion of the at least one flexible intrabody catheter in the visualizations based on the pre-defined information that includes the following: (i) known or predictable shape variation of the distal end portion of the at least one flexible intrabody catheter; and (ii) the spatial relationship of the tracking coils.

6. The circuit of claim 1, further comprising the at least one flexible intrabody catheter and the MRI Scanner, wherein the at least one processor is in communication with and/or integral with the MRI Scanner, and wherein the MRI Scanner interleaves obtaining tracking coil data with image data to generate the interactive visualizations with the physical representations of at least the distal end portion of the at least one flexible intrabody catheter.

7. The circuit of claim 1, wherein the at least one display comprises a User Interface, and wherein the User Interface is configured to allow a user to selectively fade and/or turn on and off tissue characterization and/or electroanatomical data in at least one visualization either or both: (a) on a three dimensional pre-acquired model of a patient's heart in the visualizations, the pre-acquired model shown in and/or registered to the 3-D imaging space; and/or (b) in the near RT MR images without the pre-acquired model.

8. The circuit of claim 1, wherein the at least one display comprises a User Interface, and wherein the User Interface is configured to allow a user to (i) selectively fade and/or turn on and off tissue characterization data and/or electroanatomical data in the visualizations and (ii) to show the tissue and/or electroanatomical data only with the near RT MRI images in the visualizations or with a model and the near RT MRI images in the visualizations.

9. The circuit of claim 1, wherein the tracking coils comprise at least three closely spaced apart tracking coils on the distal end portion of the at least one flexible catheter, wherein the three-dimensional physical representation is an electronically generated physical representation of a physical configuration in an intrabody shape and orientation of at least a distal end portion of the at least one flexible intrabody catheter.

10. The circuit of claim 1, wherein the at least one processor is configured to present a 3-D volumetric model of at least a portion of the patient's heart in the rendered visualizations with the 3-D volumetric model registered to the 3-D MRI image space along with the physical representation of at least the distal end portion of the at least one flexible intrabody catheter in the 3-D MRI image space.

11. The circuit of claim 10 , wherein the at least one display comprises a User Interface, the User Interface configured to allow a user to alter a respective displayed visualization to include only a near RT MRI image of the anatomy, to include the near RT MRI image of the anatomy and the registered 3-D volumetric model of the heart, or to include only the registered 3-D volumetric model of the heart.

12. The circuit of claim 10, wherein the at least one display comprises a User Interface, and wherein the at least one processor is configured to show the 3-D volumetric model in the visualizations in one of a plurality of different selectable ways including at least two of: a cutaway, wireframe, translucent, color-coded or opaque configuration, according to user input using the User Interface.

13. The circuit of Claim 10, wherein the at least one display comprises a User Interface, and wherein the at least one processor is configured to allow a user to manipulate the visualizations using the User Interface including to: rotate, crop or zoom the 3-D volumetric model in a respective visualization, and wherein the at least one processor automatically selects anatomically relevant scan planes to obtain MR image data in response thereto.

14. The circuit of claim 1, wherein the at least one processor is configured to render the visualizations with the three dimensional physical representation to show a location of the tip of the at least one flexible intrabody catheter with a first three-dimensional shape and to show each tracking coil on the distal end portion with a second different three dimensional shape or shapes and a color, with each tracking coil having a respective different color from the other tracking coils, and connect the tip and the coil shapes with a line or a spline.

15. The circuit of claim 1, wherein the at least one processor is configured to generate the visualizations with at least two visual reference planes that are oblique or orthogonal to each other.

16. The circuit of claim 15, wherein the at least one display comprises a User Interface, and wherein the two planes are transparent and/or translucent with different color perimeters and can move relative to and/or be locked to an anatomical model shown in the visualizations, and wherein the User Interface is configured to allow a user to rotate the model and move the reference planes to change the view of anatomy shown in the visualizations.

17. The circuit of claim 1, wherein the at least one display comprises a User Interface, the User Interface configured to allow a user to fade the three dimensional physical representation of the at least one flexible intrabody catheter in the visualizations on the at least one display from a near real-time MR image of the heart.

18. The circuit of claim 1, wherein the at least one processor is configured to show a volumetric patient anatomical model of at least a portion of the heart and at least two orthogonal or oblique intersecting reference planes in the 3-D MRI image space in the visualizations, the reference planes intersecting and extending across the volumetric patient anatomical model and the near RT MRI images, wherein the reference planes align with the relevant anatomical scan planes.

19. The circuit of claim 1, further comprising at least one flexible intrabody catheter, wherein one of the at least one flexible intrabody catheter is a therapeutic catheter including at least one of an injection or ablation catheter with a catheter tip portion as the distal end portion of the catheter with the tip used by the at least one processor to calculate the catheter-tissue interface, wherein the at least one display comprises a close-up viewing window to show near RT MRI images of ablation lesion forming or injection delivery, and wherein at least some of the images in the close-up viewing window are generated using high-resolution MR image data.

20. The circuit of claim 1, wherein the at least one display comprises a User Interface, and wherein the User Interface is configured to allow a user to select a dimensional offset of between about 0-5 mm for the catheter-tissue interface, and wherein the at least one processor uses the calculated catheter-tissue interface location with the selected offset to automatically define at least one scan plane as at least one of the anatomical relevant scan planes used to obtain the MR data for the near RT MR images.

21. The circuit of claim 1, wherein the at least one processor calculates a scan plane location for an en face view at the catheter-tissue interface that is projected to be substantially parallel to tissue proximate the catheter-tissue interface for at least some of the near RT MRI images.

22. The circuit of claim 1, wherein the at least one processor is configured to direct an MRI Scanner to snap-to a projected tissue-device interface based on the calculated catheter-tissue interface for at least one of the relevant anatomical scan planes to obtain near RT MRI image data of the catheter-tissue interface.

23. The circuit of claim 1, wherein the at least one display comprises a User Interface, configured to allow a user to select different pre-acquired and/or in situ generated maps including at least two of the following for presentation of the selected map or data associated therewith on the at least one display, registered to or spatially aligned with the 3-D MRI image space:
  a thermal tissue characterization map;
  an edema tissue characterization map;
  a first delayed enhancement tissue characterization map;
  a second delayed enhancement tissue characterization map taken after the first delayed enhancement tissue characterization map;
  a hypoxic tissue characterization map;
  a vasculature tissue characteristic map;
  a fibrous tissue characteristic map;
  an ischemic tissue characterization map;
  a fluid distribution map;
  a light exposure map; and
  an electroanatomical map.

24. The circuit of claim 1, wherein the tracking sequence identifies the X, Y, Z coordinates of the tracking coils simultaneously.

25. The circuit of claim 1, wherein the tracking sequence dephases signal perpendicular to a read-out direction to attenuate unwanted signal from 1) bulk objects and 2) regions sensed by signal sensitive parts of the flexible catheter to thereby leave a sharp peak indicating position of the tracking coils, and wherein once a tracking sequence is complete, a spoiler gradient can be used to diphase any transverse signal remaining before the image sequence is executed.

26. The circuit of claim 1, wherein the tracking sequence comprises a plurality of small flip angle excitation with each repetition designed to indicate the X, Y or Z component of the tracking coil coordinates in succession.

27. An MRI guided system, comprising:
  an MRI Scanner;
  at least one flexible intrabody medical device configured to be introduced into a patient via a tortuous and/or natural lumen path, the at least one flexible intrabody medical device having tracking coils that are connected to channels of the MRI Scanner;
  a circuit comprising at least one processor adapted to communicate with and/or reside in the MRI Scanner, the circuit configured to: (a) obtain MR image data and generate a series of near real time (RT) MRI images of target anatomy of a patient during a surgical procedure using relevant anatomical scan planes associated with a 3-D MRI image space of the MRI Scanner, the 3-D MRI image space having a coordinate system; (b) identify a location of at least a distal end portion of the flexible intrabody medical device in the coordinate system of the 3-D MRI image space using tracking coil signal data from the tracking coils; and (c) render near RT interactive visualizations of the at least one flexible medical device in the 3-D image space with near RT image data of target patient anatomical structure and a registered pre-acquired first volumetric model of the target anatomical structure of the patient, wherein the circuit illustrates the at least one flexible medical device with a three-dimensional physical representation in the visualizations; and
  a display with a User Interface in communication with the circuit configured to display the visualizations during an MRI guided interventional procedure, wherein the User Interface is configured to allow a user to (a) rotate the visualizations and (b) alter a displayed visualization to include only a near RT image of target anatomy, to include the near RT image of the target anatomy and the registered model of the anatomical structure, or to include only the registered first volumetric model of the target anatomical structure, wherein the MRI Scanner is configured to interleave signal acquisition of image data with signal acquisition of tracking coil signals from the tracking coils, and wherein the circuit is configured to (i) electronically track the at least one flexible intrabody medical device in the 3-D MRI image space using the tracking coil signals independent of scan planes used to obtain the MR image data and to (ii) calculate a location in the 3-D MRI image space of a medical device-tissue interface associated with a tip and/or distal end portion of the at least one flexible intrabody medical device to identify at least one of the relevant anatomical scan planes, wherein the circuit is configured to calculate the location of the medical device-tissue interface using X, Y, Z coordinates of locations of the tracking coils and a known spatial relationship of the tracking coils, wherein the calculation is carried out to place the location of the device-tissue interface a distance of between about 0-5 mm beyond a calculated location of the tip of the at least one flexible intrabody medical device, and wherein the calculated medical device-tissue interface is either (a) calculated to be tangent and substantially in-line with at least two of the tracking coils or (b) calculated as a plane in the 3-D MRI image space proximate a projected plane defined by at least three points associated with three different ones of the tracking coils.

28. The system of claim 27, wherein the circuit automatically defines at least one of the relevant anatomical scan planes used to obtain the MR image data based on the calculated medical device tissue interface location during and/or proximate in time to delivery of a therapeutic treatment and/or a diagnostic procedure.

29. The system of claim 28, wherein the tracking coils comprise at least three spaced apart tracking coils, with at least two of the tracking coils being closely spaced together in fixed relationship on a rigid distal end portion of the flexible intrabody medical device proximate a distal tip thereof, and wherein the circuit is configured to direct the MR Scanner to snap-to the calculated medical device-tissue interface to obtain near real time image data for the near RT MRI images.

30. The system of claim 27, wherein the circuit is further configured to include a visualization shown on the display with at least one tissue characterization map.

31. The system of claim 30, wherein the at least one tissue characterization map data is color-coded to show either lesions associated with ablation sites created during a cardiac procedure or injection sites and associated fluid distribution from the injections during a cardiac procedure.

32. The system of claim 30, wherein the at least one flexible intrabody medical device is an ablation catheter, and wherein the at least one tissue characterization map or data therefrom is configured to show ablation lesion formation proximate a pulmonary vein whereby a clinician can evaluate whether an ablation therapy carried out using the ablation catheter has electrically isolated a pulmonary vein.

33. The system of claim 30, wherein the at least one flexible intrabody medical device is an injection catheter, and wherein the tissue characterization map or data is configured to show fluid distribution in cardiac tissue whereby a clinician can evaluate whether injections of a therapeutic using the injection catheter has generated a desired fluid distribution in cardiac tissue.

34. The system of claim 27, wherein the circuit is configured to provide to the display an electroanatomical (EA) map as the first volumetric model, the EA map imported from a different imaging modality and/or generated from MRI data in the 3-D MRI image space using a mapping catheter with tracking coils.

35. The system of claim 27, wherein the User Interface is configured to allow a user to selectively fade and/or turn at least one tissue characterization map or data therefrom on and off so that the at least one tissue characterization map or data therefrom is shown or not shown in the visualizations on the display.

36. The system of claim 35, wherein the at least one tissue characterization map includes at least two of the following:
a thermal tissue characterization map;
an edema tissue characterization map;
a first delayed enhancement tissue characterization map;
a second delayed enhancement tissue characterization map taken after the first delayed enhancement tissue characterization map;
a hypoxic tissue characterization map;
a vasculature map;
a fibrous tissue map;
an ischemic tissue characterization map;
a fluid distribution map; and
a light exposure map.

37. The system of claim 27, wherein the circuit is configured to allow a user via the User Interface to selectively fade and/or turn on and off tissue characterization data and/or electroanatomical data in the visualizations.

38. The system of claim 37, wherein the circuit is configured to allow a user via the User Interface to selectively fade and/or turn on and off data in the visualizations so that the display shows the tissue characterization data and/or electroanatomical data: (a) on the registered pre-acquired first volumetric model in the visualizations; or (b) in the near RT MR images alone without the first pre-acquired volumetric model.

39. The system of claim 27, wherein the circuit is configured to accept user input via the User Interface to selectively fade and/or turn on and off visual indications of target treatment sites in the visualizations.

40. The system of claim 27, wherein the circuit is configured to accept user input via the User Interface to selectively show on the display the target treatment sites in the visualizations as either: (a) target treatment sites on the registered pre-acquired first model with the near RT MRI images; or (b) in the near RT MR images without the registered pre-acquired first volumetric model.

41. The system of claim 27, wherein the tracking coils comprise at least three spaced apart tracking coils connected to respective channels of the MR Scanner, and wherein the circuit is configured to direct the MR Scanner to snap-to the medical device-tissue interface to use at least one scan plane associated therewith as at least one of the relevant anatomical scan planes to obtain near real time image data of the medical device-tissue interface for the near RT MRI images.

42. The system of claim 41, wherein the at least one flexible intrabody medical device includes at least one loop catheter with a distal loop end having the spaced apart tracking coils connected to respective channels of the MR Scanner, and wherein the circuit is configured to direct the MR Scanner to snap-to the calculated medical device-tissue interface, and wherein the calculated medical device-tissue interface is calculated as the plane in 3-D MRI image space proximate the projected plane defined by the at least three points associated with three different tracking coils on the distal loop end to obtain near real time image data of the medical device-tissue interface for the near RT MRI images.

43. The system of claim 41, wherein the at least one flexible intrabody medical device comprises a bendable or deflectable catheter, wherein the tracking coils comprise at least three spaced apart tracking coils on the bendable or deflectable catheter, and wherein the circuit is configured to direct the MR Scanner to snap-to the calculated medical device-tissue interface that is tangent and substantially in-line with the at least two of the tracking coils to obtain near real time image data of the medical device-tissue interface for the near RT MRI images.

44. The system of claim 41, wherein the tracking coils are spaced apart tuned tracking coils, each connected to a tuning circuit with a diode at a proximal end of the at least one flexible medical device using respective coaxial cables, wherein the coaxial cables each have an electrical length in the MR Scanner measured from the tracking coil to the diode that is about ¼ lambda or a higher odd harmonic thereof, and wherein the circuit is configured to identify a location of the tracking coils in the 3-D MRI image space with a precision of at least about 1 mm.

45. The system of claim 41, wherein the tracking coils are a plurality of spaced apart tuned tracking coils that are connected to a diode at a proximal end of the at least one flexible device using respective coaxial cables, wherein the coaxial cables each have an electrical length in the MR Scanner measured from the tracking coil to the diode that is about ¼ lambda or a higher odd harmonic thereof, and wherein the circuit is configured to obtain tracking coil signals from two adjacent tracking coils in a fixed spatial relationship with each other with respective tracking signals that define a correct physical offset distance.

46. An MRI guided cardiac intervention system, comprising:
   an MR Scanner having a plurality of channels;
   a plurality of flexible intrabody catheters, each having a plurality of tracking coils, each tracking coil of each flexible intrabody catheter connected to a different MR Scanner channel; and
   at least one display in communication with the MR Scanner,
   wherein the MR Scanner includes at least one circuit with at least one processor that is configured to: (a) generate near real time (RT) MRI images of at least a portion of a heart of a patient shown on the at least one display using relevant anatomical scan planes associated with a 3-D MRI image space having a coordinate system; (b) identify a location of at least a distal portion of the flexible intrabody catheters in the 3-D MRI image space using tracking coil signal data in the MRI image space coordinate system; (c) render dynamic near RT visualizations with physical three-dimensional representations of the flexible intrabody catheters in the 3-D image space with respect to a volumetric pre-acquired model of the patient's heart registered to the imaging space with the near RT MRI images shown on the at least one display, and (d) calculate a location in the 3-D MRI image space of a catheter-tissue interface associated with a tip and/or distal end portion of the at least one flexible intrabody catheter to identify at least one of the relevant anatomical scan planes,
   wherein the at least one circuit is configured to calculate the location of the catheter-tissue interface proximate the tip of one or more of the flexible intrabody catheters in the 3-D MRI image space using X, Y, Z coordinates of locations of the tracking coils, wherein the calculation is carried out to place the location of catheter-tissue interface a distance of between about 0-5mm beyond a calculated location of the tip of one or more of the flexible intrabody catheters, and wherein the calculated catheter-tissue interface location is either (a) calculated to be tangent and substantially in-line with at least two of the tracking coils or (b) calculated as a plane in the 3-D MRI image space proximate a projected plane defined by at least three points associated with three different ones of the tracking coils.

47. A system according to claim 46, wherein the at least one circuit is configured to show on the at least one display at least one of a plurality of user-selectable tissue characterization maps or data associated therewith on wherein the display is in communication with a User Interface that is configured to allow a user to selectively fade and/or turn one or more of the tissue characterization maps or data therefrom on and off, and wherein the tissue characterization maps include a plurality of the following:
   a thermal tissue characterization map;
   an edema tissue characterization map;
   a first delayed enhancement tissue characterization map;
   a second delayed enhancement tissue characterization map taken after the first delayed enhancement tissue characterization map;
   a hypoxic tissue characterization map;
   a vasculature map;
   a fibrous map;
   an ischemic tissue characterization map;
   a fluid distribution map; and
   a light exposure map.

48. The system of claim 46, wherein the at least one display is in communication with a User Interface that is configured to allow a user to electronically mark and/or select a target treatment site on the volumetric pre-acquired model and/or in a near RT MRI image and the at least one circuit is configured to define relevant anatomical scan planes associated with a selected or marked site.

49. The system of claim 46, wherein the at least one circuit is configured to allow a user via a User Interface in communication with the at least one display to show an electroanatomical (EA) map as the volumetric pre-acquired model, the EA map imported from a different imaging modality and/or generated from MRI data.

50. The system of claim 46, wherein the at least one circuit that is configured to allow a user using a User Interface associated with the at least one display to select an alternate visualization to provide a patient planning map that is shown on the at least one display aligned with or instead of the volumetric pre-acquired model with at least one target treatment site identified thereon registered to the 3-D MRI image space.

51. The system of claim 46, wherein the at least one display is in communication with a User Interface that allows a user to select whether to show a visual indication of at least one pre-identified target treatment site in the visualizations so that: (i) the at least one pre-identified target treatment site is shown only with the near RT MRI images; (ii) the at least one pre-identified target treatment site is shown in the near RT MRI images with the physical representations of the flexible intrabody catheters and without the volumetric pre-acquired model; or (iii) the at least one pre-identified target treatment site is shown with the volumetric pre-acquired model and the near RT MRI images.

52. The system of claim 46, wherein the at least one display is in communication with a User Interface, and wherein the User Interface is configured to allow a user to selectively fade and/or turn on and off tissue characterization and/or electroanatomical data in at least one visualization and to show such data either: (a) on the volumetric pre-acquired model; or (b) in the near RT MR images without the volumetric pre-acquired model.

53. The system of claim 46, wherein the at least one display is in communication with a User Interface, the User Interface configured to allow a user to fade and/or turn on and off the physical representations of the flexible intrabody catheters in the visualizations to show a near real-time MR image of at least one of the flexible intrabody catheters.

54. A method for performing an MRI-guided procedure, comprising:
 introducing a flexible intrabody medical device into a natural lumen or cavity of a patient during an MRI-guided procedure;
 electronically obtaining tracking signals from tracking coils connected to channels of an MR Scanner and attached to the flexible intrabody medical device during the MRI-guided procedure, wherein the flexible intrabody medical device has a distal end portion that can take on a non-linear shape as it moves into position in the patient's body;
 electronically identifying X, Y, Z coordinate locations in 3-D MRI image space of each of the tracking coils using the tracking signals;
 obtaining near RT MR image data of target anatomy of the patient during the MRI-guided procedure;
 obtaining a pre-acquired 3-D volumetric model of the target anatomy of the patient and registering the model to the 3-D image space;
 generating and displaying, using at least one processor, visualizations of the flexible intrabody medical device showing: (i) the 3-D volumetric model of the patient's target anatomy; (ii) a three dimensional physical representation of at least a distal end portion of the flexible intrabody medical device using the identified locations of the tracking coils, known spatial relationship between the tracking coils and dimensional characteristics of the distal end portion of the flexible intrabody medical device; and (iii) the near RT MR image data;
 electronically calculating a device-tissue interface location proximate a tip of the flexible intrabody medical device in the 3-D image space using the identified coordinate locations of the tracking coils, wherein the calculation is carried out to place the device-tissue interface location a distance of between about 0-5 mm beyond a calculated location of the distal tip of the flexible intrabody device, and wherein the calculated device-tissue interface is either (a) calculated to be tangent and substantially in-line with at least two of the tracking coils or (b) calculated as a plane in the 3-D MRI image space proximate a projected plane defined by at least three points associated with three different ones of the tracking coils; and
 automatically defining at least one scan plane used for the obtaining step to obtain the MR image data for the near RT images during and/or proximate in time to delivery of a therapeutic treatment and/or a diagnostic procedure using the calculated device-tissue interface location.

55. The method of claim 54, further comprising showing the tracking coils in the three-dimensional physical representation of the distal end portion of the flexible intrabody medical device in the visualizations in a three-dimensional shape or shapes and in different colors using the identified coordinate location of the tracking coils, the dimensional characteristics and a defined form factor regarding actual coil configuration and placement on the flexible intrabody medical device.

56. The method of claim 54, further comprising electronically rotating the visualizations based on user input and electronically selectively altering a displayed visualization based on user input so that the altered visualization includes the physical representation of the flexible intrabody medical device with (a) only a near RT image of the target anatomy, (b) both the near RT image of the target anatomy and the registered 3-D volumetric model of the anatomical structure, or (c) only the registered 3-D volumetric model of the anatomical structure.

57. The method of claim 54, wherein the 3-D volumetric model of the target anatomy comprises tissue characteristic map generated using MR image segmentation carried out prior to the MRI-guided procedure.

58. The method of claim 54, wherein the 3-D volumetric model of the target anatomy comprises an electroanatomical map.

59. The method of claim 54, further comprising allowing a user to alter the visualizations to selectively display one or more tissue characterization maps or data therefrom wherein the tissue characterization map selections include at least two of the following, which can be individually shown apart from or on the volumetric model:
 a thermal tissue characterization map;
 an edema tissue characterization map;
 a delayed enhancement tissue characterization map taken at a first point in time;
 a delayed enhancement tissue characterization map taken at a second point in time after at least some ablation lesions are created in heart tissue;
 a vasculature tissue map;
 a fibrous tissue map;
 a hypoxic tissue characterization map;
 an ischemic tissue characterization map;
 a fluid distribution map;
 a light exposure map; and
 an electroanatomical map.

60. A computer program product for facilitating an MRI-guided interventional therapy in a patient, the computer program product comprising:
 a computer readable non-transitory storage medium having computer readable program code embodied in the medium, the computer-readable program code configured to:
 direct an MRI Scanner to obtain in an interleaved manner (a) tracking signal data from tracking coils associated with an intrabody flexible device and (b) MR image data, both in the same 3-D MRI image space with a coordinate system;
 generate near real time (RT) MRI images of at least a portion of target anatomy of a patient using relevant anatomical scan planes;
 identify spatial coordinates associated with a location of at least a distal end portion of the intrabody flexible device in the 3-D MRI image space using the tracking signal data;
 render dynamic near RT three-dimensional visualizations of the intrabody flexible device in the 3-D image space with near RT MRI images; and
 calculate a location in the 3-D MRI image space of a device tissue interface associated with a tip and/or distal end portion of the intrabody flexible device to identify at least one of the relevant anatomical scan planes wherein the distal end portion of the intrabody flexible device can vary in shape during the MRI-guided procedure, and wherein the computer readable program code that calculates the location is configured to use X, Y, Z coordinates of locations of the tracking coils and known spacing of the tracking coils to place the location of device-tissue interface a distance of between about 0-5 mm beyond a calculated location of the tip of the intrabody flexible device, and wherein the calculated device-tissue interface location is either (a) calculated to be tangent and substantially in-line with at least two of the tracking coils or (b) calculated as a plane in the 3-D MRI image space proximate a projected plane defined by at least three points associated with three different ones of the tracking coils.

61. The computer program product of claim 60, further: wherein the computer readable program code is further configured to use the calculated device-tissue interface location to automatically define at least one scan plane used by the MRI Scanner as at least one of the relevant anatomical scan planes to obtain the MR image data for the near RT MRI images during and/or proximate in time to delivery of a therapeutic treatment and/or a diagnostic procedure.

62. The computer program product of claim 61, wherein the computer readable program code that renders the dynamic visualizations further comprises computer readable program code that provides a registered pre-acquired volumetric model of a patient's target anatomical structure in the visualizations.

63. The computer program product of claim 62, wherein the computer readable program code is further configured to allow a user to (a) rotate the visualization and (b) alter a displayed visualization to remove the pre-acquired model but include the near RT images of the target anatomy, to include the near RT images of the target anatomy and the registered pre-acquired volumetric model of the anatomical structure, or to include the registered pre-acquired volumetric model of the anatomical structure without the near RT MRI image of the target anatomy.

64. The computer program product of claim 62, wherein the computer readable program code is further configured to allow a user to electronically mark or select target lesion sites on the pre-acquired volumetric model.

65. The computer program product of claim 62, wherein the computer readable program code further configured to allow a user to electronically selectively display one or more tissue maps aligned with and/or registered to the pre-acquired volumetric model wherein the defined tissue maps include at least two of the following:
   a thermal tissue characterization map;
   an edema tissue characterization map;
   a delayed enhancement tissue characterization map taken at a first point in time;
   a delayed enhancement tissue characterization map taken at a second point in time after at least some ablation lesions are created in heart tissue;
   a vasculature tissue map;
   a fibrous tissue map;
   a hypoxic tissue characterization map;
   an ischemic tissue characterization map;
   a fluid distribution map;
   a light exposure map; and
   an electroanatomical map.

66. A cardiac interventional system, comprising:
   a display;
   an MRI Scanner;
   at least one processor in communication with the display and adapted to communicate with the MRI Scanner for:
   (a) generating near real time (RT) MRI images of at least a portion of a heart of a patient using relevant anatomical scan planes associated with a 3-D MRI image space having a coordinate system;
   (b) identifying X, Y, Z coordinates in the same 3-D MRI image space associated with a location of at least a distal end portion of at least one flexible intrabody catheter using tracking coil signal data from tracking coils held by the at least one flexible intrabody catheter;
   (c) rendering dynamic near RT visualizations of the at least one flexible intrabody catheter in the 3-D image space;
   (d) calculating a location in the 3-D MRI image space of a catheter-tissue interface associated with a tip and/or distal end portion of the at least one flexible intrabody catheter to identify at least one of the relevant anatomical scan planes,
   wherein calculating the location of the catheter-tissue interface is carried out using the X, Y, Z coordinates of locations of the tracking coils and known spatial spacing between the tracking coils, wherein the calculation is carried out to place the interface location a distance of between about 0-5 mm beyond a calculated location of the tip of the at least one flexible intrabody catheter, and wherein the calculated interface is either (a) calculated to be tangent and substantially in-line with at least two of the tracking coils or (b) calculated as a plane in the 3-D MRI image space proximate a projected plane defined by at least three points associated with three different ones of the tracking coils;
   (e) displaying a graphical user interface (GUI) containing at least one of the visualizations within or on the display; and
   (f) selectively altering the visualizations by a user using the GUI to show different volumetric patient-specific tissue maps.

67. The system of claim 66, wherein the computer program code that is executable by the processor is further adapted to automatically define at least one scan plane used by the MRI scanner associated with the catheter-tissue interface.

68. The system of claim 66, wherein the computer program code that is executable by the processor is further adapted to accept user input via the GUI to selectively fade and/or turn on and off tissue characterization or electroanatomical data in the visualizations.

69. The system of claim 68, wherein the computer program code that is executable by the processor to selectively fade and/or turn one and off data is carried out to show the tissue characterization or electroanatomical data.

70. The system of claim 66, wherein the computer program code that is executable by the processor is further adapted to accept user input via the GUI to selectively fade and/or turn on and off visual indications of target treatment sites in the visualizations.

71. The system of claim 66, further comprising computer program code that is executable by the processor to selectively show pre-defined target treatment sites either: (a) on a three dimensional pre-acquired model of a patient's heart in the visualizations, the three dimensional pre-acquired model shown in and/or registered to the 3-D imaging space; or (b) in the near RT MR images without the three dimensional pre-acquired model.

72. The system of claim 66, wherein the computer program code residing in the memory that is executable by the processor is also configured for:
   directing the MRI Scanner to interleave a tracking sequence and an imaging sequence, the imaging sequence comprises the anatomical scan planes used to generate the near RT MRI images, wherein the tracking sequence is carried out independent of the imaging sequence, and wherein the tracking sequence generates the X, Y, Z coordinates of the tracking coils of the distal end portion of the flexible catheter from signals from different MR scanner channels that the tracking coils are connected to.

73. The system of claim 72, wherein the tracking sequence identifies the X, Y, Z coordinates of the tracking coils simultaneously.

74. The system of claim 72, wherein the tracking sequence dephases signal perpendicular to a read-out direction to attenuate unwanted signal from 1) bulk objects and 2) regions sensed by signal sensitive parts of the flexible catheter to thereby leave a sharp peak indicating position of the tracking coils, and wherein once a tracking sequence is complete, a spoiler gradient can be used to diphase any transverse signal remaining before the image sequence is executed.

75. The system of claim 72, wherein the tracking sequence comprises a plurality of small flip angle excitation with each repetition designed to indicate the X, Y or Z component of the tracking coil coordinates in succession.

* * * * *

UNITED STATES PATENT AND TRADEMARK OFFICE
CERTIFICATE OF CORRECTION

Page 1 of 1

PATENT NO. : 9,439,735 B2
APPLICATION NO. : 12/796017
DATED : September 13, 2016
INVENTOR(S) : Guttman et al.

It is certified that error appears in the above-identified patent and that said Letters Patent is hereby corrected as shown below:

In the Claims

Column 41, Claim 2, Line 39: Please correct "Claim 1, , wherein" to read -- Claim 1, wherein --

Column 43, Claim 14, Line 5: Please correct "and connect" to read -- and to connect --

Column 45, Claim 33, Line 65: Please correct "data is" to read -- data therefrom is --

Column 49, Claim 54, Line 47: Please correct "3-D" to read -- 3-D MRI --

Column 51, Claim 65, Line 49: Please correct "model wherein" to read -- model, wherein --

Column 52, Claim 69, Line 53: Please correct "one" to read -- on --

Signed and Sealed this
Fourth Day of July, 2017

Joseph Matal
*Performing the Functions and Duties of the*
*Under Secretary of Commerce for Intellectual Property and*
*Director of the United States Patent and Trademark Office*